US008961185B2

(12) United States Patent
Bleich et al.

(10) Patent No.: US 8,961,185 B2
(45) Date of Patent: Feb. 24, 2015

(54) SYSTEM AND METHOD FOR RELIABLY COORDINATING MUSCULOSKELETAL AND CARDIOVASCULAR HEMODYNAMICS

(75) Inventors: Jeffery Lee Bleich, Palo Alto, CA (US); Paul David Mannheimer, Danville, CA (US); Jeffrey Lawrence Michels, San Francisco, CA (US); Marc David Anker, Palo Alto, CA (US)

(73) Assignee: Pulson, Inc., Palo Alto, CA (US)

( * ) Notice: Subject to any disclaimer, the term of this patent is extended or adjusted under 35 U.S.C. 154(b) by 143 days.

(21) Appl. No.: 13/589,073

(22) Filed: Aug. 17, 2012

(65) Prior Publication Data
US 2013/0171599 A1 Jul. 4, 2013

Related U.S. Application Data

(60) Provisional application No. 61/525,689, filed on Aug. 19, 2011.

(51) Int. Cl.
*G09B 3/00* (2006.01)
*G09B 19/00* (2006.01)
(Continued)

(52) U.S. Cl.
CPC .............. *G09B 19/00* (2013.01); *A61B 5/0456* (2013.01); *A63B 71/0686* (2013.01); *A63B 15/00* (2013.01); *A63B 24/0062* (2013.01); *A63B 24/0075* (2013.01); *A63B 24/0087* (2013.01); *A63B 2230/425* (2013.01); *A63B 69/0028* (2013.01); *A61H 1/0255* (2013.01); *A61H 1/0274* (2013.01); *A61H 3/00* (2013.01); *A63B 21/0023* (2013.01); *A63B 21/06* (2013.01);
(Continued)

(58) Field of Classification Search
USPC ........................... 434/247, 322–365; 482/1–9
See application file for complete search history.

(56) References Cited

U.S. PATENT DOCUMENTS 2,690,174 A 3/1949 Fuchs
3,303,841 A 2/1967 Dennis
(Continued)

FOREIGN PATENT DOCUMENTS

WO PCT/US2012/051511 8/2012

OTHER PUBLICATIONS

Zhang, D. et al., "The effect of heartbeat-synchronized running on the cardiovascular system", Conference Proceedings, Second Joint EMBS-BMES Conference 2002, 24th Annual International Conference of the Engineering in Medical and Biology Society, Annual Fall meeting of the Biomedical Engineering Society, IEEE, vol. 2, 2002, pp. 1295-1296, No. XP010620075.
(Continued)

*Primary Examiner* — Timothy A Musselman
(74) *Attorney, Agent, or Firm* — Watson Rounds; Marc D. Foodman

(57) ABSTRACT

Systems and methods are disclosed to enable a user to favorably coordinate the timing of musculoskeletal movement and skeletal muscle contraction and relaxation with the cardiac pumping cycle in order to improve perfusion of cardiac and peripheral skeletal muscle and other tissues, increase physiological efficiency, decrease myocardial stress, and enhance individual performance, health and safety during rhythmic physical activity. Additionally, systems and methods are disclosed to enable a user to avoid inadvertent unfavorable coordination of musculoskeletal movement and skeletal muscle contractions and relaxation cycles with the cardiac pumping cycle during physical activity.

72 Claims, 37 Drawing Sheets

(51) Int. Cl.
*A61B 5/0456* (2006.01)
*A63B 71/06* (2006.01)
*A63B 15/00* (2006.01)
*A63B 24/00* (2006.01)
*A63B 69/00* (2006.01)
*A61H 1/02* (2006.01)
*A61H 3/00* (2006.01)
*A63B 21/002* (2006.01)
*A63B 21/06* (2006.01)
*A63B 22/00* (2006.01)
*A63B 22/02* (2006.01)
*A63B 22/06* (2006.01)
*A63B 23/12* (2006.01)

(52) U.S. Cl.
CPC ......... *A63B22/0023* (2013.01); *A63B 22/0056* (2013.01); *A63B 22/0076* (2013.01); *A63B 22/0235* (2013.01); *A63B 22/0605* (2013.01); *A63B 22/0664* (2013.01); *A63B 23/1218* (2013.01); *A63B 23/1236* (2013.01); *A61H 2201/1633* (2013.01); *A61H 2201/1642* (2013.01); *A61H 2201/5015* (2013.01); *A61H 2201/5064* (2013.01); *A61H 2201/5071* (2013.01); *A61H 2201/5084* (2013.01); *A61H 2201/5092* (2013.01); *A61H 2201/5097* (2013.01); *A61H 2230/045* (2013.01); *A61H 2230/065* (2013.01); *A61H 2230/208* (2013.01); *A61H 2230/305* (2013.01); *A61H 2230/42* (2013.01); *A61H 2230/50* (2013.01); *A61H 2230/60* (2013.01); *A61H 2230/805* (2013.01); *A63B 2021/0026* (2013.01); *A63B 2024/0093* (2013.01); *A63B 2024/0096* (2013.01); *A63B 2071/0625* (2013.01); *A63B 2071/0655* (2013.01); *A63B 2071/0663* (2013.01); *A63B 2220/10* (2013.01); *A63B 2220/17* (2013.01); *A63B 2220/40* (2013.01); *A63B 2220/56* (2013.01); *A63B 2220/805* (2013.01); *A63B 2220/806* (2013.01); *A63B 2220/833* (2013.01); *A63B 2220/836* (2013.01); *A63B 2220/89* (2013.01); *A63B 2225/50* (2013.01); *A63B 2225/54* (2013.01); *A63B 2230/045* (2013.01); *A63B 2230/062* (2013.01); *A63B 2230/207* (2013.01); *A63B 2230/50* (2013.01); *A63B 2230/60* (2013.01); *A63B 2230/75* (2013.01); *A63B 2244/20* (2013.01)
USPC .......................................... 434/247; 434/258

(56) References Cited

U.S. PATENT DOCUMENTS

| | | | |
|---|---|---|---|
| 4,253,254 | A | 3/1981 | Gill |
| 4,541,417 | A | 9/1985 | Krikorian |
| 4,867,442 | A | 9/1989 | Matthews |
| 5,137,501 | A | 8/1992 | Mertsesdorf |
| 5,462,504 | A | 10/1995 | Trulaske |
| 5,571,075 | A | 11/1996 | Bullard |
| 5,697,884 | A | 12/1997 | Francischelli |
| 6,132,337 | A | 10/2000 | Krupka |
| 6,155,976 | A | 12/2000 | Sackner |
| 6,261,236 | B1 | 7/2001 | Grimblatov |
| 6,261,250 | B1 | 7/2001 | Phillips |
| 6,537,229 | B1 | 3/2003 | Wang |
| 6,605,046 | B1 | 8/2003 | Del Mar |
| 7,643,873 | B2 | 1/2010 | Chan |
| 2004/0072133 | A1 | 4/2004 | Kullok |
| 2004/0077954 | A1 | 4/2004 | Oakley |
| 2008/0165017 | A1 | 7/2008 | Schwartz |
| 2008/0236369 | A1 | 10/2008 | Sasaki |
| 2009/0036938 | A1 | 2/2009 | Shipley |
| 2009/0076341 | A1 | 3/2009 | James et al. |
| 2010/0189209 | A1 | 7/2010 | O'Rourke |

OTHER PUBLICATIONS

Coleman, W., "The Psychological Significance of Bodily Rhythms", The Journal of Comparative Psychology, vol. 1, pp. 213-220, 1921.

Coleman, W., "On the Correlation of the Rate of Beat, Breathing, Bodily Movement Sensory Stimuli", J. Physiol, vol. 54, No. 4, pp. 213-217, Dec. 7, 1920.

Heagerty, A., "Winning rhythm?", The Lancet, vol. 343, pp. 310, Feb. 5, 1994.

Kirby, et al., "Coupling of cardiac and locomotor rhythms", American Physiological Society, 0161-7567/89, pp. 323-329, 1989.

McDonald, D., "Regional Pulse-Wave Velocity in the Arterial Tree", J. Applied Physiology, vol. 24, No. 1, pp. 73-78, 1968.

Murry et al., "Preconditioning with ischemia: a delay of lethal cell injury in ischemic myocardium", Circulation, vol. 74, No. 5, pp. 1124-1136, 1986.

Nichols et al., "McDonald's Blood Flow in Arteries", Chapter 25 "Exercise", pp. 452-498, Hodder Arnold Publishers, Apr. 28, 2005.

Niizeki et al., "Phase-dependent heartbeat modulation by muscle contractions during dynamic handgrip in humans", American Physiological Society, 0363-6135/99, pp. H1331-H1338, 1999.

Niizeki K., "Intramuscular pressure-induced inhibition of cardiac contraction: implications for cardiac-locomotor synchronization", Am J Physiol Regul Integr Comp Physiol 288: R645-R650, 2005 (First published Nov. 4, 2004; doi:10.1152/ajpregu.00491, 2004).

Nomura, et al., "Analysis entrainment of cardia and locomotor rhythms in humans using the surrogate data technique", European Journal of Applied Physiology, vol. 84, No. 5, pp. 373-378, 2001.

Nomura, et al., "Phase-dependent chronotropic response of the heart during running in humans", Eur J Appl Physiol vol. 97, pp. 240-247, 2006.

O'Rourke et al., "Improved cardiovascular performance with optimal entrainment between heart rate and step rate during running in humans", Coronary Artery Disease vol. 3, pp. 863-869, 1992.

O'Rourke et al., "The rhythm of running: can the heart join in?", Aust NZ J Med, vol. 23, pp. 708-710, 1993.

Palatini et al., "Blood pressure changes during running in humans: the "beat" phenomenon", American Physiological Society, 0161-7567, 1989.

Zhang et al., "Possible Mechanisim for Modulating Cardiovascular System During Running in Humans", 23rd Annual International Conference of the IEEE Engineering in Medicine and Biology Society, Oct. 25-26, 2001.

Zhang et al., "Monitoring Physiological Signals During Running Exercise", 23rd Annual International Conference of the IEEE Engineering in Medicine and Biology Society, Oct. 25-26, 2001.

Zhao et al., "Inhibition of myocardial injury by ischemic postconditioning during reperfusion: comparison with ischemic preconditioning", Am J Physiol Heart Circ Physiol 285: H579-H588, 2003 (first published Apr. 3, 2003; 10.1152/ajpheart.01069, 2002).

D. Zheng, An experimental and modeling study of the relationship between step rate and heart rate during running exercise, Doctorate Thesis, University of New South Wales, Sydney, Australia, 2002.

T. Nakazumi et al., Entrainment of the heart beat into the running pitch during endurance running [I] Japanese J Phys Fitness and Sports Med 1986, vol. 36 No. 6, p. 340.

M. Udo M, et al., Entrainment of the heart beat into the running pitch during endurance running [II]. Japanese J Phys Fitness and Sports Med 1986, vol. 36, No. 6, p. 341.

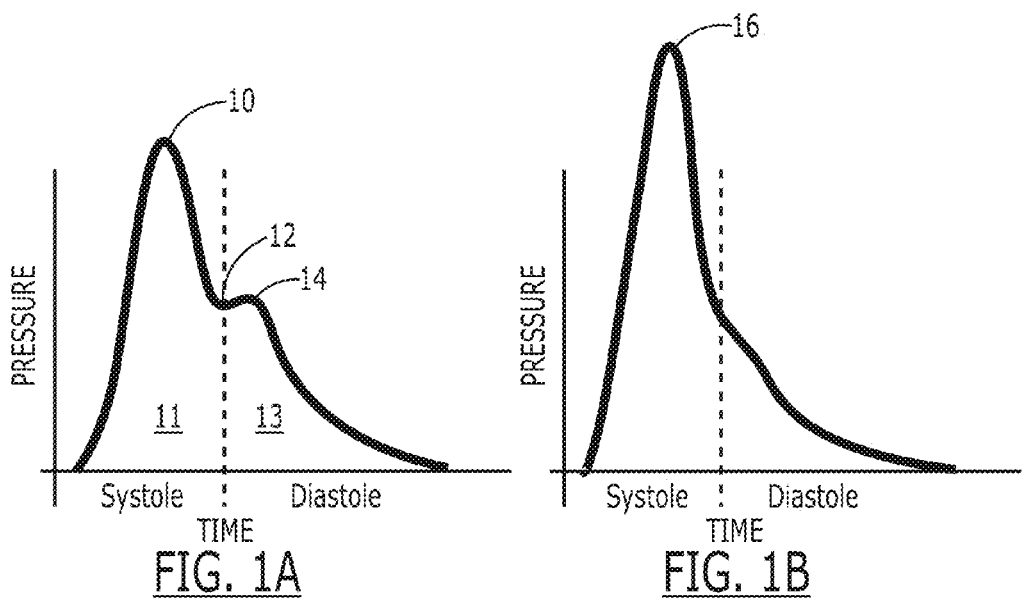
FIG. 1A
FIG. 1B
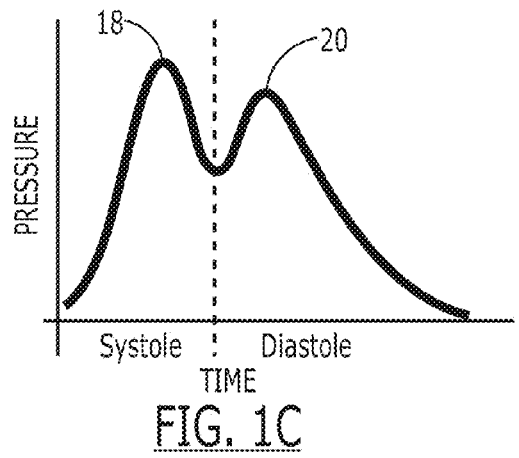
FIG. 1C
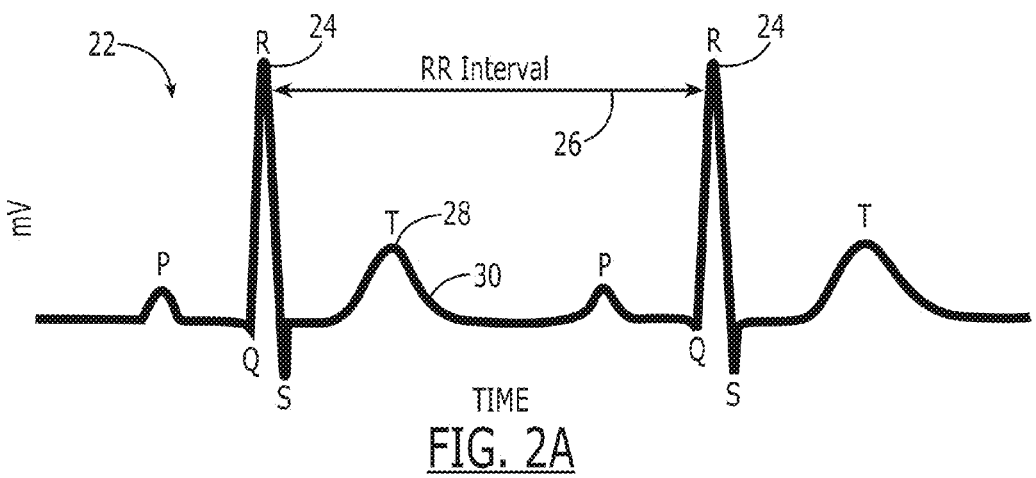
FIG. 2A

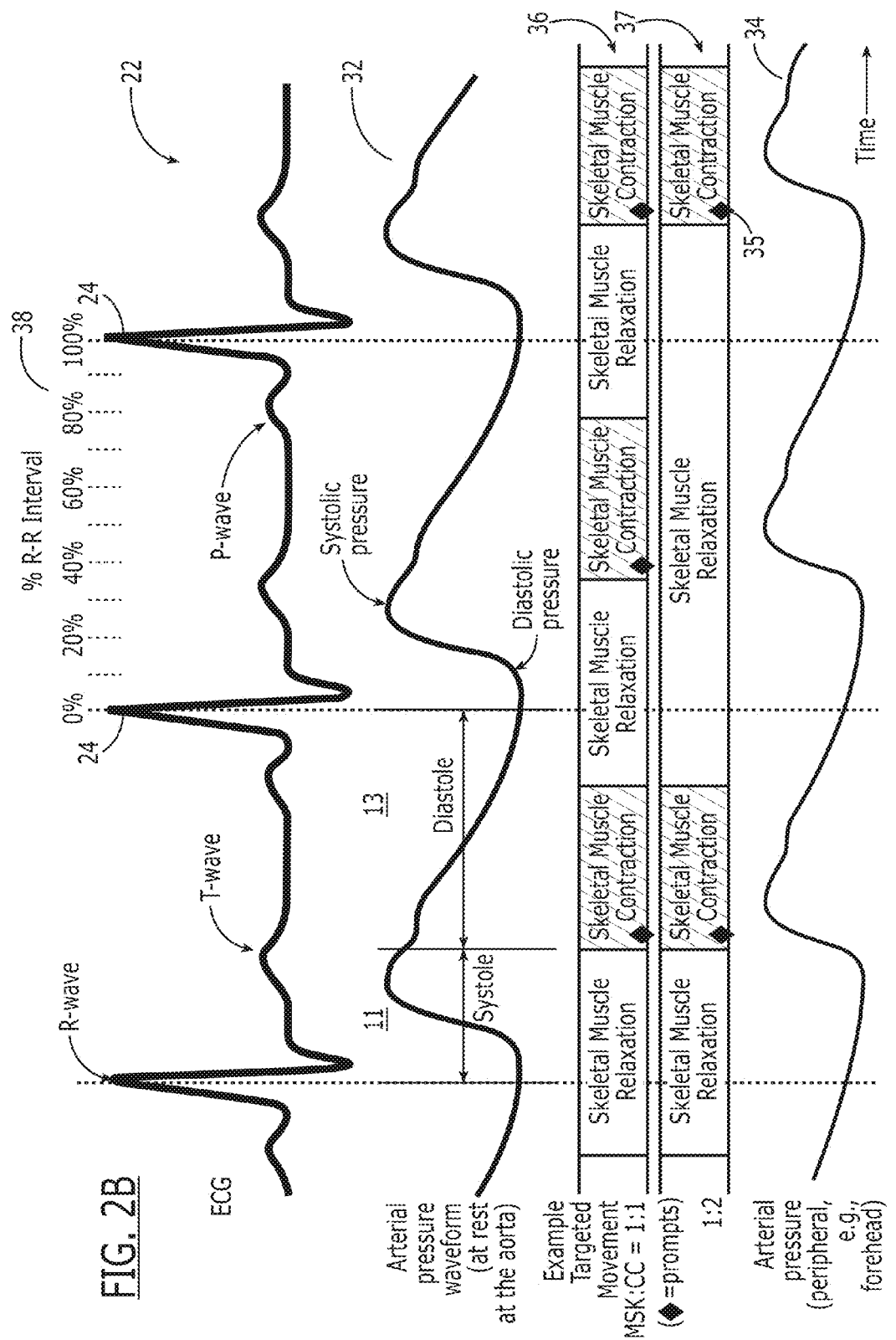

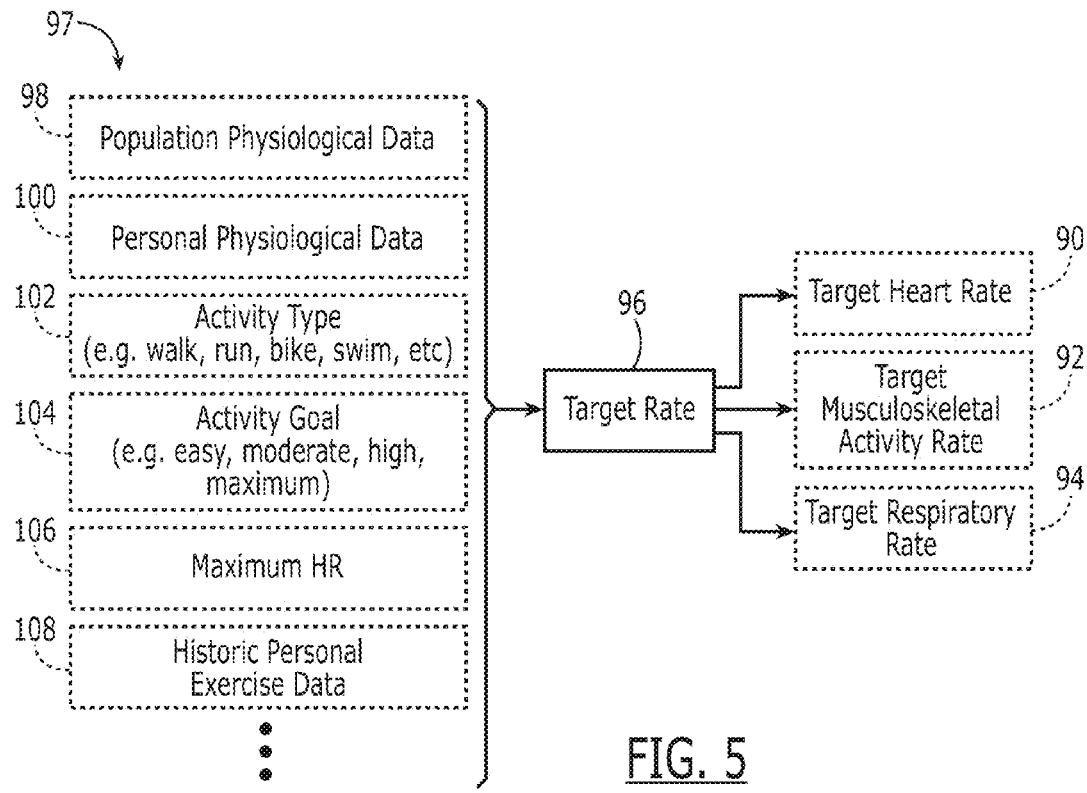
FIG. 5
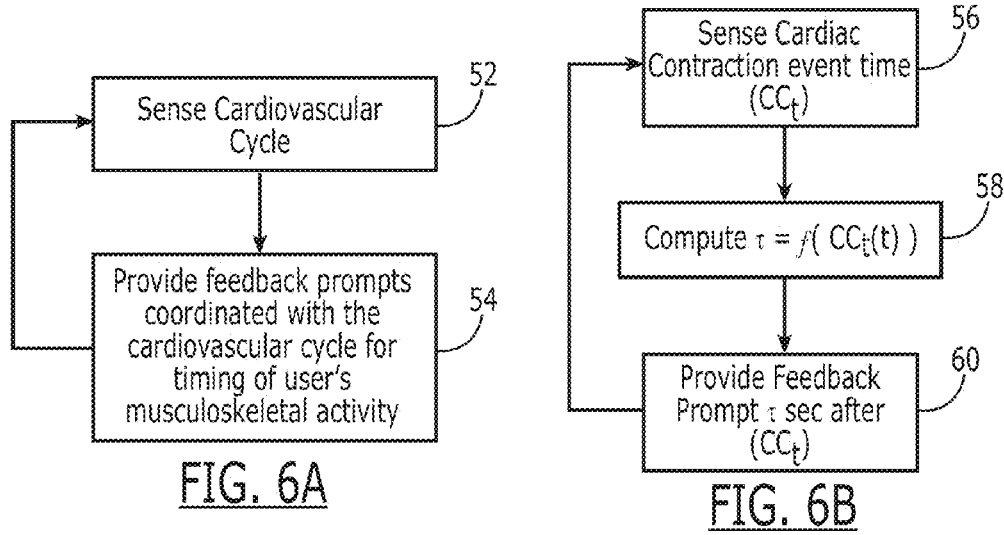
FIG. 6A
FIG. 6B

User response aligned in time with feedback prompt

User "late" in response to feedback prompt

Feedback prompt timing changed to adapt to user

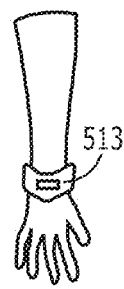
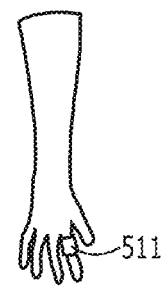
FIG. 32G  FIG. 32H
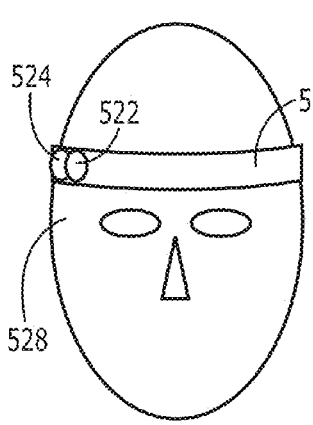
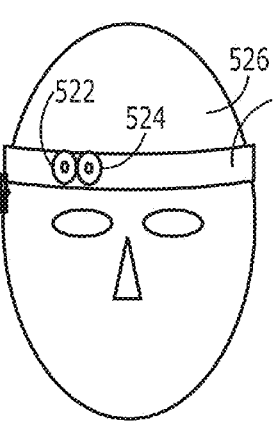
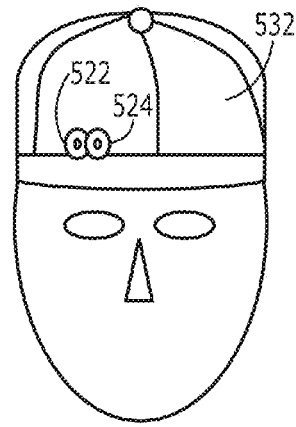
FIG. 33A  FIG. 33B  FIG. 33C
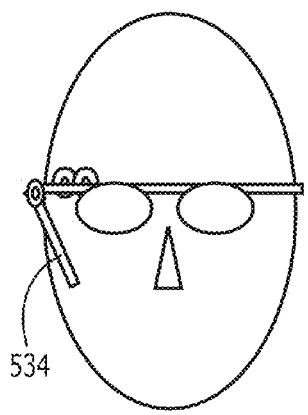
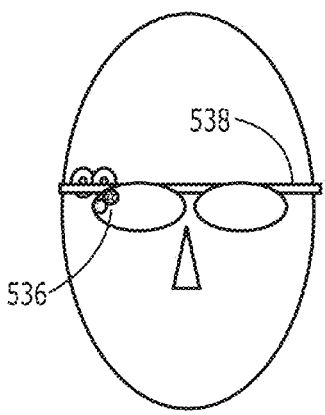
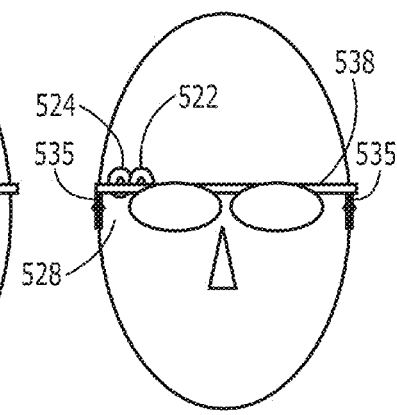
FIG. 33D  FIG. 33E  FIG. 33F

SYSTEM AND METHOD FOR RELIABLY COORDINATING MUSCULOSKELETAL AND CARDIOVASCULAR HEMODYNAMICS

CROSS-REFERENCE TO RELATED APPLICATIONS

The present disclosure is related to and claims priority from copending Provisional U.S. Patent Application Ser. No. 61/525,689, filed on Aug. 19, 2011, and which in its entirety is incorporated herein by reference.

COPYRIGHT NOTICE

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND

The present disclosure is related generally to human physiology, and more specifically to methods and apparatus for improving hemodynamic efficiency and cardiac health through enabling a user to maintain favorable coordination of repetitive musculoskeletal (MSK) movement and skeletal muscle contraction cycles with the cardiac pumping cycle.

Blood is circulated through the body by the heart during its rhythmic pumping cycle, which consists of two distinct periods—systole and diastole. Heart muscle (myocardium) contracts to eject blood from the ventricles during the systolic period of each cardiac cycle (CC), generating arterial blood pressure and flow adequate to deliver blood throughout the body, thereby transporting oxygen, nutrients, metabolic products; removing carbon dioxide and waste; and also facilitating critical physiological functions such as heat exchange. The heart subsequently relaxes during the diastolic period of the CC, when the atrial and ventricular chambers refill with blood in preparation for the heart's next contraction.

Unlike the rest of the body, which receives most of its blood flow as a result of pressure generated during systole, the heart's own arterial blood supply is delivered primarily during the diastolic portion of the cycle when the heart muscle is relaxing and the heart chambers are filling for the next contraction. Little blood flows to perfuse the myocardium during systole because the heart's contraction generates high forces within its muscular walls and thereby prevents flow through the coronary blood vessels that travel across and through the myocardium. During diastole, when the heart muscle has relaxed, residual blood pressure in the aorta drives blood flow through the coronary arteries, supplying the heart with its needed oxygen and nutrients.

In addition to the heart's pumping function, the MSK system can also play an important role in circulating blood throughout the body during physical activity. In fact, blood is rhythmically pumped via transient changes in peripheral vascular pressure induced by many types of repetitive MSK activities, including skeletal muscle contraction, skeletal muscle relaxation, and MSK movement. Examples of types of rhythmic MSK activities that can be important inducers of peripheral vascular pumping include ambulation, aerobic exercise, endurance sports, and resistance training. Rhythmic skeletal muscle contraction and relaxation can cause regular oscillations in peripheral arterial and venous pressure due to intermittent compression of the vasculature, while MSK movement leads to periodic acceleration and deceleration of the intravascular volume of blood against gravity and inertia. Regular oscillations that result from rhythmic muscle contraction can be favorably coordinated with the heart's pump cycle such that the cardiac and MSK pumps augment one another, thereby increasing blood flow and perfusion to important areas of the body with less pumping energy expended. However, unfavorable coordination of the two pumping systems can also occur, leading to decreased pumping efficiencies along with a concurrent decrease in perfusion of important tissues.

In the medical field, there are multiple therapeutic modalities that impact extra-cardiac blood flow in ways that are similar to the hemodynamic effects of the MSK system during rhythmic physical activity. These therapeutic interventions typically require large electromechanical devices in order to monitor cardiovascular rhythm and hemodynamics, while creating driving forces external to the body's own MSK system in order to impact circulation of blood throughout the body. For example, standard medical therapies such as Mechanical External Counter-Pulsation (commonly known as ECP or EECP) and Intra-aortic Balloon Counter-Pulsation (via an Intra-aortic balloon pump or IABP) are two techniques that generate periodic acceleration and deceleration of the peripheral vascular and aortic volume of blood timed in careful coordination with the heart's cycle. ECP and IABPs are well-known therapeutic modalities that have been reported in peer reviewed journal articles to be helpful in treating symptoms of myocardial ischemia, congestive heart failure, and myocardial infarction.

ECP is a noninvasive technology that rapidly mechanically compresses vasculature in the extremities in synch with the monitored cardiac rhythm in order to facilitate both coronary arterial and systemic venous blood flow to the heart during diastole. Mechanized pressure cuffs that have typically been placed around the legs, and sometimes the buttocks, are inflated in sequence, beginning with the distal limb and rapidly progressing proximally, during the diastolic period of the CC. (The upper extremities are less frequently treated due to their smaller size and lower intravascular volume.) The ECP device subsequently rapidly relaxes compression just prior to the next cardiac contraction, allowing blood to again flow through the extremities, facilitating systemic arterial blood flow from the heart during systole. ECP simultaneously pumps both arterial and venous blood from the patient's extremities in coordination with the diastolic portion of the heart cycle in order to increase the flow of oxygen-rich arterial blood to the heart musculature (myocardium), and to increase the flow of venous blood towards the hearts pumping chambers, while the heart muscle is relaxing between contractions. Furthermore, by timing the release of the cuffs' compressions just prior to the next heart contraction, with the emptied peripheral vessels reducing systemic vascular resistance (SVR), ECP improves heart function by decreasing its workload during systole. Other methods of inducing ECP for patients have been described, including rapidly and rhythmically tilting the patient, head-to-toe, in coordination with the CC, in order to induce similar cyclical increases and decreases in SVR.

Studies have suggested that powered ECP is a safe and effective non-invasive means of increasing cardiac perfusion and decreasing cardiac work, thereby decreasing angina in patients suffering from myocardial ischemia. ECP has also been used to improve cardiac function in patients suffering from Congestive Heart Failure (CHF). ECP has even been credited with improving perfusion in the treatment of cerebrovascular disease, wound management, and other disease entities where compromised vascular perfusion is present. The benefits of ECP are reported to continue beyond the duration of the therapy (common treatment of 60 minutes daily, for 4-8 weeks). The reasons cited for the long-term benefits of ECP include claims that increased shear forces in the Coronary Arteries lead to angiogenesis and increased growth of collateral coronary arteries that improve perfusion and are cardio-protective against future ischemic insult.

The combination of an increase in coronary artery perfusion pressures and flow and a decrease in cardiac afterload, also drives the beneficial cardiac effects of IABP counterpulsation. The IABP can be utilized as a temporary cardiac assist device, as when a patient is in transient severe heart failure, when the heart requires hemodynamic support perioperatively, or in circumstances of extreme cardiovascular (CV) compromise, such as when a patient is experiencing severe angina that is refractory to standard medical therapies. The IABP device is inflated in the aorta during early diastole and deflated just prior to the onset of systole.

However, the automated mechanical pump methodologies described above require some form of apparatus that provides the pulsation supplementation. In certain cases, they require that an individual be otherwise at rest during treatment. In some cases, the methodologies require surgical or intravascular intervention.

SUMMARY

For the purpose of clarity, the following terminology and abbreviations are used throughout this disclosure:
CC Cardiac Cycle, equivalently Cardiovascular Cycle
CCt Detected CC event time
CV Cardiovascular
ECG Electrocardiogram
EMG Electromyogram
HR Heart Rate
aHRA Average HR
tHRT Target HR
MCP Musculoskeletal Counterpulsation
iMCP Inverse MCP
MSK Musculoskeletal
$MSK_t$ Detected MSK event time
$MSK_\phi$ Phase of a user's MSK activity relative to their CC
PPG Photoplethysmogram
RRI R-wave to R-wave interval (R-R time interval) within an ECG signal
SVR Systemic Vascular Resistance
τ (tau) A delay time For purposes of this disclosure, the term "musculoskeletal counter-pulsation" (MCP) describes self-induced peripheral vascular pumping resulting from rhythmic physical activity that is properly timed in relation to the heart's pumping cycle, allowing a user to optimize and maintain at least one of the following potentially desirable effects:
1. an increase in myocardial perfusion due to an increase in central arterial blood pressure during diastole;
2. a decrease in myocardial work due to a decrease in systemic arterial vascular resistance during systole;
3. an increase in skeletal muscle blood flow during systole due to relaxation of systemic musculature during peak systolic blood flow; and
4. an increase in venous return to the heart during cardiac diastole.

As a result, favorable coordination of MSK pump timing and heart pump timing can potentially lead to one or more of several benefits, including a lower heart rate (HR) due to increased cardiac preload and stroke volume; a decrease in systolic blood pressure and pulse pressure; a decrease in myocardial oxygen consumption; a decrease in required respiratory effort to meet the decreased oxygen demands; and less muscle fatigue due to improved skeletal muscle perfusion. For these reasons, there is even the possibility of acutely improving health safety during exercise, as well as results of fitness and health diagnostic tests such as lactic acid threshold, MVO2, and exercise stress testing.

Some of the central hemodynamic effects of MCP can be identified by comparing an exemplary central arterial blood pressure curve of a healthy young individual at rest (FIG. 1A) to central arterial blood pressure curves of the same individual that could occur during physical activity (FIGS. 1B and 1C). FIG. 1B depicts an exemplary central arterial blood pressure when the timing of cardiac systole (heart pumps blood to into the aorta) occurs at the same time as maximal pumping of blood by the MSK system. Alternatively, FIG. 1C depicts a more hemodynamically favorable exemplary central arterial pressure when maximal MSK pumping occurs during cardiac diastole.

Depending on the timing and direction of these peripheral blood-pumping actions relative to the heart's pumping cycle, these MSK activity-related mechanisms can either enhance or reduce the blood flow generated by the heart's function. Favorable coordination of the cardiac and peripheral blood pumps is not something that happens automatically. In fact, our research suggests that consistent optimal pump coordination, despite its potential advantages, is the exception rather than the rule.

Accordingly, the present disclosure is directed to systems and methods to enable a user to favorably coordinate the timing of MSK movement and skeletal muscle contraction and relaxation with the cardiac pumping cycle (FIG. 6A) in order to improve perfusion of cardiac and peripheral skeletal muscle and possibly other tissues, increase physiological efficiency, decrease myocardial stress, and potentially enhance individual performance—as well as the health benefits and safety—of rhythmic physical activity. Additionally, systems and methods are disclosed to enable a user to avoid inadvertent unfavorable coordination of MSK movement and skeletal muscle contractions cycles with the cardiac pumping cycle during physical activity.

Systems and methods are therefore disclosed to assist a user with coordinating rhythmic MSK activity with targeted timing relative to the cardiac pumping cycle. Guidance may thereby be provided in order to obtain and maintain a hemodynamically coordinated rhythmic skeletal muscle contraction cycle that favorably times regular oscillations in peripheral arterial and venous pressures due to compression of the vasculature within the skeletal musculature. Guidance can further thereby be provided in order to obtain favorably timed hemodynamically coordinated rhythmic MSK movement, along with the periodic acceleration and deceleration of the intravascular volume of blood and the resulting inertial effects on local and central arterial and venous blood pressures. Guidance can also thereby be provided in order to help a user to avoid undesired hemodynamic effects of rhythmic muscle contraction or MSK movement cycles that are particularly disadvantageously timed relative to the user's CC.

Systems and methods are further disclosed that utilize heart rhythm sensors, with and without MSK sensors, in conjunction with guidance programming algorithms that adjust the timing of the guidance, as needed, in order to obtain and maintain targeted timing of pumping of the peripheral vasculature by skeletal muscle contraction or movement. The MSK sensors and heart rhythm sensors that inform guidance programming algorithms can further thereby be provided in order to adaptively obtain and maintain hemodynamically favorably coordinated rhythmic MSK activity. Adaptive guidance algorithms can also thereby be provided in order to help a user to avoid undesired hemodynamic effects of rhythmic muscle contraction or MSK movement cycles that are particularly disadvantageously timed relative to the user's CC.

Accordingly, an objective of certain systems and methods described herein is to provide recurring guidance prompts to aid a user in properly timing their musculoskeletal activity cadence, with the prompt timing adaptive to changes in the user's heart rate so as to substantially maintain alignment of the prompt timing at a target location within the user's cardiac cycle.

An objective of certain other systems and methods described herein is to provide recurring guidance prompts to aid a user in properly timing their musculoskeletal activity cadence, with the prompt timing adaptive to changes in the user's heart rate and sensed musculoskeletal activity timing so as to substantially maintain alignment of the user's musculoskeletal activity timing at a target location within the user's cardiac cycle.

While used in several implementations of the present disclosure, the term "adaptive" is intended herein to mean employing one or more dynamic factors such as a user's heart rate to determine the timing location for the provision of a prompt to indicate to a user a time to initiate a recurrent component of the user's rhythmic musculoskeletal activity. Adaptive can consider the timing location of the prompt in terms of a selected recurrent component of the user's CC, such as an R-wave. The timing location can be determined based on at least one of a portion of CC, adaptive determinations of absolute time from the start of the recurrent component of the user's CC; adaptive determinations of a fixed distance from a recurrent component of the user's ECG; a percentage of the way through the cardiac cycle period (such as % RRI); a specific physiological target in the user's cyclical heart rate (such as the end of the user's T-wave), and so on. Adaptive may further be determined based on assessment of a user's actual MSK activity relative to the target timing. Furthermore, as used in the current disclosure, the terms "target phase," "target location," "target point," and "target timing" can be used to identify a target in the cardiac cycle.

Systems and methods disclosed herein can provide feedback on the user's success towards achieving favorable timing of MSK activity relative to the targeted phase in the cardiac pumping cycle. The systems and methods can also permit users to gauge and optimize aspects of their MSK activity, including feedback on the quantity, quality and effectiveness of MSK kinetics towards improving the effectiveness of coordinated peripheral vascular compression or pumping during rhythmic physical activity.

The systems and methods of this disclosure can also permit users to gauge, coordinate and optimize their skeletal muscle contraction cycles, relative to the heart's pumping cycle, during activities where the inertial effects of movement are minimal, such as in accomplishing effective and coordinated peripheral vascular compression or pumping via skeletal muscle contraction during rhythmic resistance training exercises. Isometric and isotonic exercises are both approaches to resistance training, which are forms of strength training in which each effort is performed against a specific opposing force generated by resistance (e.g. resistance to being pushed, pulled, squeezed, stretched or bent). Exercises can be isotonic if a body part is moving against the force. Exercises are isometric if the skeletal muscles are contracting but the body part is not substantially moving.

Commonly, of course, naturally occurring repetitive physical activity is not performed at exactly the same cadence as the HR. When the cadence and HR occur at substantially different rates, vascular pumping from the physical activity typically alternates back and forth between enhancing myocardial perfusion and oxygenation (increased diastolic pressures), and reducing it (reduced diastolic pressures), with neither condition typically persisting for extended continuous periods of time. While this condition may not be as advantageous as when MSK activity is properly aligned with the as described earlier, the heart muscle typically continues to be adequately perfused. If, however, one were to move with a cadence at or very close to the HR, with the timing of physical activity unfavorably aligned with the CC for more extended periods of time, the resulting prolonged increase in cardiac work load (increased systolic pressure) and decreased blood flow and oxygen delivery to the heart tissues (decreased diastolic pressures) may put the myocardium at greater risk of becoming dangerously ischemic, especially during strenuous physical activity of longer durations. In fact, inadvertent periods of this type of persistent unfavorable timing may be at the root of some of the acute and chronic myocardial injury reported in long and ultra-long distance runners and walkers. Therefore, additionally or alternatively, systems and methods herein can provide feedback that informs the user to specifically avoid MSK movement timing and peripheral muscular contraction cycle timing that would be likely to result in prolonged periods of unfavorable CV hemodynamics, thereby avoiding the deleterious consequences of a concurrent negative impact on myocardial perfusion with an increase in systolic blood pressure and required cardiac work.

These unfavorable hemodynamics are a result of the inverse of MCP occurring (elsewhere described as "stress resonance", "resonant pressures" or "inverse MCP"=iMCP), when increased peripheral pumping pressure is consistently generated at the heart at substantially the same time as maximal systolic pressure, making the heart work harder, while the lowest peripheral pumping pressures consistently coincide with diastole, decreasing myocardial perfusion pressures and oxygenation.

Therefore, the present disclosure is also related generally to methods and apparatus for improving cardiac health through avoiding hemodynamically unfavorable coordination of repetitive MSK movement and skeletal muscle contraction cycles with the cardiac pumping cycle during physical activity.

In addition to enabling reliable favorable coordination and avoiding persistent unfavorable coordination of the relative timing of MSK and CV hemodynamic pumping, the systems and methods of this disclosure can simultaneously provide guidance towards the achievement and maintenance of a specific level of CV exertion, while minimizing CV stress, during rhythmic physical activities.

In order to enable the user to achieve these ends during rhythmic physical activity, systems and methods monitor the CV pumping cycle. In alternative embodiments, monitoring can be achieved via at least one of: monitoring the user's electrocardiogram (ECG) and monitoring the user's peripheral arterial blood pressure, flow, or volume waves by any appropriate mechanism or process.

Ongoing algorithmic analysis of the heart's beat-to-beat timing is performed to identify the target timing of the user's MSK peripheral vascular pumping activities relative to elements of the CV pumping cycle, for example so as to enable an increase in myocardial perfusion during diastole and a decrease in systemic vascular resistance during systole. The user is accordingly prompted to time MSK activity to occur at regular time intervals that correspond to the targeted portion of the CV pumping cycle. In certain embodiments, the target for the initiation of maximal MSK pumping substantially approximates aortic valve closure in the heart near the end of systole, which occurs approximately at the end of the T-wave in the ECG (30 in FIG. 2A) and at the dicrotic notch (transition point) of an arterial pressure wave in the aorta (12 in FIG. 1A), although other target initiation times and/or frequencies are also contemplated. Aortic valve closure can also be targeted in IABP and ECP pump timing, due to the fact that it signals the time at which the central arterial pressure exceeds the ventricular pressure. Aortic valve closure also corresponds with the approximate time when arterial blood initiates maximal flow through the coronary arteries, which branch off the aorta just distal to the aortic valve. In another example, improved or maximal MSK pumping is targeted to synchronize with the arrival of the resulting propagating pressure waves at the heart with the proper diastolic point in the cardiac cycle that result in increased myocardial perfusion. MSK muscle contractions and/or movements can displace the local arterial and venous blood volumes, with the propagating intravascular pressure (equivalently, volume) waves traveling to the heart in a short period of time. Arrival of the resulting arterial pressure waves at the aorta during the period in time the heart muscle is relaxed can enhance blood flow to the coronary arteries and improve blood perfusion in the myocardium.

In some embodiments of the method and system, the user can be provided with an auditory, visual or tactile MSK activity prompt at a cadence that substantially matches the HR or, alternatively, a unitary fraction of the HR (e.g. ½, ⅓, or ¼, etc.), and at a targeted timing relationship relative to the cardiac pumping cycle, to guide the user to maximal MSK blood pumping. The targeted timing relationship can be derived from beat-to-beat timing analysis of input from cardiac sensors, or via analysis of the relative timing of the MSK pumping vs. cardiac pumping cycles derived from MSK and cardiac sensor signals.

Considering time delays due to wave propagation, and variations in physiology and exercise routines, the optimal timing of "maximal MSK pumping" (muscle contractions and inertial changes) can be time-shifted from the conventional definition of diastole. "Systolic" and "diastolic" pressures may be defined differently in different circumstances. For example, they can be measured in the aorta, or peripherally. Intravascular wave propagation and timing can be effected by several physiological variables, including arterial size, stiffness, distance from the Aortic Valve (systemic arterial outlet from the ventricle), vasoconstriction, pump contraction force, etc. As used herein, we assume a theoretical or empiric determination of "optimal" timing relative to the user's cardiac cycle as measured with an ECG. Other CV measures can be similarly used, including a whole body or peripherally observed plethysmogram, however, it will be appreciated that one skilled in the art will be able to introduce correction factors in the event that a time-delayed (e.g., peripheral vascular) measure is used.

The system can be configured to evaluate the user's MSK activity timing relative to the target timing by comparing data from MSK movement or muscle contraction cycle sensors (e.g., accelerometers, gyroscopes, EMG sensors, magnetic sensors, mechanical sensors, pressure sensors, cameras or electromagnetic wave based sensors) to that of CV sensors (e.g., ECG, Photoplethysmogram (PPG) or electronic auscultation). Many forms of sensors and ways of mounting same are contemplated herein, including direct skin mounting (e.g., by way of straps, adhesive), or via clothing, jewelry, mobile electronic devices, implants, and so on. The sensor devices can be separately housed and packaged from the processing and feedback devices or, alternatively, can be mounted, carried, or otherwise integrated with user feedback devices. The sensor devices and feedback devices can also be integrated into a single package or device. For activities that utilize stationary or non-stationary equipment (e.g. an exercise treadmill, elliptical, stepper or bicycle), timing of the user's MSK movements can be detected with comparable sensors to those mentioned above mounted to our integral within the equipment (e.g. magnetic, hall-effect, optical, magneto resistive, inductive, capacitive, rpm sensors, etc.)

In order to guide the timing of the user's activity, a prompt can be delivered to the user via one or more of an auditory, visual, tactile, electrical, or other appropriate recognizable cue. Prompts can be delivered from a variety of devices such as items worn by a user (e.g., wrist or headbands, headphones, ear buds, belts, straps, clothing, jewelry, speakers, etc.); items carried by a user (e.g., bags, mobile communication devices, mobile entertainment devices, mobile exercise devices); items internal to the user (e.g. subcutaneous sensors, intraoral auditory bone conduction devices, etc); or items external to the user (e.g. exercise machines, video gaming systems, etc).

Prompting devices can be comprised of a housing carrying circuitry, microprocessor(s), data storage, drivers, input/output mechanisms, power sources, and connectors. The devices can be removably mounted or permanently integrated with a carrying mechanism such as a strap, belt, adhesive patch, holder, article of clothing, etc. The devices can be removably or permanently integrated with the sensors, designed for single or multiuse. They can also be placed on or under the surface of the skin. Connectors, such as snaps or housings, for mounting the device can be used for data transmission, power charging, etc., in addition to anchoring the device.

In certain embodiments of methods and systems in this disclosure, the user's movement and timing can be mechanically assisted. In some embodiments, the user's movement, pressure generation, or body heat can be used as means to drive a power generator for the device and any accompanying energy storage component therein.

Optimal timing of a user's MSK activity, relative to their monitored heart rhythm, that results in improved cardiac pumping efficiency and favorable perfusion of myocardial and peripheral muscles, can differ from person-to-person, or depend on at least one of: when activity occurs; the conditions in which the activity occurs; the heart rates during the activity; the level of physical exertion during the activity; individual variations in anatomy; the type of movements they make; variations in the force of movement; and so on. Accordingly, the methods and systems of the current disclosure can be further configured to identify the user's optimal timing empirically based on the individual's current conditions and/or the nature of their movements. For example, a user's HR while exercising at a given work load may depend on the timing of their MSK pumping activity relative to the cardiac pumping cycle, with lower relative HR values associated with an improved pumping efficiency. This optimal timing can, for example, be found by guiding the user to time their MSK activity according to a prompt provided with varying timing relative to the cardiac pumping cycle, and then identifying the prompt (or measured MSK) timing associated with the more favorable (lowest) relative HR values at a given level of exercise. This identified "favorable" or "optimal" prompt timing or timings can be then be used subsequently. The system can temporarily switch back to the identifying or "calibration mode" periodically to ensure ongoing optimization of timing. Optimal timing can be assessed as described here using additional or alternative measures other than HR. For example, measures of oxygen consumption, cardiac output, work output, blood pressure, respiratory minute volume, temperature, or other measures of efficiency or energy expenditure could be used.

Further user feedback can be provided to enable the user to confirm or optimize the cadence, timing, and/or quality of MSK activity and to improve confidence that the desired parameters are being achieved. In addition, the device can be configured to repeatedly modify or otherwise adapt the prompt timing based on the user's response to the prompt, in order to effectively guide the user to further optimize MSK activity timing relative to the target timing. For example, if the user is detected to be moving at a relatively consistent amount of time before or after the target timing, the prompt can be adjusted automatically to occur later or earlier, respectively, to more properly align their detected movements to the targeted timing.

In addition, systems and methods can enable the user to evaluate their subjective experience of the exercise, comparing their experience of different prompt timings (e.g. ease of exercise) relative to the CC, in order to help identify and select "optimal" prompt timing. The user can alternatively be directed to use or can choose other means to personally identify and select target prompt timing.

Additional embodiments of the device can leverage pulse wave monitoring as the basis for evaluating at least one of the timing, quantity, and nature (e.g., quality) of MSK pumping activity.

A combination of monitoring and guidance also affords opportunities to include in the system and method personalized coaching and feedback via programmed coaching algorithms or via ongoing or intermittent professional evaluation, based on data obtained from one or more of the CV and MSK activity monitors employed by this system, to further optimize at least one of efficiency, safety, motivation, and health benefit from the physical activity.

In another embodiment of the system, proper timing of the feedback prompt relative to the cardiac pumping cycle is determined via a measure of the user's peripheral arterial blood pressure, flow, or volume wave (e.g., using a PPG), identifying the amplitude of the resulting pulsatile signals that corresponds to an improved pumping efficiency associated with, for example, a reduced relative HR or oxygen consumption.

In addition to timing, the nature or "quality of the musculoskeletal movement" (QMM) can impact the efficacy of MCP. For purposes of this discussion, QMM refers to factors, beyond simple movement timing, that can impact the efficacy of MCP. Factors include, but are not limited to, the specific skeletal muscle groups contracting; the sequence of movement or contraction or relaxation of specific skeletal muscle groups or MSK elements; the timing of movement or contraction or relaxation of specific skeletal muscle groups or MSK elements relative to one another; the force of skeletal muscle contraction; the speed and duration of movement or skeletal muscle contraction; the rate of acceleration and deceleration of specific body parts during specific movements; the position of the user during MSK movement and skeletal muscle contraction; the posture of the user during MSK movement or skeletal muscle contraction; and other factors that affect the ergonomics and kinetics of movement (e.g., heel strike vs. forefoot/midfoot strike during ambulation).

Among the various sensors for collecting data for input to the processing aspect disclosed herein, foot strike sensors can provide valuable data and biofeedback when used with the CV monitoring equipment also described herein. In alternative embodiments of a device and method of biofeedback during repetitive physical activity, foot strike biofeedback sensors can provide utility as stand-alone devices, independent of a CV monitoring system.

In addition to the variety of movement sensors described previously, simple pressure sensors can be placed adjacent to the user's foot in order to monitor the timing and quality of the foot strike during rhythmic physical activities such as running and walking. Pressure sensors integrated within the sole of the shoe or placed under or integrated within a shoe insert, sock or other foot worn accessory can be used to gain information into the timing of the foot strike.

Additionally or alternatively, one or more foot strike sensors can be used for each foot in order to monitor the timing and magnitude of foot strike across different parts of the foot anatomy. In certain embodiments, the user can be guided to initiate contact with the ground with a particular part of the foot's anatomy, for example, at least one of the forefoot, a portion of the forefoot, and the midfoot. Contacting the ground with the forefoot first ("forefoot strike") ensures contraction of the calf musculature (gastrocnemius) prior to the muscles of the thigh (e.g. hamstrings and quadriceps musculature), which can lead to more efficient pumping of blood from the lower extremities towards the heart than would occur with the heel striking the ground first ("heel strike" instead makes it likely that contraction of the thigh musculature will occur before contraction of the calf musculature, thereby preventing the calf musculature from pumping blood effectively towards the heart). Foot striking impacts on MSK pumping efficiency can be, in certain embodiments, observed by monitoring changes in blood pressure, flow or volume waves; changes in accelerometer signals, changes in other physiological signals, for example, HR. These impacts on the effectiveness of peripheral vascular pumping can potentially improve the impact of MCP, or worsen the impact of iMCP.

In certain embodiments, a pressure sensor is located vertically in the user's shoe, behind the heel (behind the calcaneus) of the user's foot, so that the mechanical sensor is only triggered when the heel strikes the ground substantially before the rest of the foot. By locating the pressure sensor in a substantially vertical position, behind the heel, the sensor can be configured to only be triggered when the user's foot strikes the ground prior to the rest of the foot, as typically occurs with heel strike. Alternatively or additionally, at least one pressure sensor can be located adjacent to the lateral foot, again in a substantially vertical position, in order to provide feedback on the timing and kinetics of lateral foot strike.

Also among the sensors for collecting data for input to the processing aspect disclosed herein, posture sensors can provide valuable biofeedback when used with the CV monitoring equipment described herein. In alternative embodiments of a device and method of biofeedback during rhythmic physical activity, posture biofeedback sensors can provide utility as stand-alone devices, independent of a CV monitoring system. Sensors that can provide posture information include some of the sensor technologies described previously, including accelerometers, gyroscopes, foot strike sensors, pressure sensors, emg sensors, cameras and further electromagnetic wave based sensors, force sensors, impact sensors, among others. These wired or wireless sensors can transmit location data, location relative to a fixed sensor, and information on location relative to one another, from important anatomic locations, including the shoulders, scapula, head, chin, neck, chest, ear(s), waist, back, and hip(s), among other locations. Because healthy posture leads to benefits independent of MCP, stand-alone posture monitors, utilizing these same technologies, for use during physical activity, may also be desired in certain embodiments of the device and method.

In certain embodiments of methods and systems in this disclosure, a wearable device such as a chest wall based sensor (e.g. on a strap, integrated with clothing, integrated with an adhesive patch, or subcutaneously based) can be configured to include sensors for detecting the user's ECG signals and movements. The sensed signals can be processed within the wearable device in real-time to determine timing of a feedback prompt according the methods described herein, or alternatively transmitted in a wired or wireless manner to an external receiving device that conducts the processing. The signal data transmitted for external processing can include the user's ECG waveform and signals indicative of movement (e.g., accelerometer signals) or, alternatively, can include one or more of a signal indicative of the ECG's R-wave events, timing, and R-R interval (RRI) timing; and movement timing. The receiving device can be a dedicated unit, or one that serves other purposes as well, such as a smart-phone, music player, radio, pedometer, GPS monitor, heart monitor, etc. The wearable device or the receiving device can utilize the wired or wireless data for use as input to an included software algorithm configured to determine timing prompts according the methods described elsewhere in the current disclosure, and drive an interface that communicates these prompts to the user (e.g., direct audible signal or to an earpiece, wireless transmission of an audible signal, visual cues, vibratory signals, etc.).

In other embodiments of methods and systems in this disclosure, a wearable device such as an ear mounted audible transmitter can be configured to include sensors for detecting the user's PPG signals and movements. The sensed raw unprocessed or pre-processed information can be further processed within the ear mounted wearable device to determine the proper timing and communicate the feedback prompt, and also can be transmitted in a wired or wireless manner to a receiving device that further processes the received data in real-time to determine timing of a feedback prompt according the methods described herein. The unprocessed data can include the user's PPG waveform and signals indicative of movement (e.g., accelerometer signals), while pre-processed information can include one or more of a signal indicative of the PPG's waveform timing, and waveform interval timing; and movement timing. The receiving device can be a dedicated unit, or one that serves other purposes as well, such as a smart-phone, music player, radio, pedometer, GPS monitor, heart monitor, etc. The wearable device or the receiving device can utilize the wired or wireless data as input to an included software algorithm configured to determine timing prompts according the methods described elsewhere in the current disclosure, and drive an interface that communicates these prompts to the user (e.g., direct audible signal, wireless transmission of an audible signal, visual cue, vibratory signal, etc.)

The above is a summary of a number of the unique aspects, features, and advantages of the present disclosure. However, this summary is not exhaustive. Thus, these and other aspects, features, and advantages of the present disclosure will become more apparent from the following detailed description and the appended drawings.

BRIEF DESCRIPTION OF THE DRAWINGS

In the drawings appended hereto like reference numerals denote like elements between the various drawings. While illustrative, the drawings are not drawn to scale. In the drawings:

FIGS. 1A, 1B, and 1C are graphs depicting exemplary arterial blood pressure, blood volume or blood flow curves for individuals at rest and during rhythmic MSK activity.

FIG. 2A is an example of a normal electrocardiograph tracing.

FIG. 2B is an illustration of exemplary timing relationships in an individual between an ECG tracing, a central arterial pressure waveform, a peripheral arterial waveform, and skeletal muscle contraction cycles.

FIG. 5 is a chart illustrating how several physiological and activity-related factors can be combined to establish a "target rate" that in turn can be used to define the user's respective coordinated target HR, MSK activity rate or cadence, and respiration rate according to the present disclosure.

FIGS. 6A and 6B are flow charts illustrating the looping cycle of sensing the user's cardiovascular (CV) cycle and providing prompts coordinated with this CC according to the present disclosure.

FIGS. 32A-H are illustrations of exemplary wearable locations for physiological sensors located against, near, or beneath the surface of the skin of a user, including chest locations (exemplary integration with a strap; clothing; an adhesive patch, or a subcutaneous implant); and arm, wrist, or finger locations, respectively, according to various embodiments of the present disclosure.

FIGS. 33A-F are illustrations of various embodiments of head-mounted sensors and, in certain embodiments, feedback devices, according to the present disclosure.

DETAILED DESCRIPTION

Figure 2C:
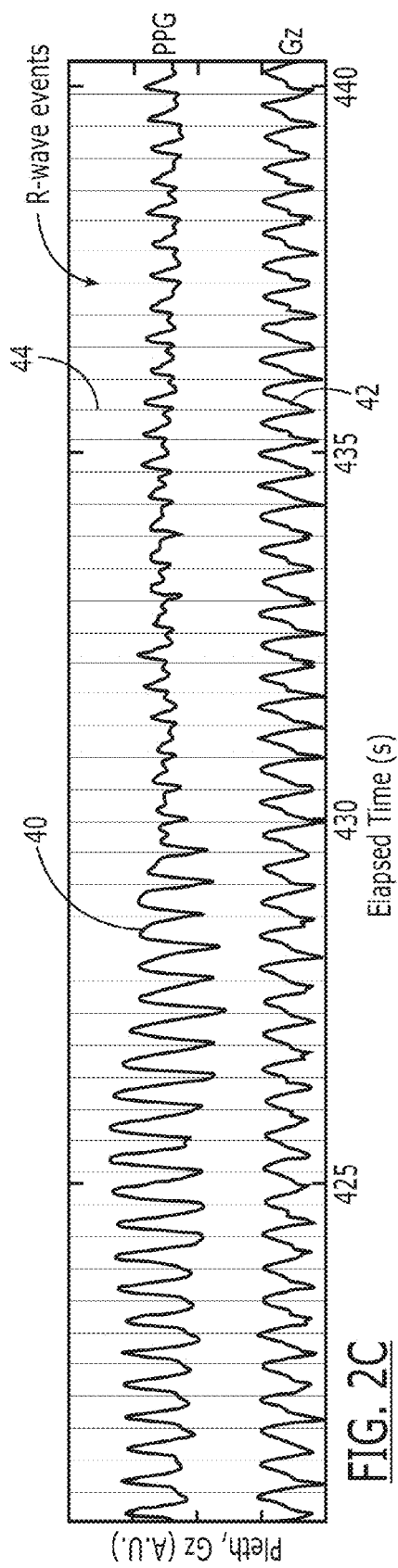
FIG. 2C is an exemplary comparison of timing events in an individual during exercise (running in this example), illustrating the relative timing of a PPG tracing, R waves, and accelerometer tracings that are representations of MSK inertial movements.

We initially point out that description of well-known starting materials, processing techniques, components, equipment and other well-known details may merely be summarized or are omitted so as not to unnecessarily obscure the details of the present disclosure. Thus, where details are otherwise well known, we leave it to the application of the present disclosure to suggest or dictate choices relating to those details.

The system described in this disclosure includes a biofeedback device that enables the user to optimize muscular contraction and MSK movement during rhythmic physical activities (such as aerobic exercise, dance, rhythmic isometric or isotonic resistance exercise, biking, rowing, swimming, running, jogging, hiking, or walking) in order to synchronize the peripheral vascular pumping cycle with the heart's pumping cycle and selectively achieve MSK counterpulsation (MCP).

Important central hemodynamic effects of MCP can be illustrated by comparing an exemplary central arterial blood pressure curve of a healthy young individual at rest (FIG. 1A) to exemplary central arterial blood pressure curves of the same individual during physical activity (FIGS. 1B and 1C). FIG. 1A, representative of pressures in a typical healthy young elastic aorta when the individual is at rest, shows a systolic pressure wave 10, which ends at aortic valve closure (dicrotic notch 12), and is followed by a diastolic wave 14. FIG. 1B depicts an exemplary central arterial blood pressure in the same healthy young individual when cardiac systole 11 (heart pumps blood to into the aorta) occurs at the same time as maximal pumping of blood towards the heart by the MSK system, causing the cardiac and MSK pumping mechanisms to temporarily directly oppose the action of one another, as the two pumps simultaneously push blood in opposite directions, towards one another, within the same central arteries. This can lead to multiple undesirable effects, including any or all of: decreased pumping efficiency, increased systolic blood pressure (e.g., 16 in FIG. 1B), increased HR, increased myocardial oxygen consumption, and earlier fatigue, which can lead to increases in health risk, particularly in extreme or at risk circumstances, due to the possibility of inadequate myocardial perfusion concurrent with an increased myocardial work load. The detrimental effect can be made worse when the unfavorably coordinated pumping results in lower central arterial and venous pressure during diastole, potentially decreasing both myocardial perfusion and filling of the hearts pumping chambers.

Alternatively, FIG. 1C depicts a more hemodynamically favorable exemplary central arterial pressure when maximal MSK pumping during cardiac diastole 13 increases the diastolic central blood pressure 20, and maximal MSK relaxation during cardiac systole 11 decreases systolic central blood pressure 18.

FIG. 1B, as described, depicts a typical central pressure wave in a young individual during unfavorable MSK pump timing. Alternatively, FIG. 1B also illustrates representative characteristics of a central arterial (e.g., aortic) waveform that one might expect to see in an elderly individual at rest. Contrary to the healthy young individual at rest, as depicted in FIG. 1A, as individuals age, the aorta loses its elasticity, leading to a classic increase in baseline systolic blood pressure 16, since the heart is pumping blood into a stiffer tube (aorta), and a decrease in diastolic blood pressure, because the stiff aorta is less able to maintain pressure without the heart actively generating pressure, as it does during systole.

FIG. 2A illustrates some of the important waves in a typical ECG tracing 22, including the R wave 24, which is the most easily identifiable wave in the QRS complex in many ECG leads, and which represents depolarization of the myocardium of the ventricular walls of the heart. These R waves 24 are frequently utilized in the measurement of heart rate via the measurement of the duration of R-to-R intervals 26 (RR intervals, or RRI). The RRI can vary, particularly with respiration, in many people, and measurement of that variation is called heart rate variability (HRV). In fact, HRV, which tends to decrease during exercise and stress, has also been used as an indicator of mental and physical stress and relaxation. The T wave 28 reflects ventricular repolarization, with end T wave 30 often used as a marker of the approximate timing of aortic valve closure during the hearts pumping cycle. End T wave 30 and aortic valve closure also both occur with timing that corresponds to the dicrotic notch 12 of a central arterial pressure wave.

FIG. 2B illustrates the timing of a typical ECG signal 22 when compared to the timing of the associated central arterial pressure (aortic pressure waves 32) and exemplary peripheral arterial pressure 34 in the same individual. This comparison highlights that, according to the methods and systems of the present disclosure, target MSK timing (two examples shown as 36 and 37) can impact the timing and morphology of arterial blood pressure, volume and flow at different physical locations in the circulation. For example, if MSK activity is timed to increase central arterial blood pressure during early diastole, the increase in localized arterial blood pressure may appear during the systolic portion of the peripheral waveform (e.g., at the arm, leg, or forehead). This phenomenon is due the fact that it takes time for pressure waves to propagate from their source, and the waves generated by the heart's pumping propagate from central to peripheral. Therefore, there is a correlation between the timing delay and the distance from the heart that the waveform is measured. Other factors can also influence timing delays, including vascular attributes (e.g., arterial stiffness, size, vasoconstriction or vasodilation), inertia during movement, and cardiac effects (e.g., contractility, stroke volume, etc.) FIG. 2B also shows two examples of targeted MSK timing 36 and 37, both comprising brief periods of skeletal muscle contraction during central diastole 13 followed by periods of relaxation. In 36, muscle contractions are timed by the user to begin at prompts 35 that repeat with each instance of the CC (MSK:CC=1:1); while in sequence 37, the prompts and muscle contractions repeat with every other CC (1:2). Scale 38 provides a graphical representation of the percent of the R-to-R interval 26 nomenclature used herein. For example, 0% and 100% represent events timed coincident with the R-waves 24, while 25% of the RRI is a quarter of the way between successive R-waves 24, and 50% is the mid-point between R-waves 24. Scale 38 of the R-R interval can alternatively be expressed fractionally as a value from zero to one, in units of degrees between zero and 360 degrees, or in radians between zero and 2π radians (e.g., 25%=0.25=90 degrees=1.57 radians), equivalent to the percentage terminology. Values greater than 100% describe events in a subsequent R-R interval (e.g., 130% represents a 30% location in the following interval).

FIG. 2C illustrates measured values from a user running on a treadmill, that show that the blood volume and pressure tracing 40, as measured by peripheral PPG at the forehead, is profoundly affected by the study subject's step timing (shown as measured via an accelerometer tracing 42) relative to a cardiac cycle timing event (designated here by R-wave event markers 44). These types of oscillations in arterial blood volume and pressure occur when the MSK activity cadence is slightly different than the HR. For example, a running cadence of 162 steps per minute and a HR of 160 beats per minute would result in an individual stepping slightly earlier (by approximately 1/80 of the RR interval) in the heart's cycle with each step. The relative contribution of peripheral vascular pumping due to MSK activity can be identified by measuring either the relative sizes of systolic versus diastolic waves, or in measuring variations in pulse pressure, as is most easily seen in FIG. 2C. Note that when the peak accelerometer signal 42 aligns closely with the R-wave events 44, PPG 40 amplitude is much greater than when the peak accelerometer signal occurs between R-wave events.

Figure 2D:
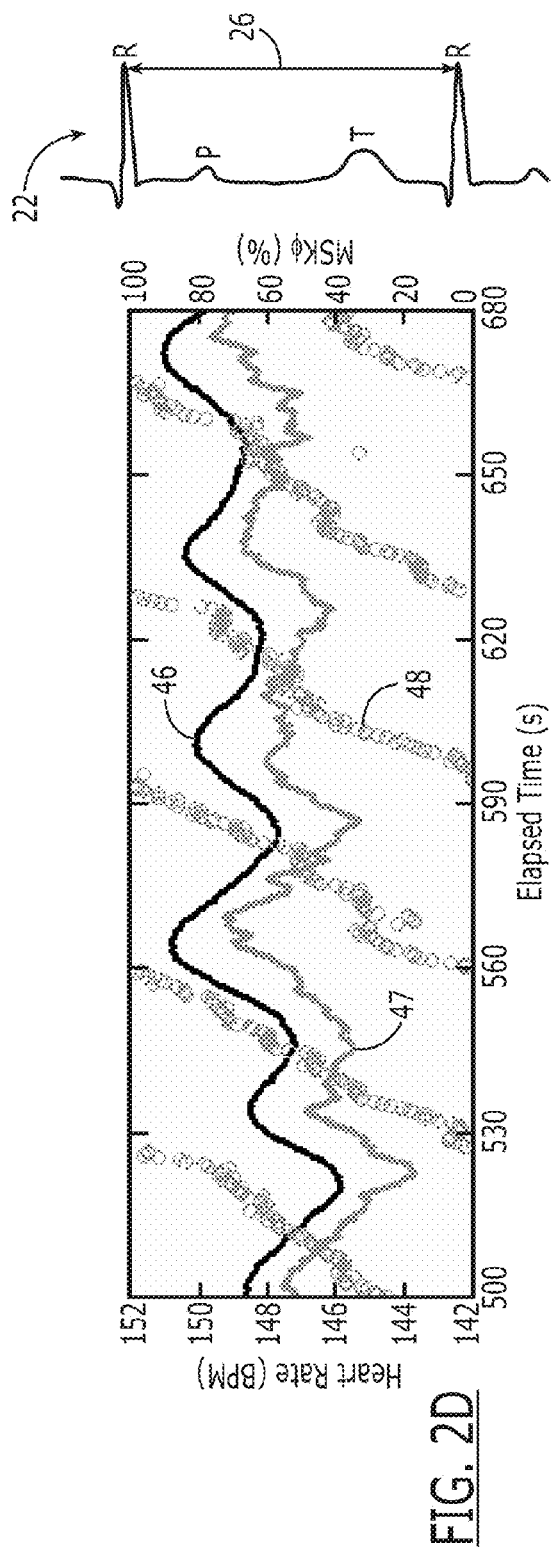
FIGS. 2D, 2E and 2F are exemplary graphs showing the influence of varying $MSK_\phi$ on a user's HR.

FIG. 2D shows a plot of measured HR 46 and step rate 47 of a user running on a treadmill, pacing the timing of their steps to audible prompts provided at a rate of approximately 2 per minute less than their average HR (i.e., prompt rate≈(HR−2)/min). The illustration demonstrates that the HR 46 can be seen to increase and decrease in a consistent manner, dependent on MSK activity timing relative to the user's cardiac cycle 48 (MSK$_\phi$), spanning the full phase range of 0-100% of the RRI per the scale 38 (FIG. 2B) approximately twice per minute. An exemplary ECG signal 22 with RR interval 26 is shown to the right of the graph, where time elapses from the bottom to the top.

Figure 2E:
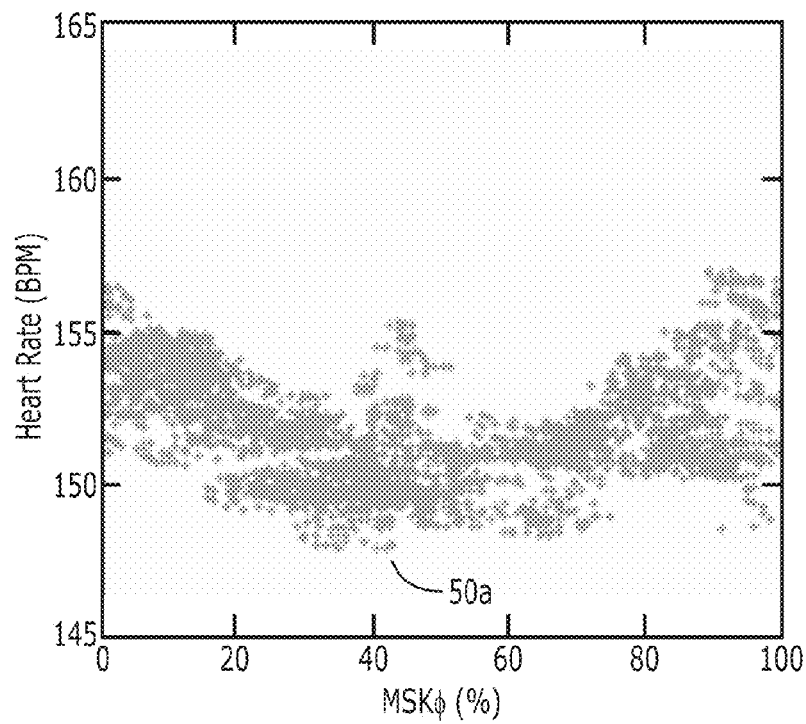
Figure 2F:
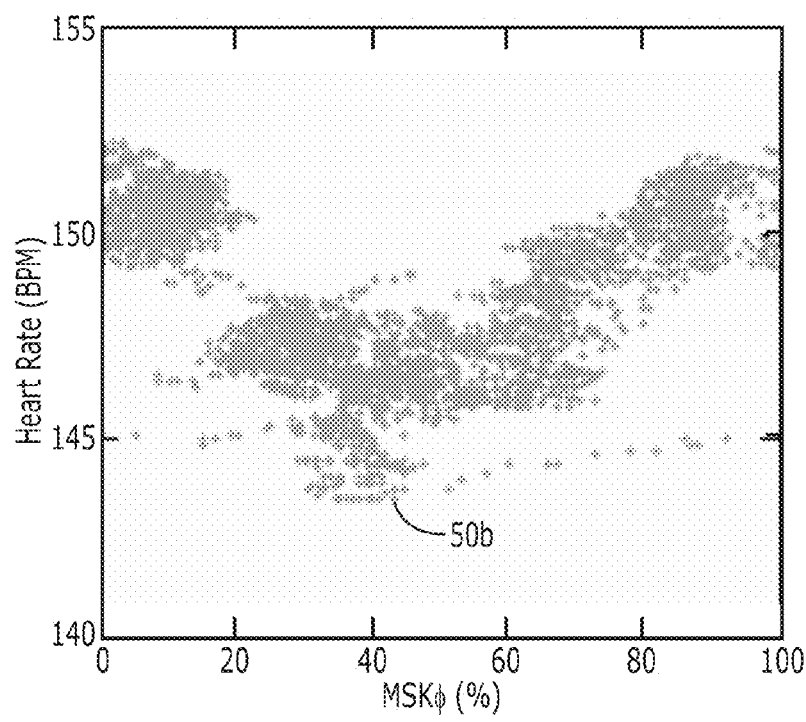

FIGS. 2E and 2F present graphs of data from two different individuals while they were running on a treadmill. The individuals were instructed to coordinate their stepping to coincide with audible prompts that were made to vary in phase with respect to their monitored ECG signals in a step-wise manner across the full % RRI span. Shown are plots of their respective heart rates versus the measured phases of their movements relative to their cardiac cycles (MSK$_\phi$, shown in equivalent percent units as the % RRI). As can be seen, their respective heart rates both reach substantial minima 50*a* and 50*b* at approximately 40% of their RRI.

As used herein, the term "synchronized" is meant to describe a state in which the user's MSK activity is coordinated to occur with a rhythm closely related to the rhythm of the cardiac cycle and a generally constant phase or timing relative to the heartbeat. The user's peak MSK activity may not occur simultaneously with a particular marker of the cardiac cycle (such as the R-wave 24 of the user's ECG 22, as depicted in the examples in FIG. 2) to be considered "synchronous"; rather the relative timing of the two events will occur in a generally constant manner, such as generally in relationship to a particular phase or event within the heart's pumping cycle. Synchronization can be achieved when the cardiac rate is an integer multiple of the MSK activity rate (i.e., CC:MSK=1:1, 2:1, 3:1, 4:1, etc.), as long as the timing relationship remains approximately constant relative to the particular marker of the CCs in which the MSK activity occurs. An example of this is shown by sequence 37 in FIG. 2B where prompts 35 occur with every other heart cycle, targeting MSK contractions in each case to be closely synchronized with early diastole.

A basic looping system used for synchronizing the user's CV and MSK pumping cycles, as described in the present disclosure, is shown functionally in FIG. 6A. In a first step 52, the user's CC is monitored, and in a second step 54, feedback prompts coordinated with their CC are provided to assist the user in timing their MSK activity.

FIG. 6B provides an example of a simple method for implementing such a feedback loop. In the first step 56, an instance of a specific aspect of the user's CC representing the repetitive timing of the user's cardiac cycle ($CC_t$) is identified using, for example, the timing of the R-waves in their ECG signal, or in another example, the timing of each systolic rise in pressure as sensed using a PPG signal (or in another example, the signal indicative of nadir of the diastolic cardiovascular pressure). The difference in time between two successive instances of $CC_t$ (e.g., the R-R interval) provides a measure of one cardiac cycle's duration. An offset, or delay time (τ) is computed in a second step 58, which can comprise, for example, a fixed value based on the user's activity and target HR, such as 140 ms—a value that represents a 35% phase lag when the user's HR is 150 BPM. In another example, the delay time τ can represent a percentage of the R-R interval, a target timing location that varies based on the user's HR computed as a function of $CC_t$ (which can vary over time), namely τ=φ×60/aHR, where φ represents a target phase at a fixed percentage of the RRI and aHR is the user's average HR computed from the recent successive values of $CC_t$ (e.g., R-R intervals). The aHR can, for example, equal the average of the last six beat-to-beat HR values, or in another example, the average of the last 10 beat-to-beat HR values. Finally, in a third step 60, feedback prompts are provided as a timing indication to assist the user in timing their MSK activity. These recurrent prompts are, in this example, delayed in time from $CC_t$ by the computed value τ. If prompts are provided with every CC, the resulting prompt rate is substantially equivalent to the user's aHR, delayed in time relative to $CC_t$ by the value of τ. For the configuration where the target timing is a particular percent of the RRI as described above, the delay value automatically adaptively adjusts (adaptively adjusting timing) in response to changes in the timing of the user's CC (i.e., in response to a change in the timing of the cardiovascular cycle) as the process repeats continuously by looping back to the first step 56. In an alternative embodiment, this adjustment can comprise a user-selected, time based offset in response to changes in the timing of their CC.

Figure 3A:
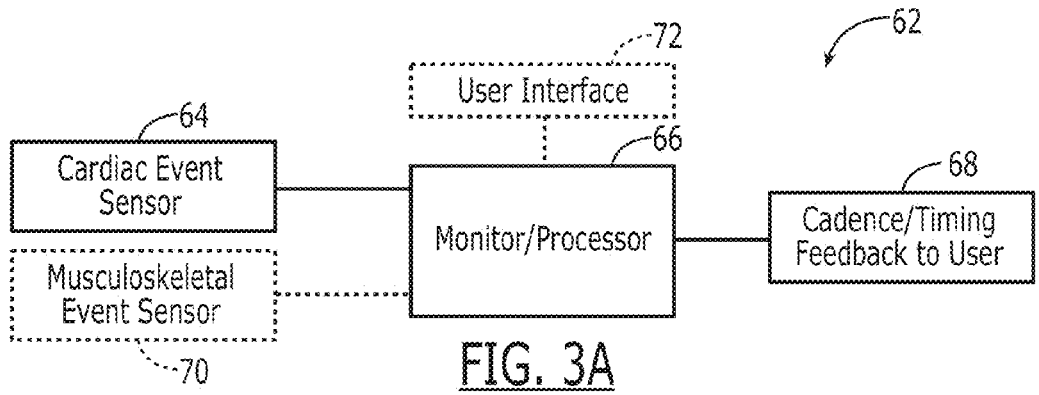
FIG. 3A is a block diagram illustrating use of a cardiac event sensor to identify the precise timing of the heart's pump cycle, processing these values to determine the targeted timing for the user's rhythmic MSK activity according to an embodiment of the present disclosure.

FIG. 3A illustrates a system embodiment of the present disclosure. System 62 comprises a cardiac event sensor 64 connected to monitor/processor 66 that is used for interpreting the cardiac signals and determining the cardiac cycle timing. Monitor/processor 66 uses this information to determine the proper cadence and timing feedback information 68 provided to the user for coordinating their MSK activity. The system 62 depicted in FIG. 3A can, optionally, further include a MSK event sensor 70 used by monitor/processor 66 to measure the relative timing of the user's activity, and a user interface 72 to receive information from the user and/or provide further information to the user. (In general, elements shown in dashed outline represent optional elements in the specific embodiment in which they are shown.)

Cardiac event sensor 64 can comprise one or more of an ECG, PPG, or any device that measures cardiac-induced blood volume, pressure or flow changes. (In each case, it is understood that the event sensor comprises the appropriate probe/transducer and associated electronics). In certain embodiments, sensor 64 measures the user's ECG signals used to identify the precise timing of the heart's R waves which would then be used in processor 66 to calculate the targeted timing for the user's MSK pumping activity. For example, in some embodiments, the R-to-R 26 timing interval can be utilized to calculate an estimate of the HR and of the timing of the end of the T-Wave 30 (end T-wave can provide an approximation of the timing of aortic valve closure in early diastole) relative to each R wave 24, as depicted in FIG. 2A. In other embodiments, the end T-wave 30 can be measured directly via the ECG signal 22. In further embodiments of system 62, the targeted time for the user's movements can be calculated to occur at a different location within the R-R interval 38 (FIG. 2B). In additional embodiments, this targeted percentage of the R-R interval (RRI) can vary as a function of the user's HR. In yet additional embodiments, the dicrotic notch of the monitored arterial pressure or flow wave (e.g., via PPG sensor) can be used in order to estimate of the timing of aortic valve closure, or an alternative marker of the cardiac cycle such as the onset of systole can be used. In additional embodiments, measurements of the efficacy of MCP, for example, MCP effect on measured HR or blood pressure waves at a given work output, can be analyzed by the system to target improved or optimal timing for MSK movement parameters.

Cadence/timing feedback to the user 68 can comprise one or more of an audible, visual and tactile indication. For example, the feedback 68 can be provided in the form of a metronome that provides a sound at the proper rhythm and timing relative to their cardiac cycle for the user to optimally coordinate their movements and improve MCP. Additionally or alternatively, for example, the feedback 68 can comprise a visual graphic display that guides the user to adjust the cadence and/or and timing of their activity.

In certain embodiments of the method and system, the system shown in FIG. 3A further includes a MSK event sensor 70 that monitors the user's movements. Sensor 70 may comprise accelerometer(s); gyroscope(s); mechanical or solid state pedometer; magnetic switches; proximity, acoustic, optical, or pressure sensors; camera(s) or other electromagnetic wave based sensors; direct measures of muscle activity (e.g., EMG, stretch); or other MSK activity sensors well known to practitioners of the art. In order to characterize the relationship of this movement relative to the targeted timing in the heart's pumping cycle, the sensor data 70 is interpreted via algorithms contained within processor 66 that estimate the timing of at least one of targeted skeletal muscle contraction and skeletal muscle relaxation and targeted MSK movement during each peripheral vascular pumping cycle (as measured with cardiac event sensor 64). Using this data, the device can be programmed to modify the feedback to the user 68 to enable the user to more precisely synchronize peripheral vascular pumping to the specific targeted portions of the cardiac pumping cycle.

Figure 3B:
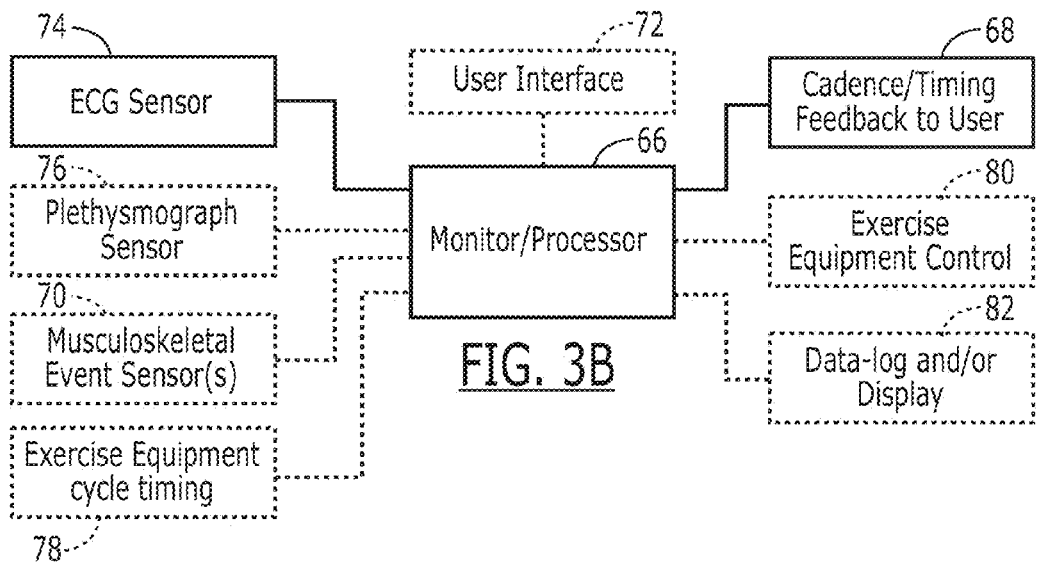
FIG. 3B is a block diagram illustrating use of various sensor signals to identify the precise timing of the heart's pump cycle, processing these values to determine a targeted timing for the user's MSK movement and skeletal muscle pumping cycles, and providing feedback directly to a user as well as via various equipment and displays relating to the timing/wave coordination according to an embodiment of the present disclosure.

FIG. 3B illustrates another system according to an embodiment of the present disclosure. ECG sensor 74 and/or optional PPG sensor 76 can be used for sensing the user's cardiac cycle rhythm and timing, while optional MSK event sensor 70 and/or exercise equipment timing sensor 78 can be used to sense the timing of the user's MSK activity. PPG sensor 76 can further be used for sensing the effects of the user's activity on their blood pressure waveform as depicted in FIGS. 1 and 2C. Monitor/processor 66 uses this received information from the available sensors to determine the proper cadence and timing feedback information 68 provided to the user for coordinating their MSK activity according to the current disclosure. Monitor/processor 66 can optionally further provide controlling information 80 to exercise equipment for further facilitating the user in maintaining their targeted activity cadence. For example, if the user's HR rises or falls below a target value when using a treadmill, the incline of the treadmill can be decreased or increased, respectively to assist in returning the HR to the target range. In another example, control 80 can be used to increase and decrease the treadmill speed to better match an increased or decreased cadence, respectively, as the user's HR changes during use. In both of these examples, maintaining the HR and, accordingly, MSK activity cadence within a target range can help the user in properly coordinating their CV and MSK pumping cycles. Optional user interface 72 can be used to receive information from the user and/or provide further information to the user. Optional data-log 82 can be used for recording the various signal data and/or processed information from monitor/processor 66 for later analysis and/or display. Optional exercise equipment cycle timing sensor 78 can comprise a crank location sensor used with a stationary or non-stationary bicycle, force and/or pressure sensors, strain sensors, rotary position sensor, or other sensor that can provide information regarding speed, cadence and cycling position.

Figure 4:
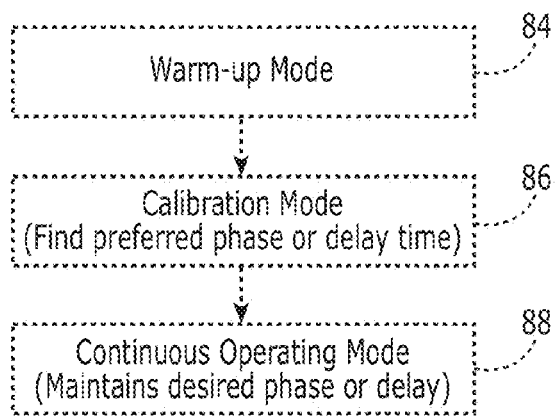
FIG. 4 is a flow chart illustrating an example of three operational steps, namely a warm-up mode, calibration mode, and continuous operating mode that can be combined in a system according to an embodiment of the present disclosure.

FIG. 4 illustrates an example of combining three operational steps according to an embodiment of the present disclosure. In this example, a system can monitor and/or direct a user during a warm-up mode 84, followed by a calibration mode 86, and then a continuous operating mode 88. The warm-up mode 88 is used to monitor and optionally provide information to assist the user in increasing or decreasing their average HR to a target range (note: for brevity, the term "warm-up mode" is used in this disclosure to represent embodiments of the method and system that enable the user to increase, as well as embodiments that enable a user to decrease HR to a target HR, as indicated, even though the terminology "cool-down mode" is a better descriptor for a mode that enables a user to decrease HR.) In this embodiment, once the user's HR falls within a target range, the system can transition into a calibration mode 86 that guides the user to vary the relationship between their MSK activity and cardiac cycle according to a pre-defined scheme. The system uses the measured data obtained during the calibration mode 86 for identifying empirically an improved or optimal timing and/or phasing value(s) between their activity and cardiac cycle that results in improved cardiac efficiency (e.g., a reduced HR, a reduced systolic blood pressure or a reduced pulse pressure at an otherwise equivalent level of work output). This improved or optimal timing or phase is then used as the target timing or phase provided to the user during the following continuous operating mode 88.

FIG. 4 exhibits that one or more of these three steps are optional, as a system according to another embodiment of the current disclosure can bypass the warm-up mode 84 and progress into calibration 86 and continuous operating 88 modes directly. Alternatively, a system can include warm-up 84 and continuous 88 modes without the need for identifying the user's optimal activity timing, useful, for example, if this timing had been evaluated previously, or generic or population-wide default timing is used. In yet another embodiment, the system can be configured to include only the continuous operating mode 88 without explicitly including a warm-up 84 (e.g., during exercises in which targeted phasing can be initiated at the onset) or a calibration mode 86.

FIG. 5 illustrates that algorithms according to the current disclosure can utilize different multiple targeted rates at different times in guiding a user to achieve MCP, including, for example target HRs 90, target respiratory rates 94, and target MSK activity cadences 92. Many factors 97 can contribute to identifying an overall "target rate" 96, from which the associated target HR (tHR) 90, MSK cadence 92 and respiratory rate 94 can be identified. The relevant factors 97 can include but are not limited to: population data 98, personal physiologic data (physiologic attributes of the user) 100, (e.g. age, height, weight, fitness, etc), the specific physical activity involved 102, stored or sensed information on performance goals (e.g. endurance training, warm-up, cool-down, training, racing, etc.) 104, personal preferred (and/or maximum) HR 106 and MSK cadence 108, personal exercise history, individual competition, etc. In one example, for an individual involved in running, factors 97 can result in a specific target rate 96 of 160 per minute, a tHR 90 of 160 BPM, and target MSK cadence 92 of 160 steps per minute. These matched CC and MSK activity rates, combined with the user's proper coordination of their relative timing, can result in the user achieving MCP. In another example for a similar individual involved in rowing, the same value of target rate 96 can lead to an equivalent tHR 90 of 160 BPM, but an MSK cadence 92 of 32 strokes per minute—a one-to-five ratio; the timed strokes occurring on every fifth heart beat can also provide benefit, achieving MCP during those heart beats. The targeted MSK rates can further influence the user's targeted speed and/or targeted settings of exercise equipment used.

The optimal timing relationship between a user's MSK and CV pumping cycles for achieving MCP may differ among individuals and/or their activities. For example, repetitive movements involved with running and rowing differ in both the muscle groups involved and inertial blood-redistribution effects. As a result, the maximal point in the MSK pumping cycle may occur at a different point within the user's movement cycle, suggesting that, in general, the optimal timing relationship for achieving MCP can be dependent on the type of rhythmic musculoskeletal activity involved. Individual users may also interpret the pacing prompts differently from one another, resulting in their moving at different relative times independent of the activity involved. These user- and/or activity-dependent differences can be accommodated by identifying the preferred relative timing relationship empirically in a calibration process as identified by 86 in FIG. 4.

Figure 8A:
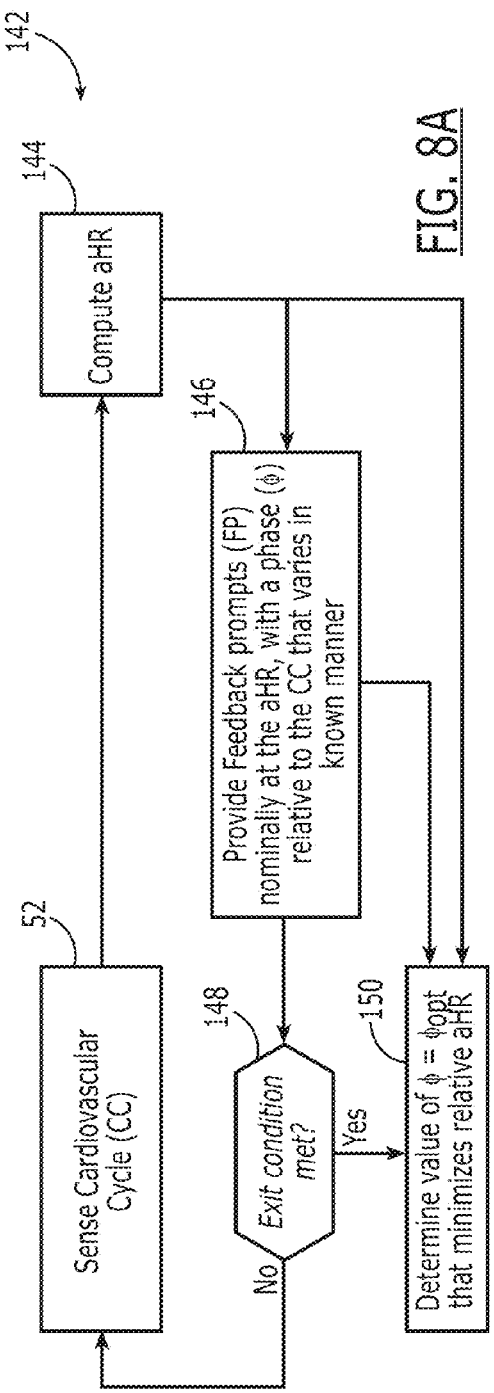
FIGS. 8A and 8B are flow charts illustrating exemplary calibration mode feedback loops useful for determining a delay value between the user's repetitive activity with respect to their CV pumping cycle that results in a reduced HR according to an embodiment of the present disclosure.

An example of this calibration process is shown in FIG. 8A, in this case using only measures of the user's cardiac cycle. Process 142 starts by sensing the user's CV pumping cycle (CC) 52, from which their average heart rate (aHR) 144 is computed. Feedback prompts 146 are provided to the user for timing the cadence of their activity. These prompts 146, while occurring at a rate nominally equal to their aHR 144, are made to vary in a known and/or predicable phase relative to the CC 52. For example, the prompts can be variably time-shifted from the measured cardiac cycle 52; in another example, the prompts can be provided at a rate of aHR−1 BPM (i.e., one beat per minute less than the heart rate). In both of these examples, the relative phase between the feedback prompts 146 and user's sensed cardiac cycle 52 are determined. The user paces their activity according to the prompts, preferably at a nominally stable work output level (e.g., constant speed and incline while running on a treadmill), while the system accumulates paired data comprising the prompt phases ($\phi$) 146 and the user's aHR 144. This process is maintained for sufficient time so as to cycle the user through numerous phases. Once this exit condition 148 is attained, the preferred phase value ($\phi_{opt}$) 150 associated with the minimum relative HR is determined using the paired data from 144 and 146. In this example calibration process, a phase-dependent reduced HR observed with an otherwise equivalent work output level reflects the improved exercise efficiency obtained when the user favorably times their MSK activity with their cardiac cycle. While 150 minimizes the relative aHR in this example, alternative embodiments can identify a relative minimum in a measured systolic blood pressure or pulse pressure, or use other physiologic measures indicative of increased cardiac efficiency.

Figure 8B:
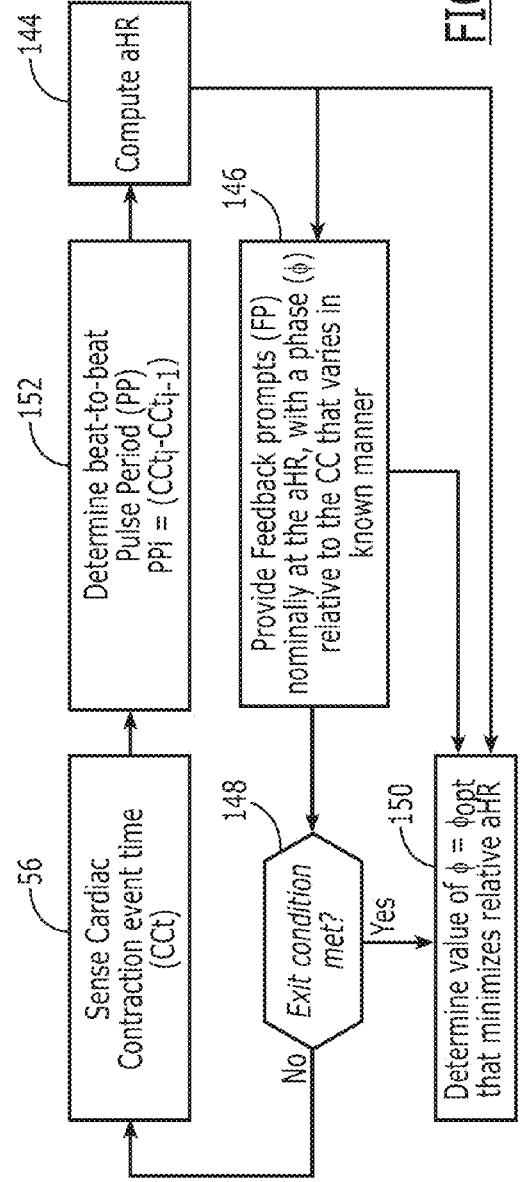

FIG. 8B illustrates a more specific example of a calibration process according to the current disclosure. In this example, the timing of a particular event within each cardiac cycle 56 is sensed, for example the R-wave of the user's ECG signal, or in another example, the systolic blood pressure rise within the user's measured PPG signal. This event timing ($CC_t$) identified in 56 is used to compute a beat-to-beat pulse period 152, from which an average heart rate value (aHR) is determined 144. The timing of feedback prompts 146 are variably delayed from each sensed event time $CCt_i$ according to $FP_i = CCt_i + \tau_i$, where $FP_i$ represents the $i^{th}$ time of the feedback prompt and $\tau_i$ represents the $i^{th}$ time delay from the $i^{th}$ cardiac event time. The delay time can be calculated as $\phi_i \times PP_i$, where $PP_i$ is the $i^{th}$ pulse period as determined in 152, and $\phi$ is made to vary in a known manner, such as a value spanning a range of zero to one, smoothly changing over a period of one minute; or in another example, in a uniform or, alternatively, random step-wise fashion spanning values of zero to one in steps of 0.1 (i.e., 10%) that change once every 20 seconds. This process repeats until exit condition 148 is met, after which the value of optimum $\phi$ (=$\phi_{opt}$) from 146 associated with a most consistently reduced or minimum relative aHR from 144 is determined (150). The exit condition 148 can comprise, as an example, completing two complete cycles through the phases. Alternatively, exit condition 148 can be met when the accumulated data converges to an identifiable optimum phase $\phi_{opt}$ within a pre-determined tolerance.

Figure 7:
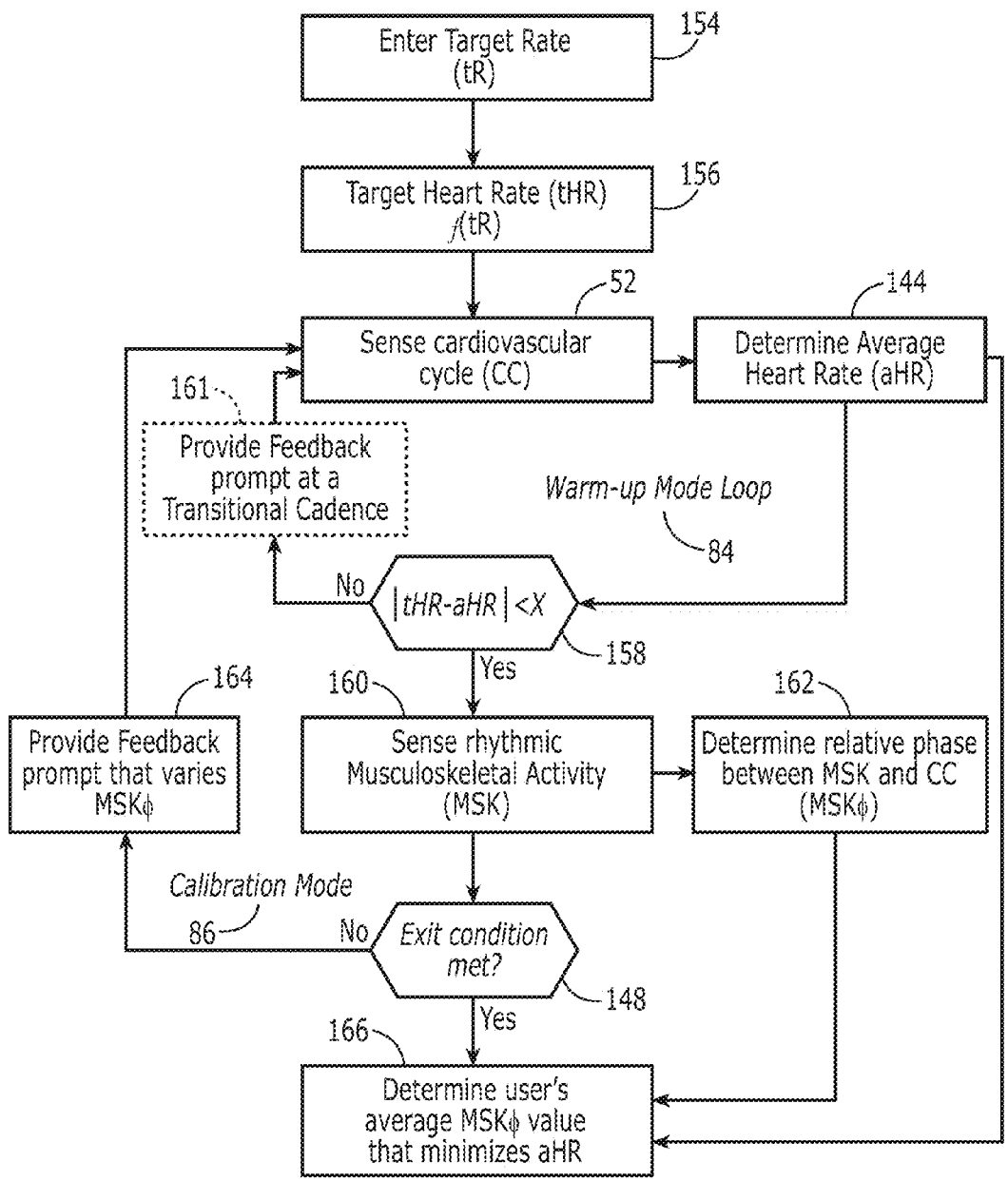
FIG. 7 is a flow chart showing an example of a calibration mode for an apparatus and method for coordinating cardiac pumping cycle and MSK movement according to an embodiment of the present disclosure.

Another example of a calibration mode configuration according to the present disclosure is shown in FIG. 7. The process begins by entering a target rate (tR) 154, from which a target heart rate (tHR) and heart rate tolerance (X) are computed 156 (e.g., using the process of FIG. 5). The process loop starts with sensing the user's CV cycle 52, obtained, for example, from an ECG signal or, alternatively, a PPG signal, from which the aHR is determined 144. If the aHR differs from the tHR by more than X BPM (e.g., the rates differ by more than 8 BPM or alternatively, 3 BPM), the user is optionally provided with feedback pacing prompts 161 at a transitional cadence to assist the user in reaching the tHR. This portion of the looping process comprises a warm-up mode 84. Once the rates differ by less than X, a calibration mode loop 86 is entered. This loop continues with sensing the user's musculoskeletal activity (MSK) 160 and determining the relative phase between their MSK and CC signals ($MSK_\phi$) 162. The user is provided with feedback prompts 164 that result in varying values of $MSK_\phi$. For example, 164 can create stepwise fixed phases relative to the user's CC (e.g., 10%, 20%, ..., 100% of the RRI), guiding the user to short periods of time (e.g. 20 seconds) in each phase. Further examples of prompts 164 that can be used to vary the user's $MSK_\phi$ include prompting at a rate of (HR−1 BPM); (HR+1 BPM); (aHR+1 BPM); (aHR−1 BPM); (HR−2 BPM); etc., where HR represents an instantaneous rather than average heart rate. The user paces their activity cadence according to the prompts, preferably at a nominally stable work output level (e.g., constant speed and incline while running on a treadmill), while the system accumulates paired data comprising the measured values of $MSK_\phi$ 162 and the user's aHR 144. This process is maintained for sufficient time so as to cycle the user through numerous phases spanning all or a portion of the possible range. Once such an exit condition 148 is attained, the accumulated paired $MSK_\phi$ 162 and aHR 144 data are used to identify the optimal $MSK_\phi$ value (or $MSK_\phi$ range) 166 associated with a substantially minimum relative aHR.

Because the user's $MSK_\phi$ is measured directly, the configuration shown in FIG. 7 can function when the user's cadence or phase does not match the provided feedback prompts. In an alternative configuration, the calibration mode can be designed to identify optimal MSK timing when a user is engaged in unprompted baseline physical activity (i.e., feedback prompts 164 are eliminated), since their $MSK_\phi$ is measured directly.

The relative timing and/or phase of the MSK and CC signals can be determined in 162 (and comparable steps in the other examples provided in the current disclosure) using event-based computations or, alternatively, by evaluating a span of signals in their entirety without identifying specific features within them. For example, an event-based approach using an ECG signal for monitoring the user's CC 52 can be configured to identify the specific timing of successive R-waves ($CC_t$, referring to a timing event within the CC), and an accelerometer signal for monitoring MSK 160 can target the timing of local peaks or, alternatively, another selected recurrent component of the user's rhythmic musculoskeletal activity ($MSK_t$). The instantaneous MSK "phase", i.e., the timing location of the sensed $MSK_t$ relative to the CC, can then be computed as $$MSK_\phi = (MSK_t - CC_{t-1})/(CC_t - CC_{t-1}),$$

where the subscripts t and t−1 refer to the associated times of the CC and MSK events and previous event, respectively; and the MSK event occurs within the considered R-R interval (i.e., $CC_{t-1} \leq MSK_t < CC_t$). When $MSK_\phi$ is calculated as shown, the resulting phase is presented as a fractional value of the RRI. The same values can be presented in alternative units of measure: multiplying the right hand side by 100 results in units of % RRI; multiplying by 360 provides the phase in degrees; and multiplying by $2\pi$ provides the phase in radians. The equivalent phase information 162 can be determined alternatively using a span of CC 52 and MSK 160 signals in their entirety rather than the specific $CC_t$ and $MSK_t$ event times. For example cross correlation methods can be utilized in comparing PPG (alternatively, ECG) and accelerometer signals to determine the time lag or phase relationship between them in 162.

Similarly, the aHR value can be computed using detected events within the CC signal 52 (e.g., R-waves within an ECG signal), or from a span of CC signals 52 without identifying specific events (e.g., a Fast Fourier Transform of an ECG signal).

Within many exercise and other active situations, it can advantageous for a user to remain below a certain maximal desired heart rate (mdHR) that differs between users and can differ between different activities for a given user. For example, maximal achievable heart rates (HRmax) and safe HR ranges typically decrease with age. mdHR may change dependent on the user's goals. For example, if the primary goal is safety, then a user may want to remain below 90% of HRmax. If remaining below lactate acid threshold is the user's goal, a lower mdHR will be preferred. In certain methods and embodiments of the disclosure, modification of the user's HR can be enabled by various means.

Figure 9:
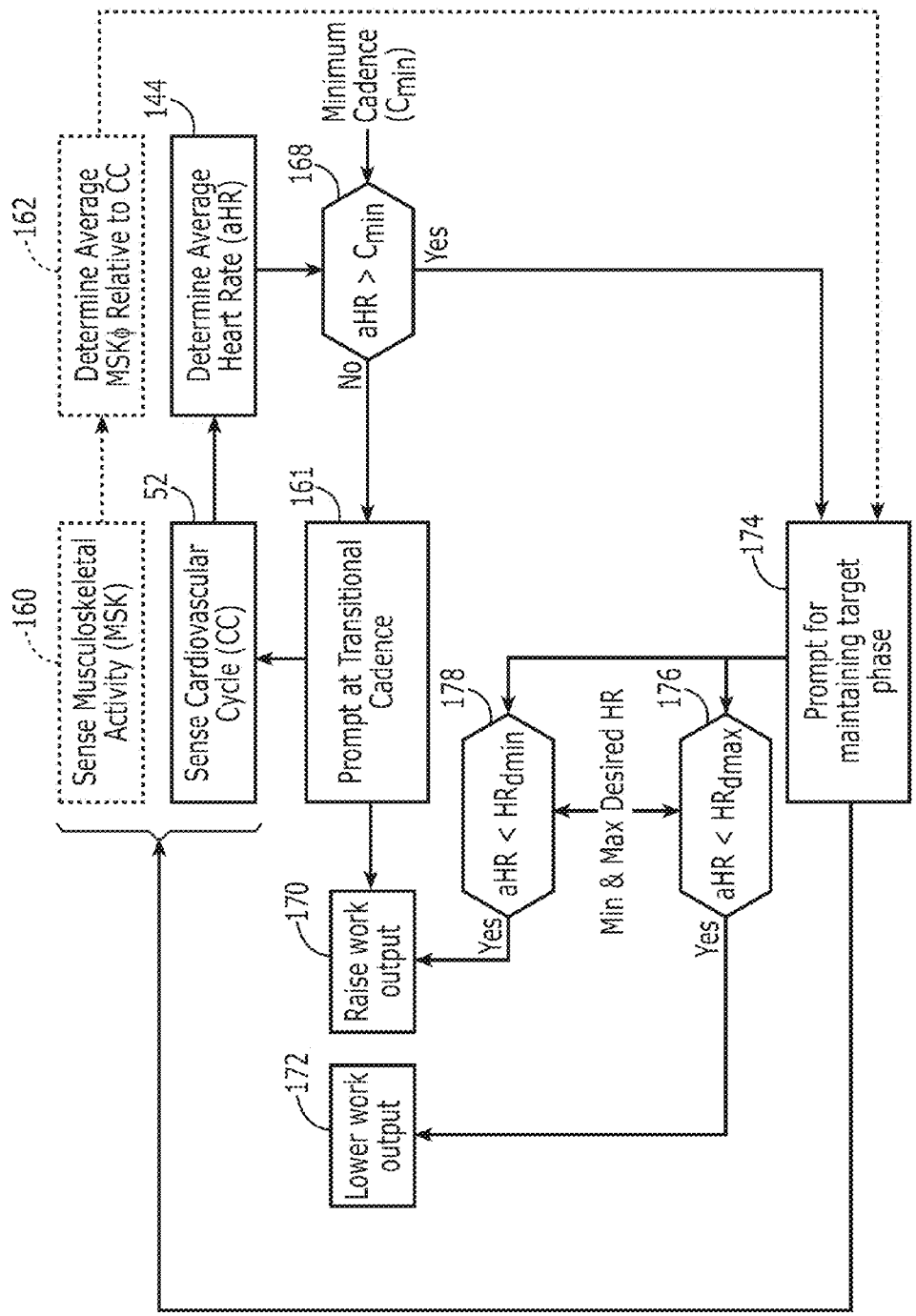
FIG. 9 is a flow chart illustrating a continuous operating mode that includes steps for maintaining a desired target HR range according to an embodiment of the present disclosure.

FIG. 9 illustrates an embodiment of the present disclosure that provides for guiding a user in maintaining their HR within a targeted range while further assisting the user in coordinating their MSK and cardiac pumping cycles. After sensing the user's CV cycle 52 and determining their aHR 144, the aHR is compared 168 to a pre-set minimum cadence value ($C_{min}$), for example a rate of 150 BPM associated with a running cadence; or in another example, $C_{min}$ can comprise a multiple of their activity repetition rate such as 4×36=144 BPM if the user is rowing at a cadence of nominally 36 strokes per minute. Thus $C_{min}$ can be an activity-dependent value. If aHR is less than $C_{min}$ in 168, the user is provided with feedback 161 comprising a transitional cadence and additional guidance 170 to raise their work output to help increase their HR. In an alternative embodiment configured to interface with an exercise machine or other apparatus, the instruction 170 to raise work output can executed by the machine, for example by increasing the load (e.g., incline or resistance).

When the aHR increases beyond $C_{min}$, prompts 174 for maintaining a target phase are provided, for example using the methods described according to FIGS. 6B, 10, 12, 13, 14, 26 or other embodiments of the present disclosure. The user's MSK activity 160 is optionally sensed and average $MSK_\phi$ relative to their CC determined 162. If so included, this information can be utilized in 174 for determining feedback prompt timing. Additionally, the user's aHR 144 is compared to specified values of a maximum desired HR ($HR_{dmax}$) and minimum desired HR ($HR_{dmin}$) (176 and 178, respectively), determined beforehand in accordance, for example, with their mdHR, HRmin, and/or HRmax. If the aHR 144 exceeds either of the two limits 176 and 178, the user is additionally provided feedback guidance to raise (170) or lower (172) their work output to assist in recovering to an aHR value 144 within these defined bounds. In alternative embodiments that include an exercise machine, these instructions 170 and 172 can be used for manual or automatic adjustments to the resistance (load) settings for bringing the user's aHR value 144 within the defined bounds.

The information 172 to "lower work output" can, for example, comprise guiding the user to shorten their stride while walking, jogging or running; slowing down; or decreasing the force of MSK contraction. In an embodiment that includes an exercise machine or other apparatus, lowering work output 172 can comprise, for example, decreasing the incline on a treadmill, lower pedaling resistance (e.g. gear) on bike; or shortening the stride length of an elliptical machine. "Raise work output" 170 could comprise the opposite guidance or control (e.g., lengthening stride, speeding up, increasing the bicycle gear, etc.).

Beyond monitoring the user's cardiac cycle (CC) and providing feedback to guide the user's musculoskeletal activity (MSK), certain continuous operating mode configurations described herein or contemplated further monitor the user's MSK directly and determine its timing and/or phase with respect to their cardiac cycle (MSK). The system 180 configured in FIG. 10 similarly includes sensors and provisions to sense the user's MSK 160 and CC 52, and determines $MSK_\phi$ 162 (as described with, for example, FIG. 7). Additionally, system 180 compares in branching step 188 the average $MSK_\phi$ ($\phi_{avg}$) 182 to a target phase ($\phi_{target}$) and provides a first type 184 or, optionally, a second type 186 of feedback indicator to the user dependent on whether the absolute $\phi_{avg} - \phi_{target}$ difference is, respectively, within or beyond a specified tolerance Y. The tolerance Y is selected to maintain a phase or time delay range that yields acceptable results dependent on the application. For example, a tolerance of Y=10% phase would provide the first feedback indicator 184 when $\phi_{avg}$ is within ±10% of the target, and the second (optional) feedback indicator 186 when it is not. The system 180 loops continuously while monitoring the user and providing the appropriate feedback indications.

Figure 10:
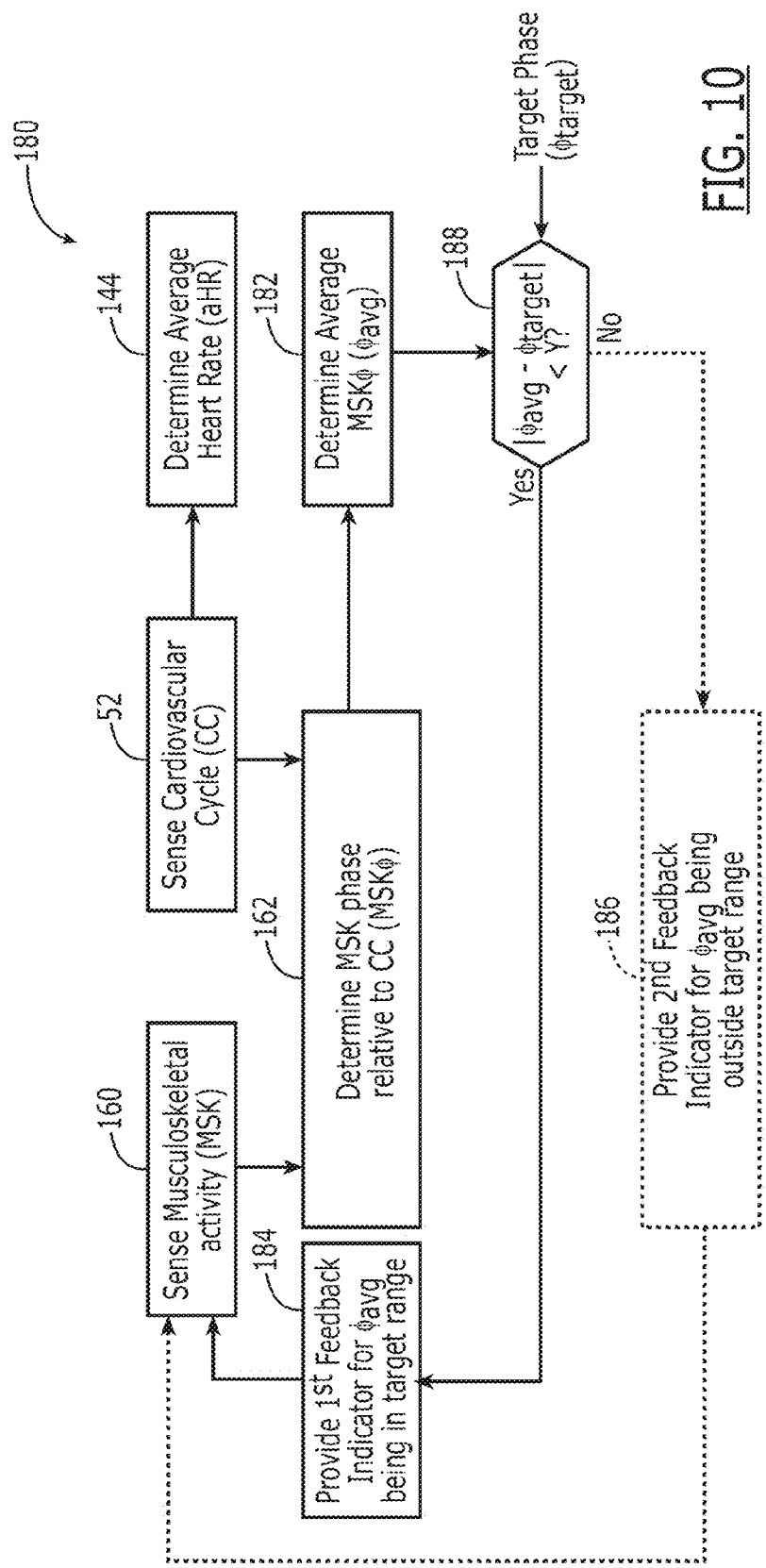
FIG. 10 is a flow chart of an exemplary embodiment of a system configuration that provides one type of feedback indicator when a user's MSK activity is within a targeted phase range with respect to their CV pumping cycle, and optionally a second feedback indicator when activity is outside of that range.

The computation in 182 for determining $\phi_{avg}$ can be accomplished in any of a number of ways as will be understood by one skilled in the art. For example, $\phi_{avg}$ 182 can be computed by taking an algebraic mean of the last 10 computed $MSK_\phi$ values 162; alternatively, using a weighted mean wherein the more recent values are given more influence; alternatively, an average over the last 20 seconds of accumulated $MSK_\phi$ 162 values; by using a moving average infinite impulse response filter; et cetera. The response time of the averaging process influences the responsiveness of bypassing the first indicator 184 or changing between the first 184 and second 186 feedback indicators if a second indicator is provided. Thus the details of computing $\phi_{avg}$ are considered in the context of how the system 180 of FIG. 10 is being used. In an alternative configuration of system 180, if the aHR 144 differs meaningfully from the user's MSK cadence (which can be derived from 160), several of the shown steps can be optionally bypassed (e.g., 162, 182 and the branching 188 to 184) as the $MSK_\phi$ value necessarily cycles through the full span at a rate that depends on the difference between the user's MSK cadence and their HR.

FIG. 10 can be described more fully by way of three examples using different configured choices of target phases and/or feedback indicators 184 and 186. In a first example, the $\phi_{target}$ value is selected to represent a desirable value (e.g., one that results in a reduced aHR or other measure representative of MCP) and the first indicator 184 is configured to provide the user with pacing prompts for timing their movements. This first feedback indicator 184 can comprise, for example a repeating audible beep tone and/or visual and/or tactile cue used for timing steps while running or walking or, in another example, when to stroke when rowing. The second feedback indicator 186 may be unused in this example or, in an alternative embodiment, configured to alert the user that they are not within the targeted phase range while helping guide them back to it. For example, this second indicator 186 could provide pacing prompts with a different characteristic such as a distinctly different sound or appearance than what is used in the first indicator 184.

An alternative configuration of FIG. 10 serves to provide a protective or "watchdog" mode of operation for the user. In this example, $\phi_{target}$ is selected to represent an undesirable $MSK_\phi$. An example application of such a mode could be used advantageously by long distance runners for which prolonged periods of MSK activity working against the CV pump (i.e., inverse MCP) may place them at increased risk of inadequately perfusing their cardiac tissues. While the user's MSK activity (and resulting $\phi_{avg}$) "safely" differs from $\phi_{target}$, branching step 188 does not select the first feedback indicator 184; a second feedback indicator 186 (if included) can comprise a green light to signify that the activity need not be modified so long as the indication 186 persists. This state could be the result of the user's MSK cadence differing sufficiently from their aHR value, or the average $MSK_\phi$ 182 value not persisting at the undesirable phase for more than the averaging response time. However, if the user's $\phi_{avg}$ value falls within range in branching step 188 (or, optionally, within range for a predefined excessive period of time), first feedback indicator 184 provides the user with information that their activity is being conducted at an undesirable timing relative to their cardiac cycle. This indication 184 can be an audible warning, or an audible pacing prompt for guiding the user away from the undesirable timing or, additionally and/or alternatively, a visual cue (e.g., red light).

The third example of FIG. 10 configures the system to operate in a "training" mode, helping the user learn how to pace themselves in a properly coordinated manner relative to their CC. Here, $\phi_{target}$ is chosen to represent a desirable phase or timing; the first feedback indicator 184 operates non-intrusively to communicate to the user that they are properly timing their activity (e.g., silently, with a visual solid green light); and the second feedback indicator 186 provides pacing prompts at a target cadence and phase to guide the user to the proper timing. In an alternative configuration, first feedback indicator 184 comprises a properly timed and phased audible pacing prompt with a pleasant tone and/or low volume, while the second feedback prompt 186 alters the pitch to be less pleasant and/or raises the volume of otherwise equivalently timed pacing prompts.

The method of decreasing or eliminating the volume of an audible prompt or the magnitude of a tactile prompt, when accuracy is maintained, can be an important feature of a training embodiment of the system, wherein a user is taught to maintain or even obtain target timing by feel, without continued audible prompting, for example, in an effort to teach the user to be able to physically sense appropriate timing and thereby wean the user from requiring the device in order to obtain and maintain MSK activity timing conducive to achieving and maintaining MCP. Such a training embodiment of the device can be a selectable mode of use. The ability to train in this way and thereby learn the technique of achieving and maintaining MCP independent of a biofeedback device may be of particular use to competitive athletes, who may not be able to utilize the biofeedback device during competition.

Figure 11:
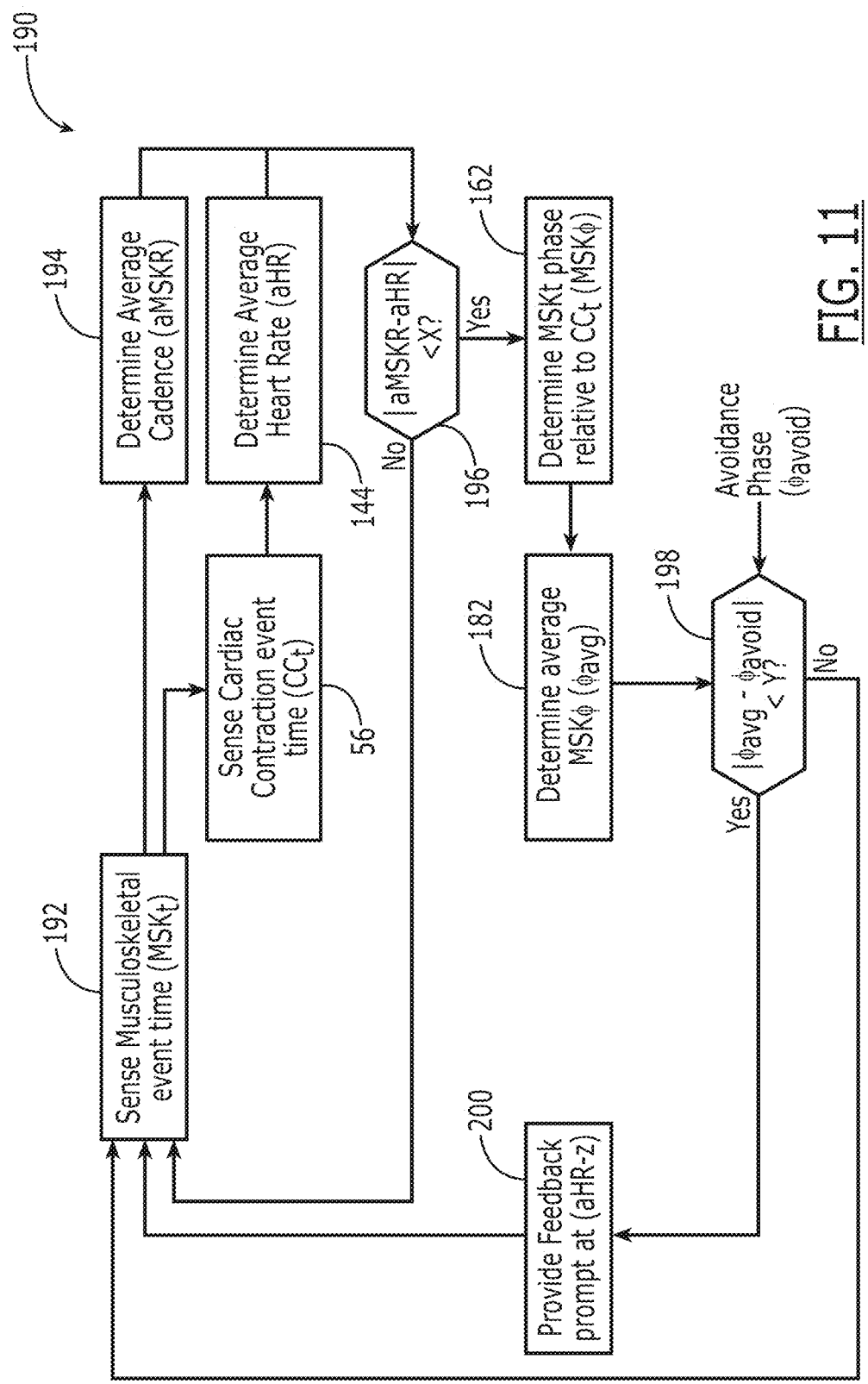
FIG. 11 is a flow chart of an exemplary embodiment of a system that monitors the user's CV pumping cycle and MSK activity and provides a non-synchronous pacing prompt if the sensed activity timing occurs with an undesirable relative phase.

The system shown in FIG. 11 provides another exemplary embodiment of a protective or "watchdog" continuous mode, operating silently without disturbing the user until their sensed activity timing occurs with an undesirable phase relative to their cardiac cycle. System 190 includes the steps of sensing the user's repeating musculoskeletal ($MSK_t$) 192 and cardiac contraction ($CC_t$) event times 56, from which their average cadence (aMSKR) 194 and average heart rates (aHR) 144 are determined. These two values are compared in 196; if their absolute difference remains above a value X (e.g., an absolute rate difference of >3 per minute), the looping cycle continues without further action. If the rate difference 196 becomes less than X, the $MSK_t$ and $CC_t$ event times are used to compute the relative phase ($MSK_\phi$) 162, from which the average $\phi_{avg}$ value is determined 182. Step 198 compares $\phi_{avg}$ to a pre-determined avoidance phase $\phi_{avoid}$ that represents an undesirable condition such as inverse MCP. If the absolute difference of these two values is less than Y (e.g., 5%), or alternatively less than Y for more than a pre-determined period of time, the user is provided with feedback prompts 200 at a cadence that differs from their aHR by z per minute in order to direct their activity to a rate different than that of their cardiac cycle. The value of z can be a positive or negative value and generally a value similar though larger in magnitude than X. If, however, the comparison 198 differs by more than Y, the user's $\phi_{avg}$ is not sufficiently close to the avoidance phase value and, accordingly, they do not need to be alerted and paced to a different cadence. System looping continues after 198 or 200 as appropriate.

While FIG. 11 depicts MSK 192 and CC 56 activity sensed in a particular order, these steps can be determined in a different order or, effectively, in parallel. Similarly, $MSK_\phi$ 162 can be determined at a different location within the flow diagram or determined in combination with $\phi_{avg}$ 182. Comparison 196 can further include a counter of time or events that the test condition is "True," triggering the feedback prompt 200 to pace the user to a cadence different from their aHR 144 only after a pre-determined sufficient duration or count is exceeded. This duration can be an absolute value (e.g., five minutes) or, alternatively, a percentage of the activity time (e.g., 10% of the elapsed activity duration)

Figure 12:
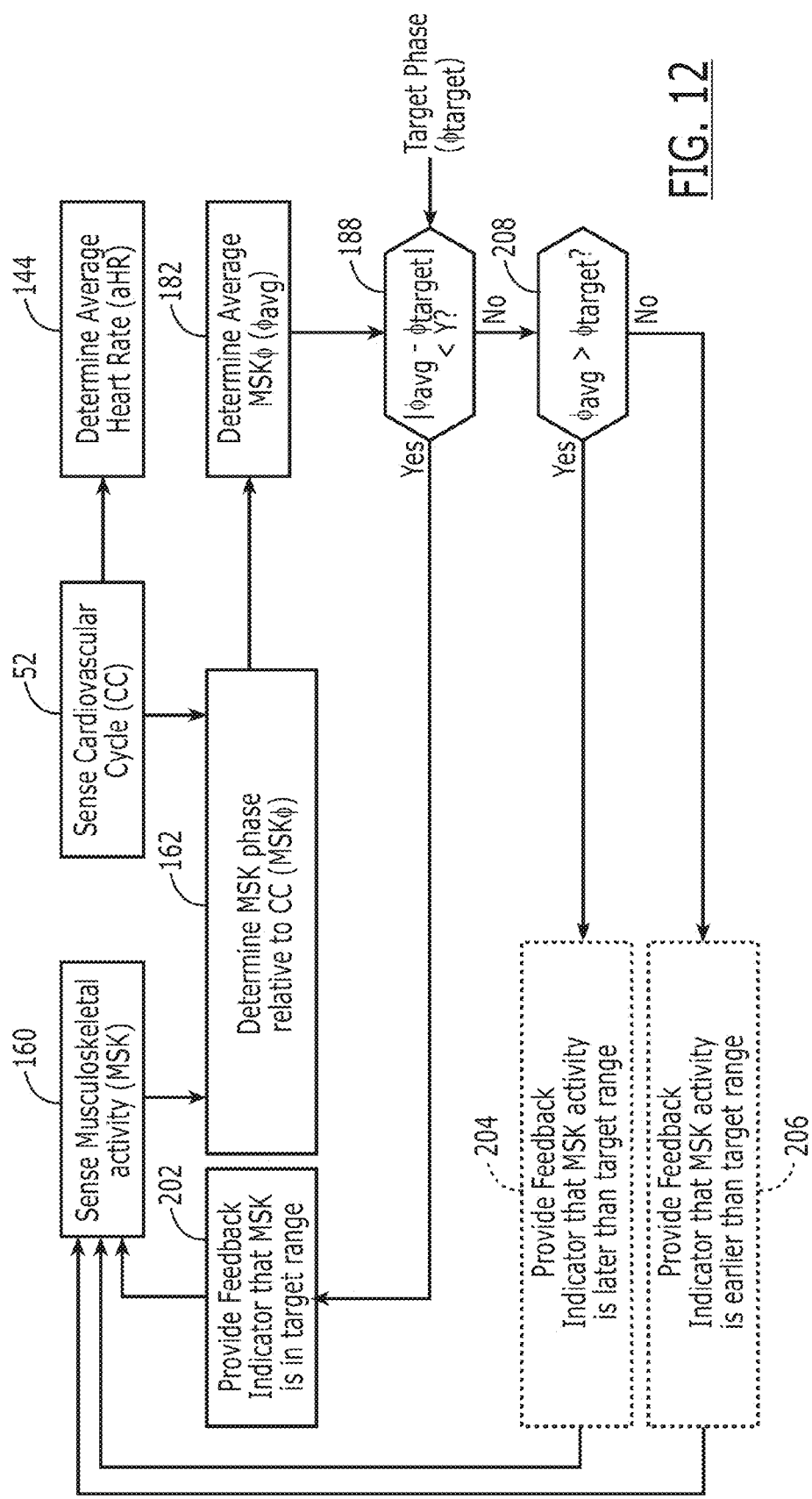
FIG. 12 is a flow chart of an exemplary embodiment of a system that monitors the relative phase of the user's MSK activity with respect to their CV pumping cycle and provides respective feedback indications when the activity is within, later than, or earlier than a target range.

FIG. 12 diagrams another exemplary configuration that evaluates the user's average $MSK_\phi$ ($\phi_{avg}$) in comparison to a target phase ($\phi_{target}$) and provides one indicator when user is inside a target range and, optionally, other indications when outside the range to help guide the user in properly coordinating their activity with their cardiac cycle. The process begins by sensing the user's MSK 160 and CC activity 52 and determining the aHR 144, MSK$_\phi$ 162 and $\phi_{avg}$ 182. If the absolute $\phi_{avg}$–$\phi_{target}$ difference is less than a pre-defined tolerance Y (188), the user is provided with indicator 202 to communicate that their MSK activity is within the target phase range. If their activity is outside of the target phase range, test 208 determines if their $\phi_{avg}$ is greater or not greater than $\phi_{target}$ and, optionally, provides respective feedback indicators 204 or 206 to the user that their activity timing is, on average, later or earlier than the target value, allowing the user to modify their timing accordingly. In an alternative configuration of the system shown in FIG. 12, the aHR 144 and aMSKR values can be compared as in the system of FIGS. 11 (144, 194, and 196) prior to test 188 or alternatively 162.

In one exemplary configuration of the system in FIG. 12, the audible quality of the prompts can be used to indicate that the user is stepping accurately or inaccurately. For example, the pitch of indicator 204 can comprise an audible tone (cadence prompt) signaling that the MSK activity needs to occur earlier (e.g. low pitch means "too slow"), while indicator 206 is used to communicate that the activity needs to occur later in the cycle (e.g. high pitch prompt means "too soon"), and 202 to indicate that the activity is "right on" (e.g. pleasant neutral tone). In other embodiments, when the tone timing is automatically adjusted to consistent early or late steps, the audible tone's quality in 202 can simply signify an accurate step (tone quality #1) vs. an inaccurate step (tone quality #2) for indicators 204 and 206. Alternatively, audible enunciators can each use the same pitch.

In further embodiments, the prompt's magnitude (e.g. audible prompt volume or a tactile prompt force) can vary in response to the accuracy of MSK pump timing, for example, the volume of the prompt (e.g., 202) could grow quieter, or even silent, as accurate MSK pump timing is maintained, while the volume of the prompt 202, 204, and/or 206 could increase as the user's timing strays from optimal. Increasing prompt loudness can also be used as a way to alert the user that they are not adequately concentrating on accurate movement or skeletal muscle contraction timing.

Figure 13:
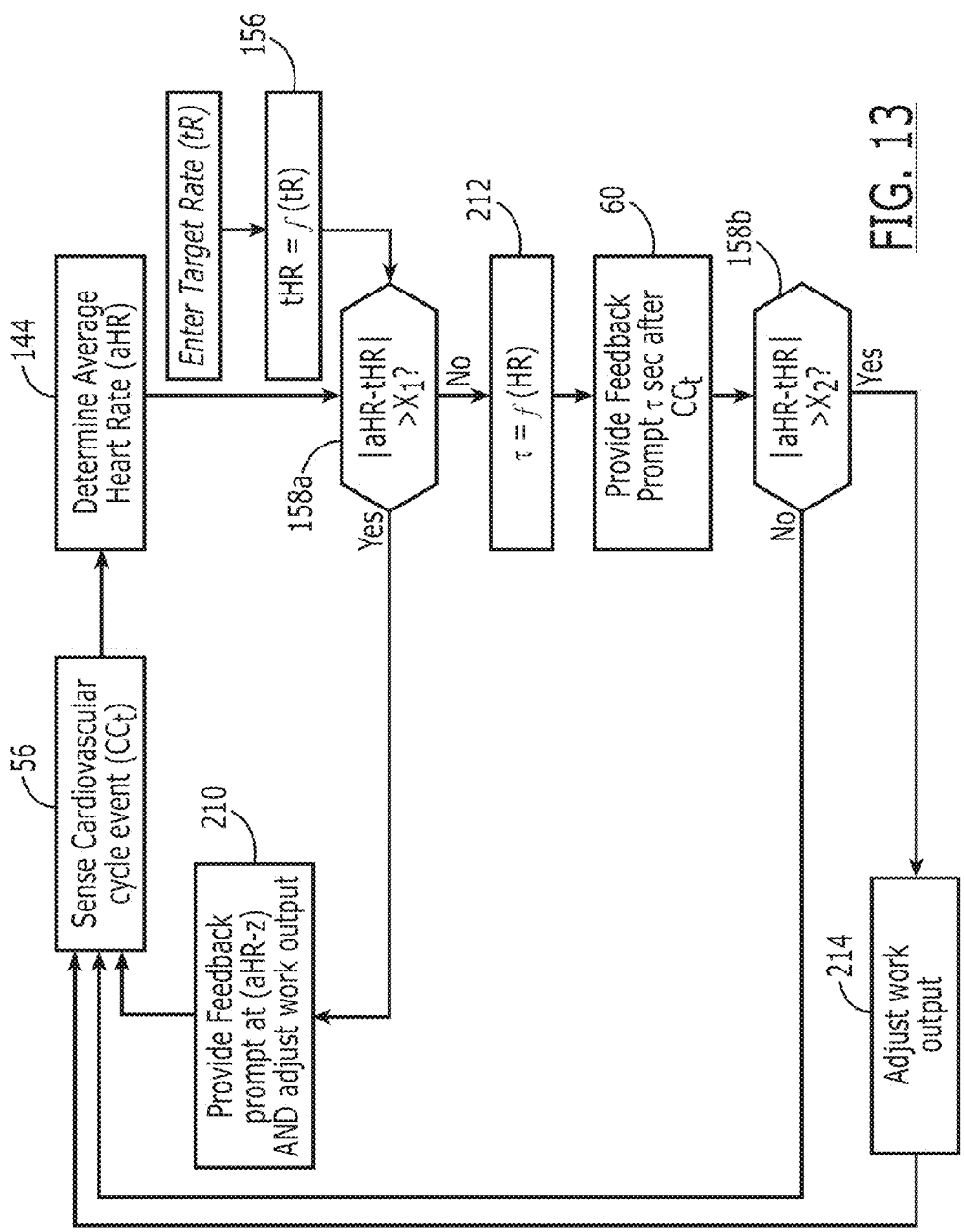
FIG. 13 is a flow chart of an exemplary embodiment of a system that monitors the user's CV pumping cycle and provides pacing feedback prompts along with an additional indication to adjust the work output if the average HR differs from a target HR range.

Another exemplary system that provides feedback to the user for coordinating their activity and maintaining a target HR is shown in FIG. 13. After sensing the user's CV event time (CC$_t$) 56 and determining their aHR 144, the aHR value is compared in 158a to their target heart rate (tHR) 156, a value derived from the user's target rate (e.g., using the information as described in FIG. 5). In 158a, if the rates differ by more than a pre-selected first tolerance X$_1$ (e.g., 5 per minute), looping continues by providing pacing feedback to the user 210 at a rate that differs from their aHR 144 by a preselected amount z (e.g., 5 per minute), along with instruction to adjust their work output in order to bring their aHR 144 closer to the tHR 156. Once the aHR 144 settles within the tolerance X$_1$ of the tHR 156, a delay time $\tau$ 210 is determined based on their beat-to-beat heart rate (HR) or aHR 144, to target, for example the timing of a fixed event in the cardiovascular cycle such as the end of the T-wave or, alternatively, the timing of the dicrotic notch. Feedback prompts 60 delayed in time from CC$_t$ 56 by $\tau$ 212 are provided to pace the user in properly coordinating their activity. If the aHR 144 deviates from the tHR 156 by a preselected second tolerance X$_2$ (e.g., 3 per minute) in 158b, the user is instructed to adjust their work output 214 accordingly and looping continues, otherwise looping continues without the additional instruction 214.

The function $f$(HR) depicted in 212 for determining a delay time $\tau$ can be configured in numerous ways. For example, $\tau$ could target a time after the R-wave in a manner that is not HR-dependent and, accordingly be a constant value such as 50 ms, or alternatively 150 ms. In another example, already discussed above, $\tau$ could target a specific phase of the cardiac cycle (e.g., 35% of the R-R interval), which inherently is HR-dependent. In yet another example, the delay $\tau$ can target specific regions within the beat-to-beat interval such as end T-wave 30 (FIG. 2), approximating the timing of aortic valve closure. The HR-dependent (or aHR-dependent) values of $\tau$ can result from a continuous function in which any numerical value could be used (e.g., 0 s, 0.001 s, . . . , 1.500 s, 1.501 s, 1.502 s, etc). Alternatively, $\tau$ can be selected from a finite list of available choices based on HR, aHR, tHR, or other variables. For example, a value of $\tau$=135 ms corresponds to approximately 30% of the R-R interval at a HR of 133 BPM and ~40% of the R-R interval at 178 BPM. Similarly, $\tau$=165 ms corresponds to ~30% at 109 BPM and ~40% at 145 BPM. Thus switching the value of $\tau$ selected from a limited set of accessible delay times can maintain the user's MSK phase within a limited span around a target phase (e.g., 35±5%), while simultaneously being capable of spanning a wide range of HR values. Values of $\tau$ that are less than a CC$_t$-to-CC$_t$ interval (e.g., R-R interval) target prompts and user movements to fall within the current cardiac cycle; values of $\tau$ greater than the CC$_t$-CC$_t$ interval result in prompts falling in a later cardiac cycle. Because of the rhythmic nature of the cardiac cycle, providing a prompt with a delay that falls in a subsequent interval is equivalent to targeting the same phase in the current interval (e.g. 30%, 130%, and 230% phase delays are all equivalent, provided the HR is not rapidly changing).

The guidance to "adjust work output" in 210 and 214, when the user's aHR 144 is too low, can inform the user to increase stride length (speed), resistance, incline, or increase cadence above their aHR or above their tHR. When the aHR is too high, this guidance can, conversely, be to decrease stride length (speed), resistance, incline, or decrease cadence below aHR, etc.

Users can respond to provided feedback prompts with timing that differs from individual to individual. While the prompts are provided at a specific targeted timing relative to their cardiac cycle, a user can systematically move and/or contract their muscles earlier or later than the target timing. For example, in the case of running to the rhythm of audible pacing prompts, a user can choose to synchronize their stride based on foot-strikes, while on other days (or with different users) can synchronize based on the push off that occurs slightly later. The system of FIG. 12 provides feedback indicators to guide the user to alter their timing if the sensed average MSK$_\phi$ is early or late. An alternative method for guiding the user in properly aligning their MSK timing to their cardiac cycle is to adapt the feedback prompt timing itself. For example, a consistently late step can be corrected by presenting the user with an earlier prompt; equivalently, consistently early steps can be corrected with later prompts.

Figure 14:
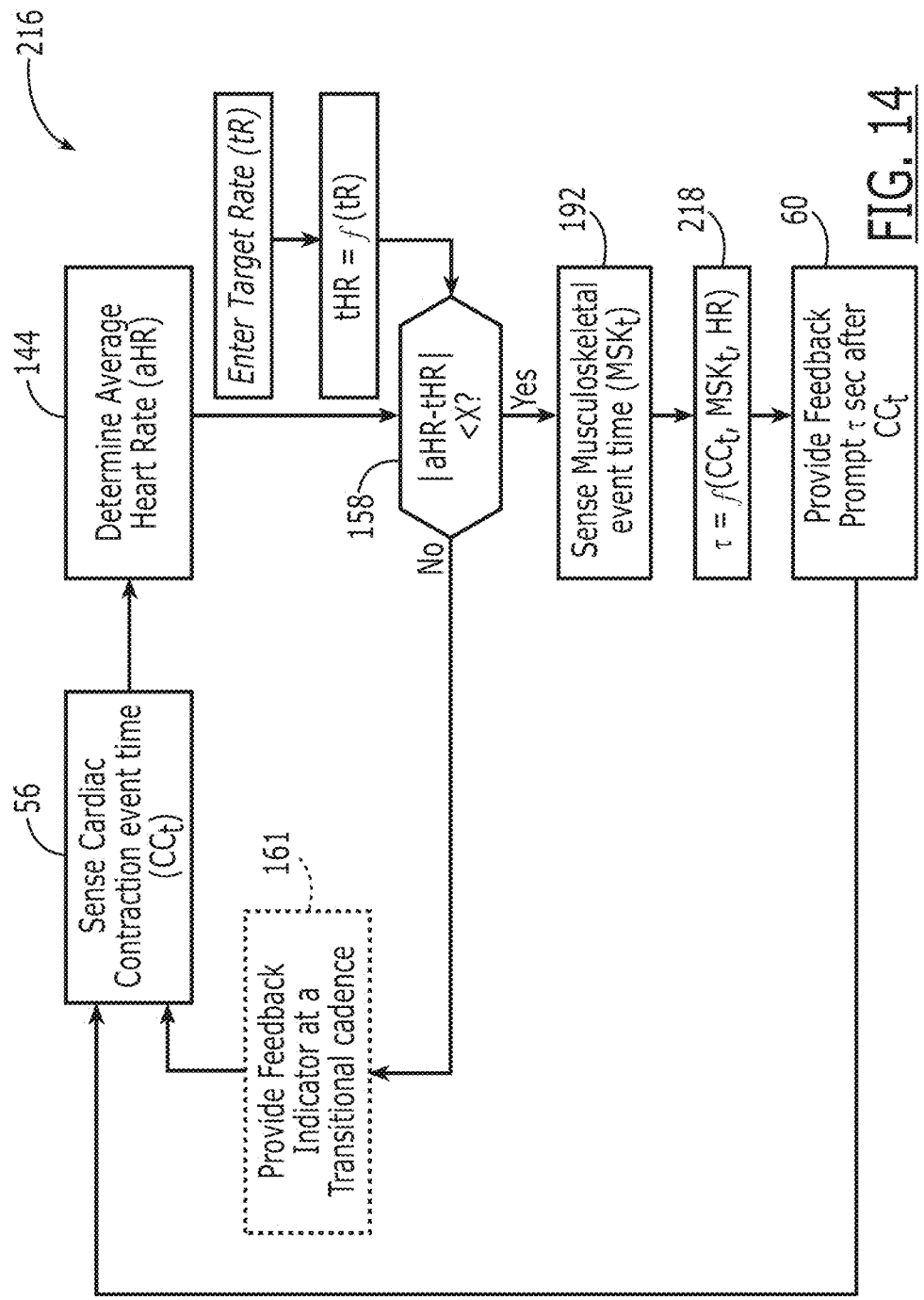
FIG. 14 is a flow chart of an exemplary embodiment of a system that monitors the timing of user's CV pumping cycle and MSK activity and provides guidance prompts delayed with respect to the CC timing by an adaptive value computed using the measured variables.

An example of such a system is shown in FIG. 14. System 216, begins by sensing, with a first signal, the user's CC$_t$ 56, determining their aHR 144, and continues with an optional initial warm-up loop comprising steps 158, and 161, equivalent to similar warm-up mode steps as described earlier (e.g., in the systems of FIG. 7 and FIG. 9). Once the user's aHR reaches their tHR zone within tolerance X (158), process 216 continues by sensing, with a second signal, the timing of their rhythmic MSK activity 192. Delay time τ is computed in 218 as a function of their $CC_t$ 56, $MSK_t$ 192 and heart rate (HR or, alternatively, aHR 144) in a manner that accounts for deviations between the sensed delay (e.g., by comparing the timing of the two events as a difference: $MSK_t - CC_t$) and a targeted delay computed from the target phase $\phi_{target}$. One such method is described here: let $\phi_{target}$ represent a target phase delay (e.g., 0.35 or 35% of the RRI), w represent a weighted-averaging factor with a value between zero and one (e.g., 0.90), and δ represent an actual offset value (initialized with a value of zero) calculated as:

$$\delta = w \cdot \delta + (1-w) \cdot [\phi_{target} \cdot (CC_t - CC_{t\_last}) - (MSK_t - CC_t)].$$

In this equation, $CC_{t\_last}$ represents the most recent prior value of $CC_t$, such that $60/(CC_t - CC_{t\_last})$ is equal to the user's instantaneous beat-to-beat HR.

The prompt delay time 218 is then calculated as the sum of the target timing delay and the actual offset:

$$\tau = \phi_{target} \cdot (CC_t - CC_{t\_last}) + \delta.$$

Process 216 continues by providing the feedback prompt 60 and looping back to 56 to repeat the process. As can be seen in these equations, if the user's average $MSK_t$ is delayed properly from $CC_t$, δ becomes zero and τ is unaffected. However, if the users movements are systematically "late", δ becomes a negative value and the resulting prompt timing is made to occur earlier (if the timing computes to be a value sooner than the system can respond to, the prompt can be delayed by an additional heart beat period so to occur in the next cardiac cycle.) Comparable system response occurs when the user's average movements are "early," causing the prompt to be made later. In each case, beyond automatically adjusting the delay due to changes in the user's HR, the prompt delay time is further adjusted to accommodate the user's response to the recurring prompts, so that the $MSK_t$ events occur the desired point with respect to their cardiac cycle.

Figure 15A:
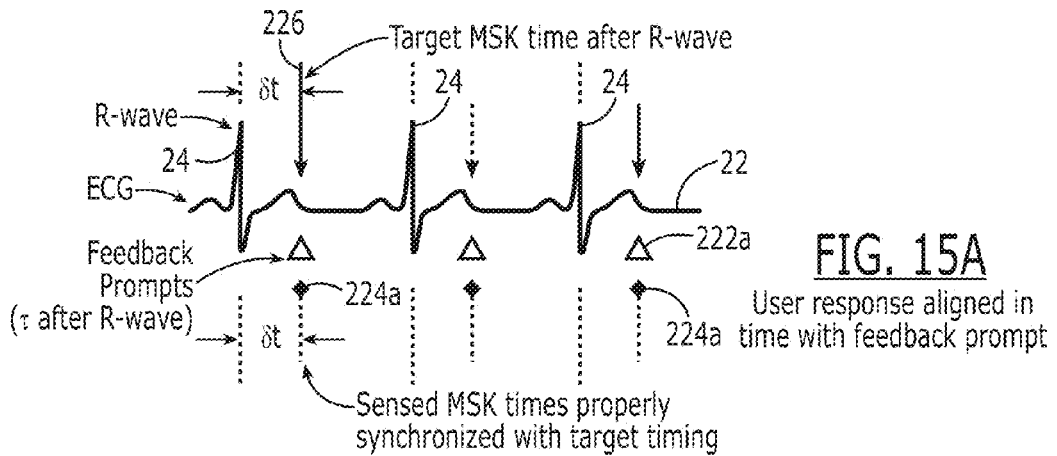
FIGS. 15A-C are ECG plots illustrating user response times, showing response aligned with prompt, response "late" relative to prompt, and prompt timing adjusted to anticipate "late" response, respectively, according to an embodiment of the present disclosure.
Figure 15B:
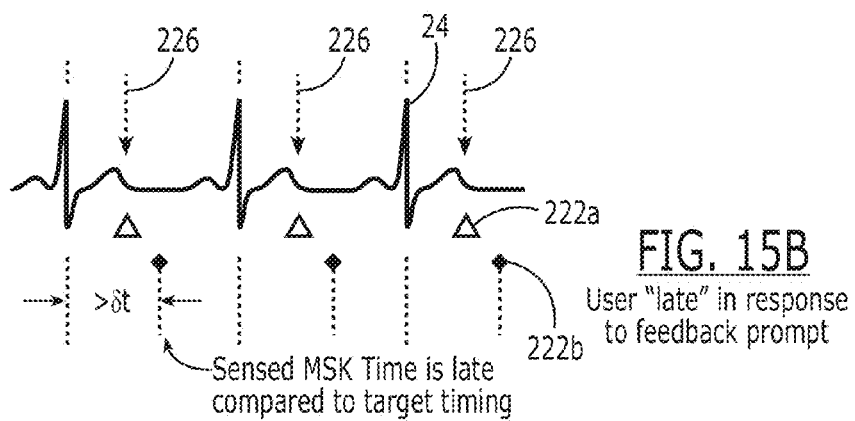
Figure 15C:
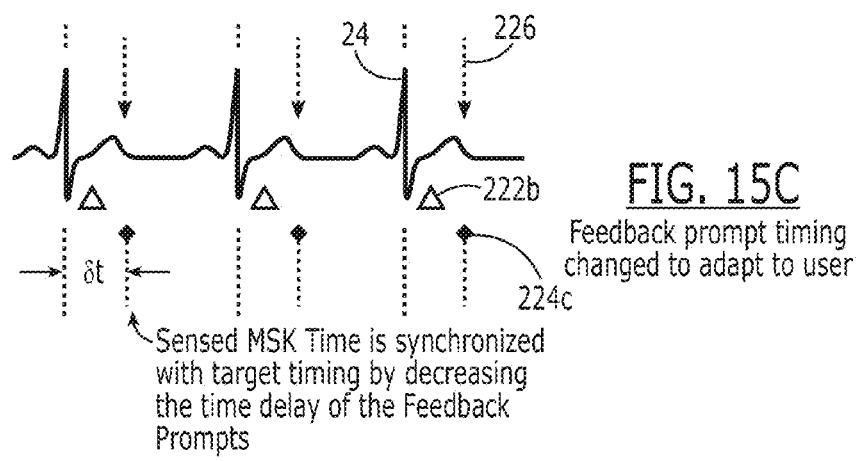

Further clarification of this adaptive tuning of prompt timing can be illustrated in FIGS. 15A-C. An exemplary ECG signal 22 is shown in FIG. 15A, with the R-wave 24 identified and considered in this example to represent the timing of the cardiac $CC_t$ events (as in 56). The target MSK time after $CC_t$ 226 (equivalent to $\phi_{target} \cdot [CC_t - CC_{t\_last}]$) is shown in the figure to occur at a time δt after the R-wave 24. In FIG. 15A, both the feedback prompts 222a and sensed MSK times 224a are synchronous, with both occurring properly δt after the R-wave 24. In FIG. 15B, representing a user that is systematically moving "late" relative to the feedback prompt timing 222a, the MSK time 224b is sensed to be later than the target time 226, i.e., with a delay from the R-wave 24 greater than δt. In FIG. 15C, the prompt timing 222b after the R-wave 24 has been shifted to occur earlier than with 222a in FIGS. 15A and 15B, resulting in the sensed MSK time 224c becoming better aligned properly with the target timing 226, thus compensating for the user's movements without the need for them to modify their behaviors.

Beyond the need to adapt the timing of prompts to account for variations in how users respond, there may be periods of time in which the cardiac cycle is difficult to monitor on a beat-to-beat basis. For example, $CC_t$ can be sensed using an ECG, PPG, or other signal sensitive to the cardiac cycle, which may not be available or reliable at all times, due to noise or other factors. Feedback prompts delayed in time after spurious or missed $CC_t$ events may become increasingly erratic as signal CC signal quality degrades, thus making it difficult for the user to properly coordinate their MSK activity cadence to their underlying CC. Similarly, detecting MSK events (such as the timing of the user's steps while walking or running) may be disrupted by signal noise or other artifacts.

Additionally, in certain device implementations, data communication delays or variability between the occurrence of the physiologic signals themselves and the receiving of the signals at a potentially remote processor unit, along with the processing time to analyze signals, may impact the ability to detect $CC_t$ and $MSK_t$ events soon enough to provide feedback prompts within the current or upcoming cardiac cycle. Accordingly, there is a need to provide continuous prompting indicators to assist the user in properly aligning their movements with their cardiac cycle while tolerating imperfect signal quality and/or unknown delays of received signals relative to the user's physiology and activity.

Figure 25:
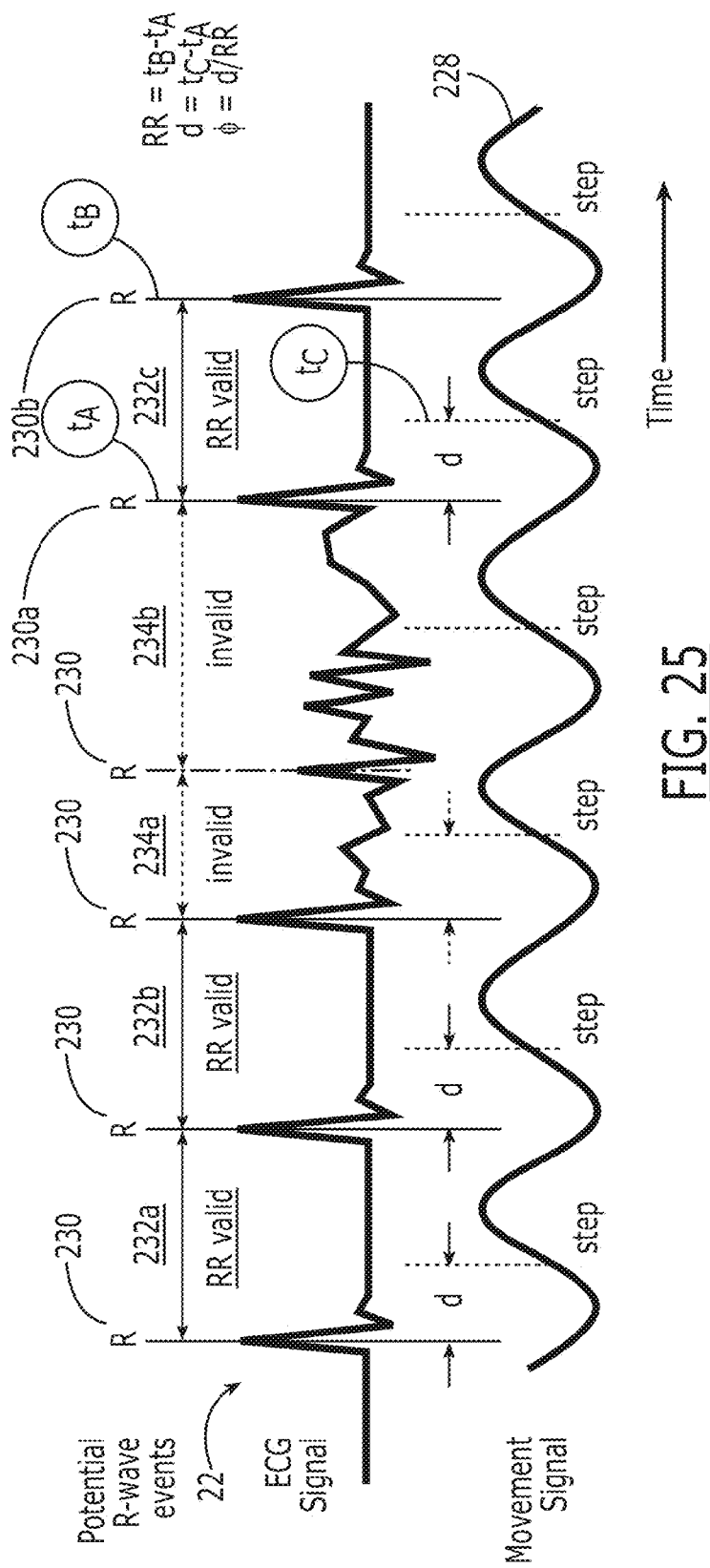
FIG. 25 illustrates several seconds of movement and ECG signals collected simultaneously that further includes signal noise artifacts.

Consider the FIG. 25 that shows a movement signal 228 and a series of "clean" and "noisy" R-waves 230 within an ECG signal 22 being used to detect a user's cardiac cycle; R-waves 230a and 230b refer to the R-wave events occurring at times $t_A$ and $t_B$, respectively. One approach for addressing the need described above is to provide a repeating feedback prompt with a period computed from their recent valid R-R intervals 232a-c (i.e., excluding R-R intervals 234a-b caused by spurious or missing R-wave events 230 that are inconsistent with, for example, the recent average of valid R-R intervals). Using the valid signals, a system can continuously adjust the timing delay to accommodate changes in the user's HR, further adjust the delay to maintain the sensed MSK activity at a targeted relationship relative to the user's CC, and update the timing of the feedback prompts. In the absence of continuous and consistent R-R intervals (or MSK signals), the feedback prompts can continue at their prior rhythm.

Figure 26:
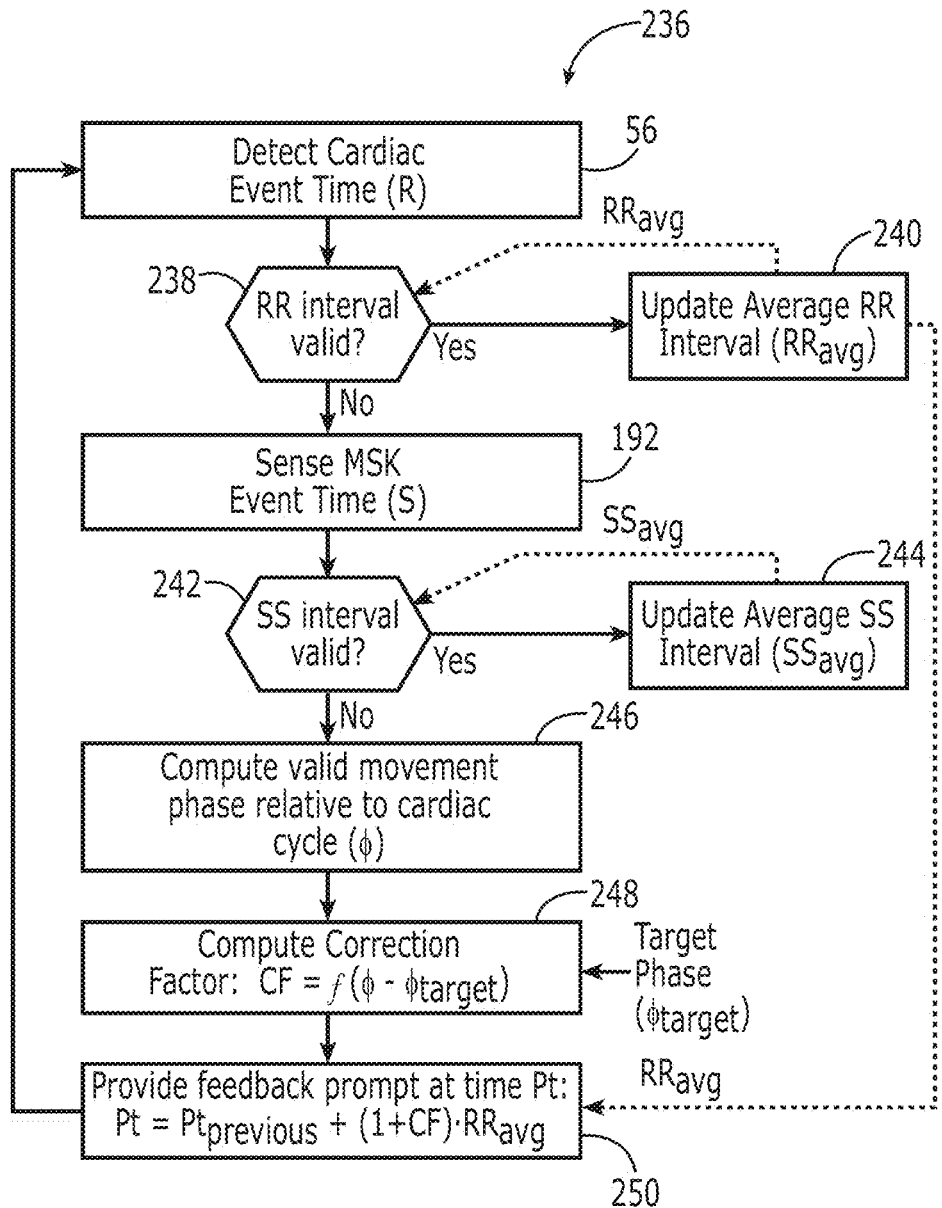
FIG. 26 is a flowchart of an exemplary system according to the present disclosure for monitoring and validating the user's cardiac and MSK activity signals, providing adaptive feedback prompts to the user for properly coordinating their activity with their cardiac cycle, and tolerating signal noise and system delay artifacts.

Such a system is described more fully in FIG. 26. The process in system 236 begins with detecting a cardiac event time 56, for example an occurrence of an R-wave in the ECG signal, (i.e., $CC_t$ is designated as R in FIG. 26), such as 230b designated as $t_B$ in FIG. 25. Since these detected events may include noise causing spurious or "phantom R-waves", as well as causing, occasionally, true R-waves to be missed, the intervals between the most recently detected successive R-waves (e.g., 230a and 230b, equivalently $t_A$ and $t_B$ in FIG. 25) are validated in 238 by, as an example, comparing them to the recent history of valid R-R intervals ($RR_{avg}$). If an interval is found to be valid, it is used to update $RR_{avg}$ in 240 for validating subsequent signals. $RR_{avg}$ is also used in 250 for establishing the nominal period of feedback prompts. MSK timing is treated similarly by first detecting a selected recurrent component of the user's rhythmic musculoskeletal activity that repeat at the user's cadence to represent potential events (S) in 192 and then validating them in 242. In this example, $MSK_t$ is signified by a "step" timing S and step-step intervals (SS) are compared to the recent average valid SS interval ($SS_{avg}$) 242 for determining validity. RR and SS intervals that differ from their respective $RR_{avg}$ and $SS_{avg}$ counterparts by more than a pre-determined threshold are, in this example, ignored. The user's valid movement phase relative to their cardiac cycle (φ) is computed in 246 using the timing events of valid RR and SS intervals following, for example, the equivalent process as described in 162 of FIG. 7. If either or both of the RR and SS intervals are invalid for current the loop cycle, φ is also not considered valid.

Feedback prompts in this example system 236 adapt prompt timing to account for variations in how users respond to them as well as the changes in the user's HR (pulse-period). Consider a target phase $\phi_{target}$ that, for example, represents a desired point in the user's cardiac cycle. The deviation or "error" between the valid movement phase φ determined in

246 and $\phi_{target}$ (i.e., $\phi-\phi_{target}$) is used in 248 to compute a "correction factor" (CF). The function $f(\phi-\phi_{target})$ in 248 can take on the form of a proportional-integral-derivative (PID) control loop, namely that the resulting value may be a simple fraction of the error term (proportional dependence), it may also factor in how long the movement timing error has persisted (integral dependence), and how quickly the timing error is changing (derivative dependence). All or some of these proportional, integral, and derivative dependencies can, in alternative embodiments, be included in computing the CF 248. Additionally, in certain embodiments, the associated PID gain factors can depend on the user's HR. In some embodiments, the magnitude of CF 248 can be capped so as to limit how quickly the prompt cadence can change (e.g., values that result in changes of <5 ms per cardiac cycle, or <10 ms, or <25 ms, or <50 ms).

For loop cycles with an available valid $\phi$ value from 246, the prompt-to-prompt timing interval for guiding the user's timing in attaining and/or maintaining the proper movement timing is computed in 250 as $(1+CF) \cdot RR_{avg}$; in the absence of valid information, CF is equated to zero in 248 for the current loop cycle and the prompt interval simplifies to RRavg. Hence the feedback prompts 250 function as an "adaptive" metronome for the users to pace their MSK activity cadence. The prompt intervals are modified continuously as needed using valid data to provide a rhythm and timing that brings the user's measured MSK activity into proper alignment with a targeted location relative to the user's cardiac cycle.

This exemplary system 236 serves to help the user continuously coordinate their movements even when the signals are of reduced quality. Furthermore, system 236 can accommodate signals that are not received at the processor promptly and/or consistently, and can adapt to a user's response to prompts that varies over time or relative to other users. The feedback prompts 250 can be discontinued if there is a sustained absence of valid signals beyond an acceptable "extrapolation" period.

While system 236 in FIG. 26 has been described in terms of event times associated with specific features within CV and MSK activity signals, the average HR and relative phase relationship between the signals can be determined using other methods that do not require identifying specific features within the signals. For example, Fourier Transform and cross-correlation and techniques can alternatively be utilized. Furthermore, it should be appreciated that the CF term in 248 can alternatively be computed as a function of time-values rather than phase-values. Additionally, providing feedback prompts 250 with a cadence of the aHR in the absence of artifact-free signals is also applicable to system configurations that do not include MSK monitoring.

The methods and systems discussed in the present disclosure are well suited for use in combination with exercise equipment including, but not limited to, treadmills, stationary bicycling equipment, elliptical trainers, stair steppers, and rowing machines. In addition to other relevant exemplary embodiments described elsewhere in this disclosure (e.g., FIG. 9), the system shown in FIG. 16 offers a continuous operating mode for use in conjunction with exercise equipment. The process utilizes the user's tR 154 and resulting tHR 156 for setting an initial equipment load level (LL) and prompt indicator delay time 252 and, optionally, equipment speed to support the user's cadence consistent with their tHR 254. The looping system continues similarly to the other systems described herein, with a warm-up loop that provides a transitional cadence feedback indicator 161 and continuous operating loop that provides prompts delayed from the user's cardiac cycle for properly coordinating their MSK activity 256. The aHR determined in 144 is used for toggling the feedback prompts between 161 and 256 (similar to the system of FIG. 7), as well as controlling feedback to the exercise equipment in adjusting its relevant settings. For example, the deviation ($\Delta$) between the user's aHR and the tHR 258 and the rate of change in aHR (HR-dot) 260 can be used to instruct the exercise equipment to adjust the load level (LL) 262, assisting the user to converge to the tHR. Such LL adjustments can include, for example, changes to the speed, incline, and resistance, depending on the nature of the equipment. (Not shown, in certain alternative embodiments, the time integral of $\Delta$ can additionally be included and used for adjusting the equipment load level.) These same considerations can be used in guiding the user in manually adjusting the exercise equipment, or in adjusting their own work load level (e.g., stride length, speed, bicycle gearing, etc.) whether exercising with stationary or non-stationary equipment, or independently. Information obtained from or provided to the user, such as in 154 or 262, can be though a user interface (such as shown in FIGS. 3A and 3B) that is incorporated in the exercise equipment or, alternatively, in a separate device.

Figure 16:
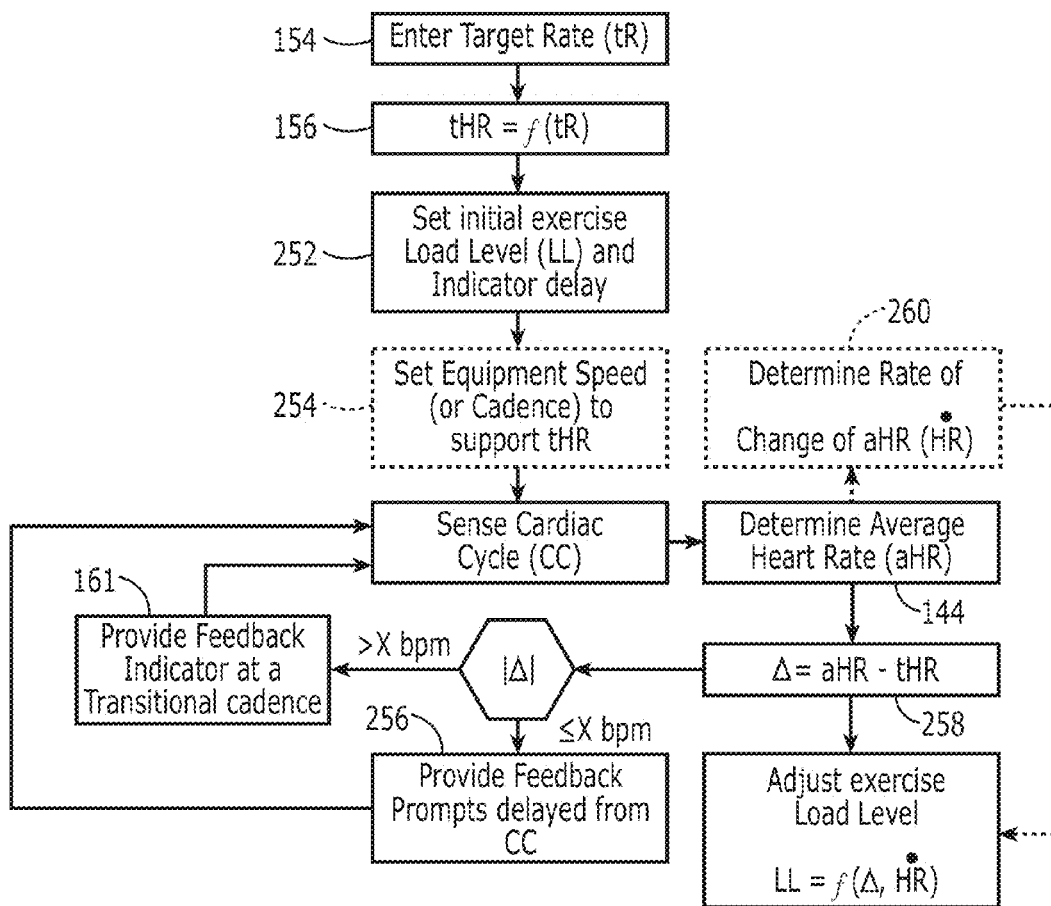
FIG. 16 is a flow chart of an exemplary system that includes the additional context of an item of exercise equipment according to an embodiment of the present disclosure.

In alternative embodiments related to the system of FIG. 16, beyond LL adjustments 262, the exercise equipment can further adjust the equipment speed (for example, belt speed with a treadmill) to support changes in the user's target rates. In yet further embodiments, the user's MSK activity can additionally be sensed and used in determining proper feedback prompt timing and/or used in adjusting the exercise equipment to support the user's activity.

Furthermore, at least one of an audible, visual, or tactile signal that is separate and distinct from the MSK movement or muscle contraction prompt can be provided as an alert or warning signal to indicate when the user is not moving accurately to the prompts. This type of signal to the user can be helpful in keeping the user's attention focused, by reminding users when their accuracy is poor for any of a variety of reasons, for example when their attention has drifted from concentrating on accurate timing.

Figure 17:
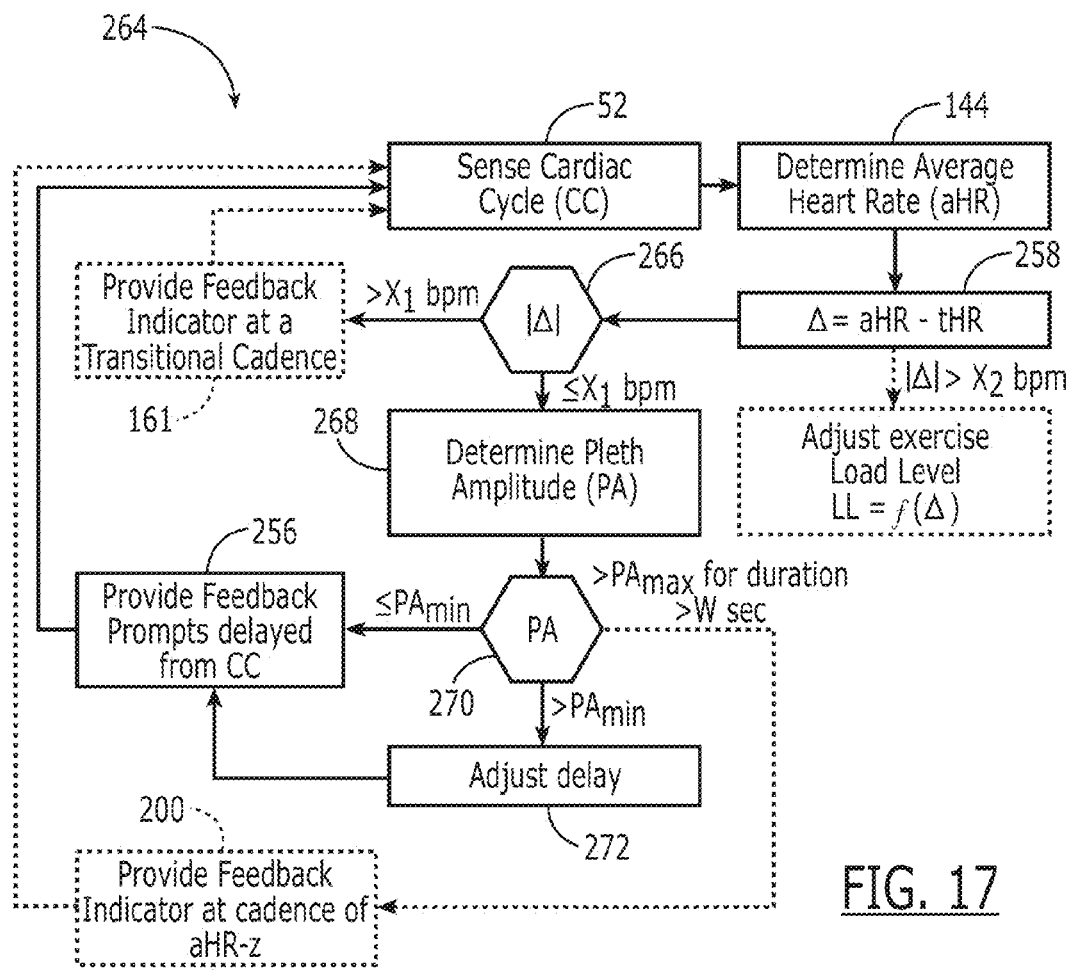
FIG. 17 is a flow chart illustrating an application of the present disclosure for optimizing a plethysmographic (i.e., pleth or PPG) waveform with, optionally, protection for inverse MCP and/or use with exercise equipment.

Systems according to the present disclosure can also be configured to monitor the user for signals indicative of their activities creating sustained periods of inverse MCP (iMCP), such as shown in the exemplary system of FIG. 17 that includes measures of the user's plethysmogram (e.g., with a PPG or impedance plethysmogram). The upper portion of system 264, (in steps 52, 144, 258, 266, and optionally 161) provide warm-up mode functionality equivalent to that of the example systems shown in the other figures. The user's CC can be sensed in 52 using an ECG signal, a plethysmogram (as will be used in 268), or other suitable means. Once the user's measured aHR 144 approximates their predefined tHR within a predefined range X BPM 266 (i.e., $|\Delta|=|aHR-tHR|\leq X$), their plethysmogram's modulation amplitude (equivalently, "pleth" or pulse amplitude, PA) is determined 268.

As can be seen in the exemplary PPG waveform 40 of FIG. 2C, the signal's heartbeat-to-heartbeat modulation amplitude (the pulse size within each R-R interval) coming from cycling arterial blood volumes in the peripheral tissues correlates to the relative timing between the user's rhythmic MSK activity and their cardiac cycle. A relatively large amplitude waveform (such as shown in FIG. 1B at the aorta) can be indicative of iMCP, while small relative amplitude (FIG. 1C) can be indicative of MCP. In this example system of FIG. 17, if PA is smaller than a predetermined threshold $PA_{min}$ in 270, the user is provided with feedback prompts 256 delayed in time from their CC by a pre-determined initial value of $\tau$ and looping continues. If the PA is greater than $PA_{min}$, but smaller than an upper bound of a pre-determined $PA_{max}$, the delay time $\tau$ is adjusted 272 automatically, or in an alternative embodiment, can be a user-selected adjustment, and prompting feedback 256 and looping continues normally. This process serves to "tune" the delay time value so as to maintain small PA values (i.e., $PA \leq PA_{min}$) indicative of MCP. If, however, the PA exceeds a predetermined value $PA_{max}$ for more than a preset duration of W sec (indicative of prolonged iMCP) according to 270, the user is guided to a cadence that differs from their aHR 144 by a pre-determined amount of z BPM 200 and the process can restart.

As noted previously, for example in FIG. 2B, cardiac-induced arterial blood pressure waves sensed peripherally are delayed in time from the timing of the arterial pressure in the aorta due to wave propagation time, while MSK-induced pressure waves can be produced in other portions of the body and/or locally depending on the activity involved. Thus the pleth sensor location (e.g., digit, forearm, forehead, etc.), the cardiac-induced wave propagation times, and the MSK activity all have an impact on the measured pulse amplitudes 268 in comparison to what is occurring at the aorta; accordingly, the details of the branching logic shown in 270 can differ from what is shown in FIG. 17. Furthermore, in alternative embodiments, the pleth morphology can be considered alone or in addition to PA for sensing the presence of iMCP in 268 and branching in 270. For example, the number of local peaks in the signal or its time derivative found within a pulse period (derived from the pleth signal or an ECG signal) can be used to distinguish differences in the signals indicative of MCP and iMCP, such as seen in PPG waveform 40 of FIG. 2C.

In certain embodiments it can be desirable to provide an operating mode in which a prompt guides movement or skeletal muscle contraction coordinated to occur at a continuously varying phase of the cardiac cycle. Such a mode can be used to evaluate the physiological effect of movement or skeletal muscle contraction coordinated across different phases of the cardiac pumping cycle (e.g., during a calibration mode such as in FIG. 7 or 8); used as a mode that reliably prevents prolonged continuous periods of iMCP; or in another example, used in a periodic or continuous basis to enhance perfusion to the different muscle groups (myocardial or peripheral) or cerebral tissues if different targeted tissues do not otherwise benefit from the same MSK timing.

Figure 18:
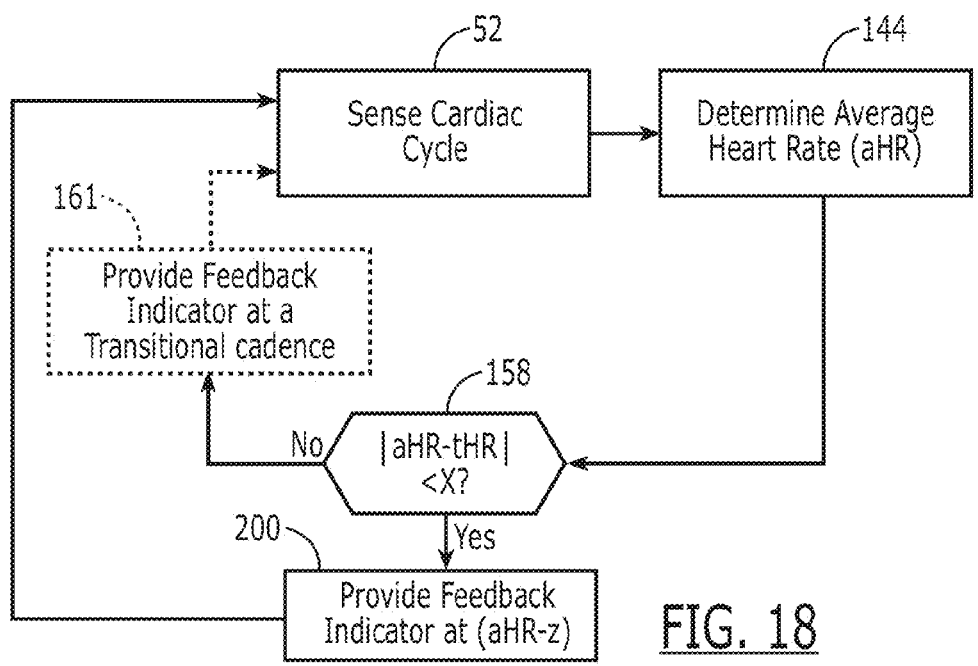
FIG. 18 is a flow chart illustrating a looping cycle of sensing the user's CC and providing prompts with a cadence at a set difference from the HR according to the present disclosure.

Such a continuously varying-phase mode is shown in the system of FIG. 18. After sensing the user's cardiac cycle 52, their aHR 144 is compared to the tHR to select 158 feedback indicators 200 or (optionally) 161 for providing timing to the user for coordinating their MSK activity. While the user's absolute aHR-tHR difference is beyond a predetermined tolerance value of X BPM, the system loops with an optional transitional cadence prompt provided to the user; when the difference is within the tolerance X, the system provides feedback prompts at a cadence of aHR-z, where z can be a predetermined fixed aHR-independent value (positive or negative). In alternative embodiments, the prompt timing can be calculated as a function of aHR or, alternatively, HR.

According to this system of FIG. 18, the user times their MSK activity to occur at the cadence of the feedback prompts, causing the MSK phase with respect to their CC to vary smoothly and continuously. By way of examples, if a user's aHR is 150 BPM and their activity is timed to occur with a cadence of 147 per minute (z=3/min), 140 per minute (z=10/min), or 155 per minute (z=−5/min), their MSK phase with respect to their cardiac cycle will vary across the full phase range (i.e., 0-100%, equivalently 0-360 deg) over, respectively, a 20 second period (i.e., 150-147/min=3/min=20 sec period), 6 second period, or 12 second period. In certain applications, the activity cadence is targeted to occur at a fraction of the user's aHR (e.g., 1:2, 1:3, etc.); accordingly, feedback indicator 200 can be enunciated on every cardiac cycle, or alternatively every $2^{nd}$ cycle, $3^{rd}$, cycle or greater as appropriate for the MSK activity.

Figure 19:
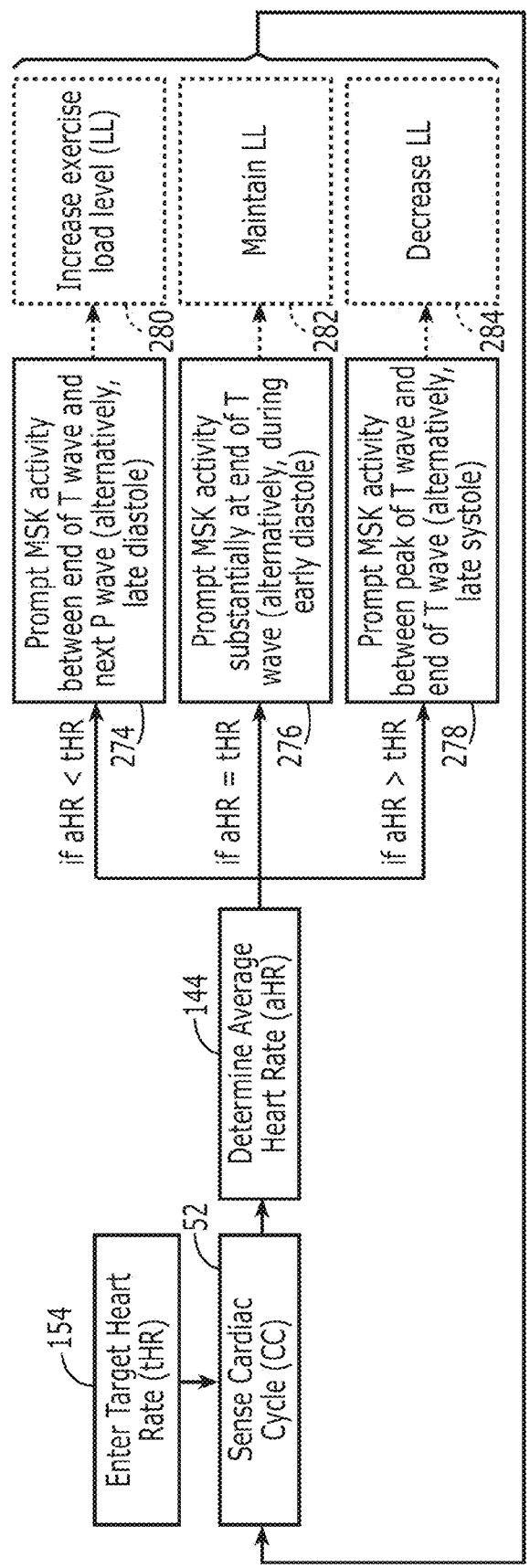
FIG. 19 is a flow chart illustrating a process facilitating maintenance of MCP during changes in HR, with an ECG sensor, according to an embodiment of the present disclosure.

FIG. 19 charts another exemplary continuous mode system according to the current disclosure. In the system of FIG. 19, an ECG signal is used to sense the user's cardiac cycle 52, aHR 144, and for identifying the proper timing of feedback prompts (274, 276, and 278). When the aHR 144 is equal the tHR from 154 (or, in an alternative embodiment, within a pre-specified tolerance), the feedback prompt 276 to guide timing of the user's activity is made to substantially coincide with the end of the ECG T-wave (i.e, substantially during the early diastolic period). When the aHR 144 is less than the tHR from 154, the feedback prompt 274 is made to occur between the end of the T-wave and next P-wave (i.e., substantially during late diastole). Lastly, when the aHR 144 is greater than the tHR 154, the prompt 278 is made to occur between the peak and end of the T-wave (i.e., substantially late systole). As shown in FIG. 19, additional instructions to, respectively, maintain the user's exercise load level (LL) 282, increase LL 280, or decrease LL 284 can optionally be provided to the user or in controlling settings of exercise equipment manually or automatically to assist the user in maintaining a comfortable HR range. Timing one's MSK activity (and the resulting MCP) essentially at the timing of aortic valve closure (e.g., 12 in FIG. 1A, or 30 in FIG. 2A) can facilitate maintaining the user's HR. Moving the timing earlier in the R-R interval can trigger the next R wave to occur sooner, thus increasing the aHR; conversely, moving the MSK and MCP timing later in the RRI can delay the subsequent R-wave, thus slowing the HR.

Figure 20:
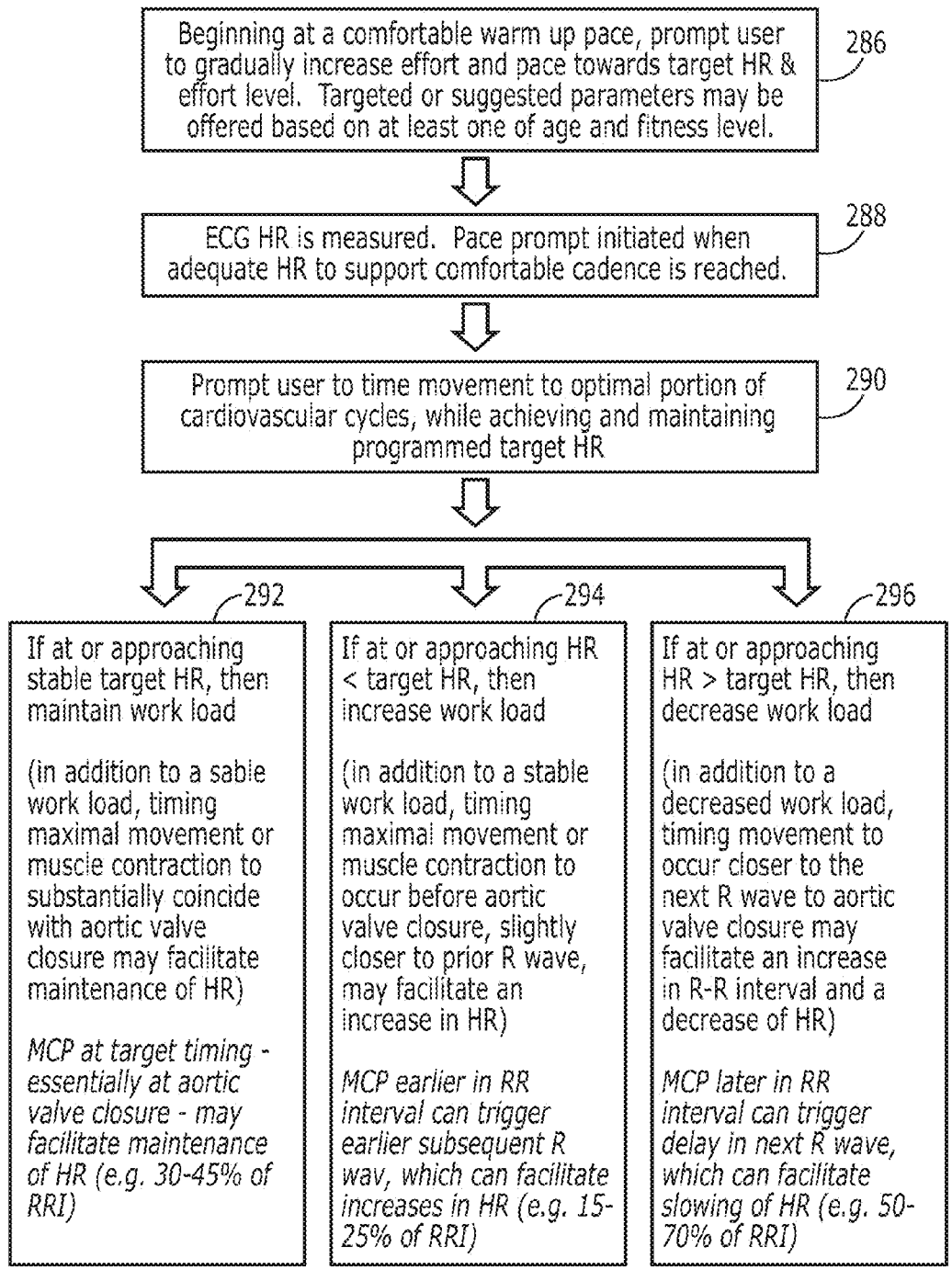
FIG. 20 is a flowchart illustrating a process for initiating and maintaining MCP according to the present disclosure according to an embodiment of the present disclosure.

FIG. 20 describes an exemplary exercise plan comparable to the system shown in FIG. 19. The exercise begins in 286 with a warm-up pace and feedback information for gradually increasing effort and pace towards a target HR. The user's ECG based HR is measured in 288 and pacing prompts initiated when the HR reaches a comfortable cadence according to the user's activity. The exercise proceeds with continuous prompting 290, with its timing based on the user's HR relative to the target HR as described in 292, 294, and 296.

Figure 21:
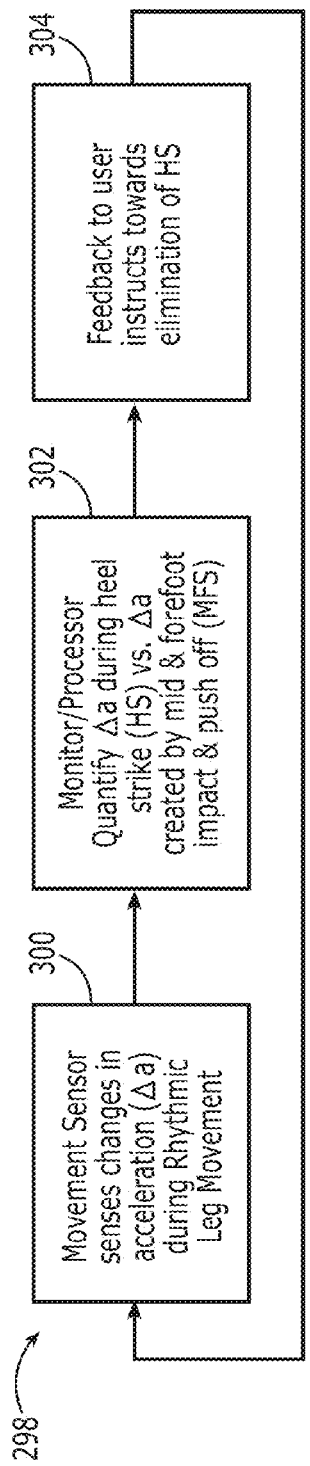
FIG. 21 is a flowchart illustrating a process for determining foot strike location and providing feedback to a user to correct foot strike location according to an embodiment of the present disclosure.
Figure 38A:
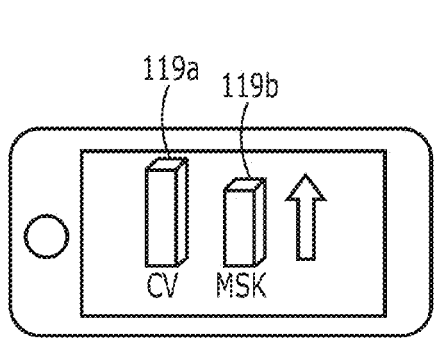
FIGS. 38A and 38B are illustrations of exemplary visual feedback interfaces according to the present disclosure.
Figure 38B:
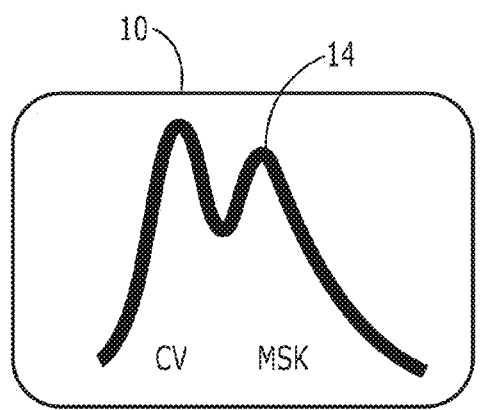
Figure 39:
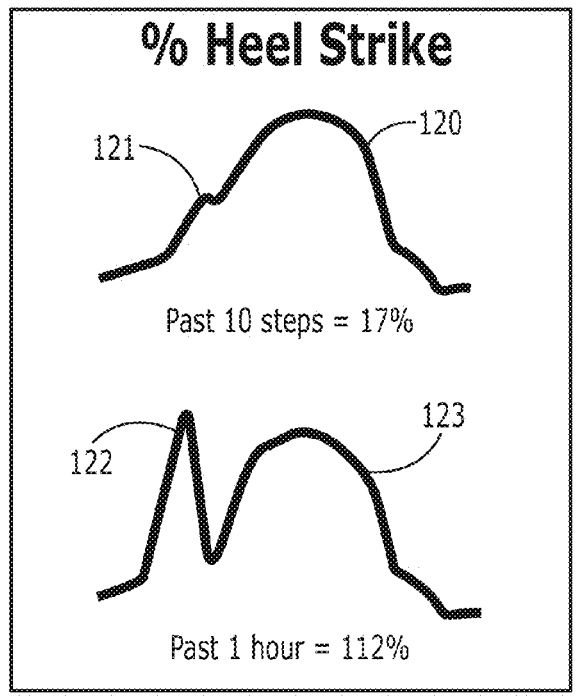
FIG. 39 is an illustration of another exemplary visual feedback interface according to the present disclosure.

FIG. 21 provides an exemplary system according to the current disclosure for monitoring a user's movements and detecting the presence or absence of heel striking (HS) during rhythmic leg movements (e.g., during running or walking). System 298 includes a movement sensor comprising, or example, an accelerometer attached to a user's chest or elsewhere on their body; or in other examples, pressure or force transducers located in the user's shoe(s) such as depicted in FIG. 38, alternatively located within a treadmill or stepper, or other suitable location. Signals from 300 are used to monitor and interpret the signals to ascertain if the user's heels are striking the ground with excessive force, or if the user is, conversely, mid-foot or forefoot striking 302. FIG. 39 exhibits exemplary accelerometer or foot force signals indicative of heel striking (lower waveform), apparent by the "spiked" portion 122 on the left hand side of the signal, caused by the rapid change in acceleration and force when the body first strikes the ground with the heel. Forefoot and mid-foot strikes lack this large spike, as seen in the upper signal example in FIG. 39 and the much smaller or absent spike 121. If the user's signals are indicative of HS, the system 298 provides feedback 304 to user instructing them to modify their movements to eliminate the HS and thus further improve the quality of their movements in achieving MCP.

Figure 22:
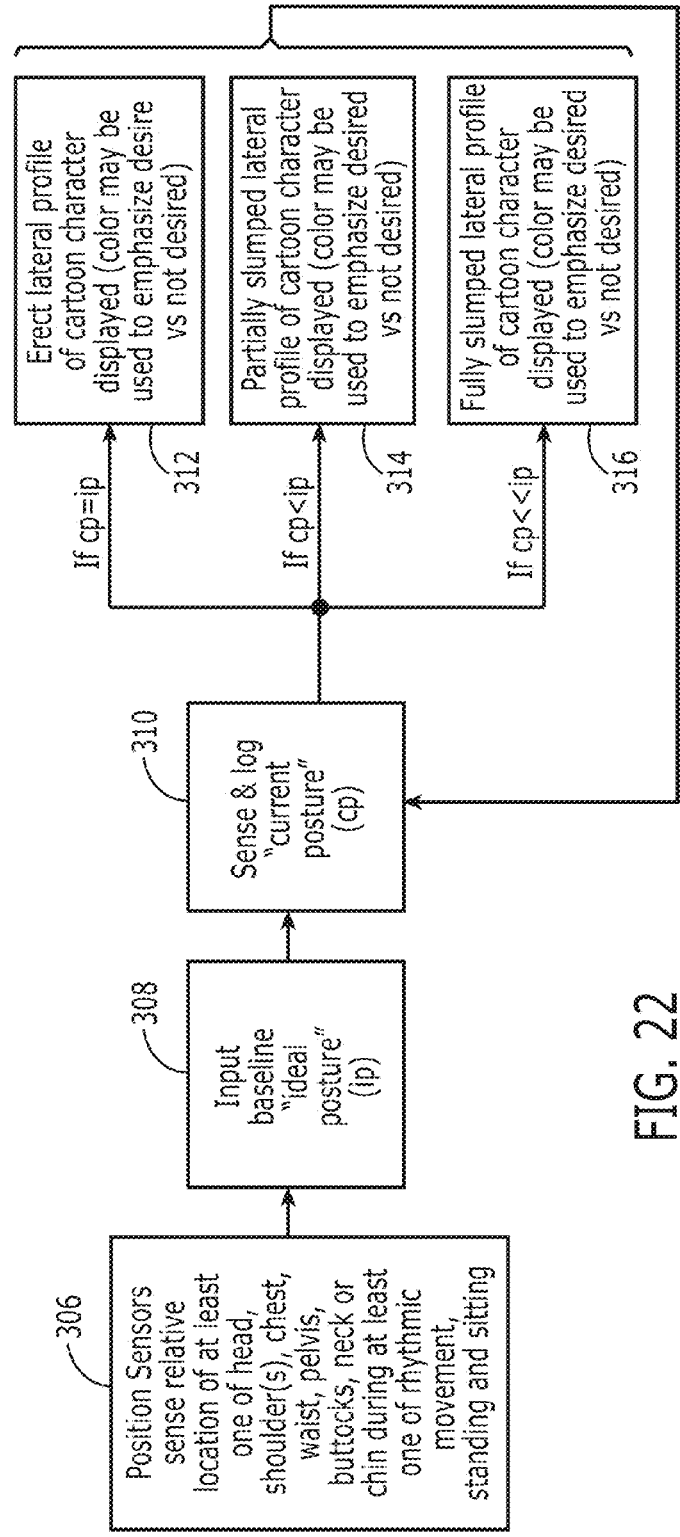
FIG. 22 is a flowchart illustrating a process for determining posture position maintained during physical activity, and for providing feedback to enable a user to approximate a target posture according to an embodiment of the present disclosure.

The system of FIG. 22 is designed to provide ergonomic posture feedback to the user according to the current disclosure to further assist the user in achieving an effective MCP. The system of FIG. 22 includes position sensors 306, comprising at least one of an accelerometer, gyroscope, or camera. The position sensor(s) detect the location of one or more of the user's head, shoulders, chest, waist, pelvis, buttocks, neck, or chin during rhythmic movement, standing, and/or sitting. The user's current posture (cp) 310 is compared to their baseline ideal posture (ip) 308 and used for selecting the proper feedback (312, 314, or 316) before looping and iterating the sensing process at step 310. The baseline ideal posture 308 can comprise a universal set of relative values of the position sensor signals 306, or can be empirically determined from the user's signals 306 obtained while they are instructed to maintain a good posture during a baseline measurement process. If cp=ip (or in a an alternative embodiment, is within a predefined tolerance), the user feedback can comprise an icon such as an erect cartoon character exhibiting "good" posture 312. If the posture is mildly poor (cp<ip) 314, a different icon, such as partially slumped cartoon character, can be displayed as feedback to the user. When the user's posture is sensed to be more extremely poor (cp<<ip) 316, the feedback icon can comprise a fully slumped cartoon character. In each case, color can additionally be used to emphasize desired versus not-desired characteristics and overall postures.

Further embodiments of the systems contemplated by the applicants guide the user to self-adjust their timing by providing separate and distinct audio, visual or tactile prompt signals for each of the following: (1) a signal that represents the MSK activity prompt (desired timing) and (2) a clearly different and recognizable signal that represents the actual MSK activity timing. In these embodiments, the user attempts to move at the prompted timing, but also assesses the feedback to see if the timing of the actual prompt and timing of the true MSK activity occur simultaneously or nearly so. In some embodiments the prompt signal for the desired MSK activity timing and the feedback signal for the actual MSK activity timing remain separate. In other embodiments, a third distinct audio, visual or tactile signal confirms accurate timing when the desired timing signal and the actual timing signal occur at very similar or identical times. In this case, the user attempts to maintain that unique third timing signal, rather than the two separate (actual and desired) timing signals. For example, an audio signal of one tone (e.g. at a first pitch) can provide the MSK activity prompt, while a second tone (e.g., at a second pitch) provides an indication of actual MSK activity timing, but these two tones are replaced by a single repeating third tone at the substantially overlapping desired and actual timing that also indicates that the target timing has been substantially achieved (e.g., a distinct third tone is at yet another pitch; or a tone with more resonance, for example). The third tone can be distinct from the first and second tones, or can be a combination of the two tones that create a distinct and pleasant third tone. In one example embodiment where visual feedback is utilized, one color can indicate moving too early, another can indicate moving too late, and a third color can indicate accurate moving. The third color can be a distinct color or a combination of the two colors (e.g., yellow too slow, blue too fast, green for accurate timing).

In alternative embodiments of the system, information on the quality and relative quantity of MSK blood pumping can also be provided to the user. In an example embodiment, an audible "first beat" can be provided in order to prompt the user's MSK movement or muscle contraction cycle tempo, while an audible "second beat" can represent the magnitude of the diastolic or MCP wave, with its audible volume relative to the first beat representative of the magnitude of the diastolic pressure or flow wave relative to the systolic pressure or flow wave. Alternatively, the quality, duration, or pitch of the prompt can be otherwise altered to indicate the magnitude of MCP. These types of qualitative and quantitative feedback can improve motivation and confidence for the user. It might also provide information to the user as to which MSK activities are most impactful in creating effective MCP. In another alternative embodiment, a visual display can provide feedback as to the magnitude of MCP achieved and guidance as to how the user can improve the timing, magnitude, or quality of movement, muscle contraction, or muscle relaxation.

Figure 23:
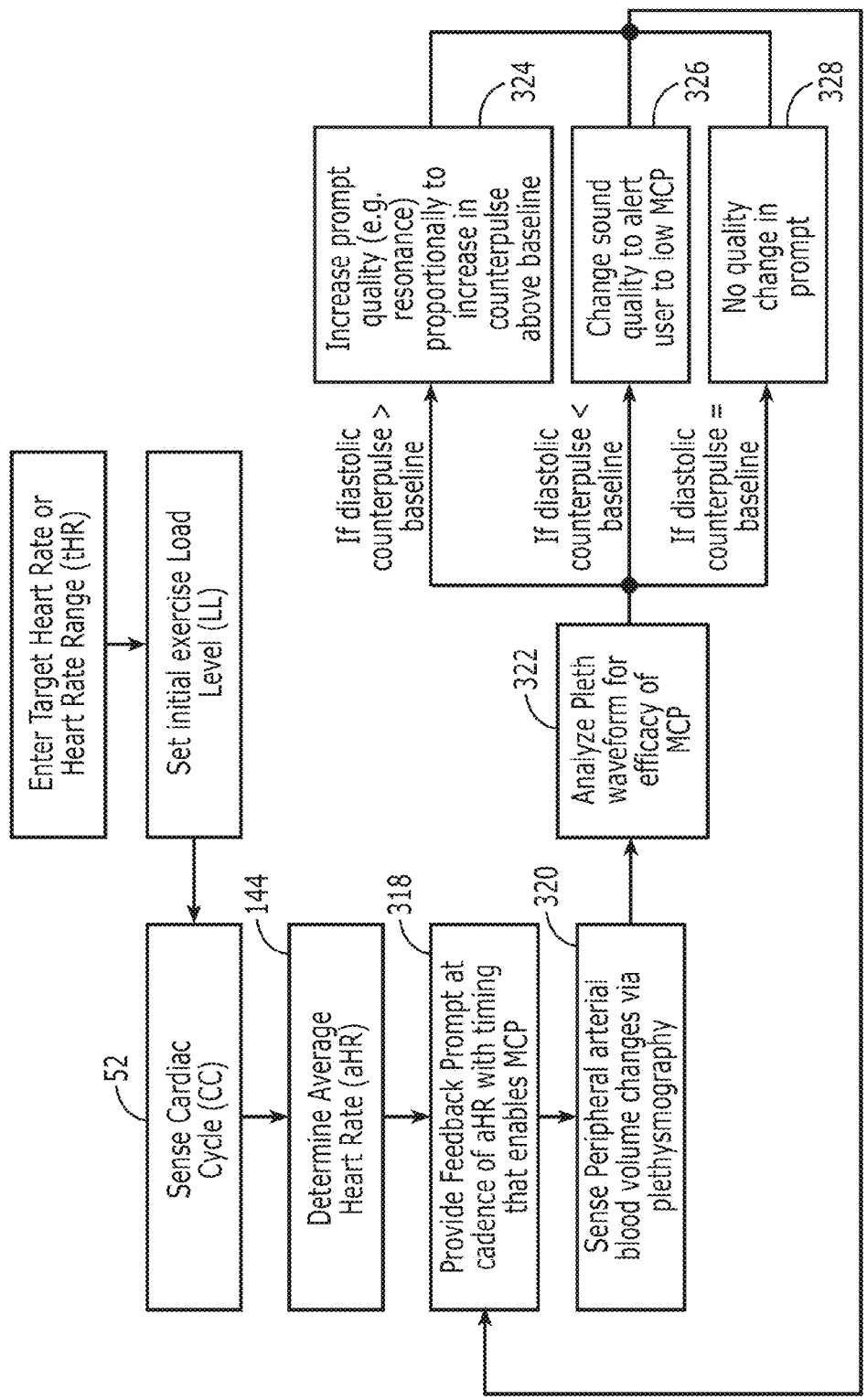
FIG. 23 is a flowchart illustrating cadence prompt optimization via a change in prompt used to coach a user to adjust step timing, according to another embodiment of the present disclosure.

An example of such a system that provides audible pacing feedback for enabling MCP that further includes dependent sound characteristics for communicating the quality of MCP is shown in FIG. 23. According to similar continuous operating mode systems described earlier in this disclosure, the process includes sensing the user's cardiac activity 52, determining their aHR 144 and providing feedback prompts for assisting the user in properly coordinating their MSK activity to enable MCP 318. Additionally, the system of FIG. 23 senses and analyzes the user's plethysmographic (e.g., PPG) waveform signals 320 for determining the efficacy of the counter pulsations 322. Considering FIGS. 1A, 1B, and 1C, efficacy in step 322 is assessed by comparing the differences in the diastolic pulse amplitude (e.g, 14 and 20) relative to its pulse height appearance when the user is not moving (e.g., 20 as a baseline). If in 322 the diastolic pulse height remains comparable to its baseline value (328), the provided feedback prompt's nominal sound "quality" is used (i.e., nominal pitch and/or resonant characteristics). If in 322 the diastolic pulse is assessed to decrease sufficiently beyond the baseline (326), appearing more like FIG. 1B than 1A or 1C, the system changes the sound feedback prompt quality (e.g., decreases pitch and/or resonant characteristics in a discordant manner) to indicate a low level of MCP or potentially iMCP is present; if per 322 the diastolic counterpulse is strong, such as FIG. 1C, the pacing feedback prompt sound quality 324 is increased proportional to the degree of improvement beyond baseline. While FIG. 23 utilizes the sound quality as a means to communicate information about MCP efficacy to the user, analogous approaches can be used for visual or tactile prompts, changing the nature of the feedback in a manner that allows the user to obtain information to modify their or maintain their movements.

Alternative embodiments of the system and method can be configured to enable the user to time additional rhythmic physiological functions in coordination with specific targeted portions of the cardiac cycle or with rhythmic MSK activities. In one example, the timing of respiration can be coordinated with target elements within the cardiac cycle. Inspiration creates negative pressure in the thorax in order to draw air into the lungs. For example, this negative intrathoracic pressure can be coordinated with regularly occurring cardiac diastolic cycles in order to improve cardiac filling from the venous system. The negative intrathoracic pressure of inspiration, when timed to coincide with diastole, can also impact coronary artery blood flow, myocardial perfusion, and oxygenation. On the other hand, forced expiration causes an increase in intrathoracic pressure, which can, for example, be timed, relative to systole, in order to assist the systemic pumping function of the heart's left ventricle.

In certain embodiments of methods and systems in this disclosure it may also be desired to provide a mode that limits the amount of time that a specific feedback prompt timing or phase is used prior to changing or recalibrating the timing. This may offer a level of safety to the user, or help with cycling through targeted muscle groups in a timely manner. The system of FIG. 18, for example, necessarily varies the user's $MSK_\phi$ by pacing them at a cadence that differs from their HR. Alternatively, a system such as shown in FIG. 14 or FIG. 26 can readily be used to vary the user's $MSK_\phi$ in a pre-determined manner by changing the targeted phase programmatically. In yet another example, FIG. 24, as described more fully in below, shows a system that combines warm-up, calibration, and continuous operating modes with an included provision to repeat the calibration if certain pre-defined conditions are met.

Figure 24:
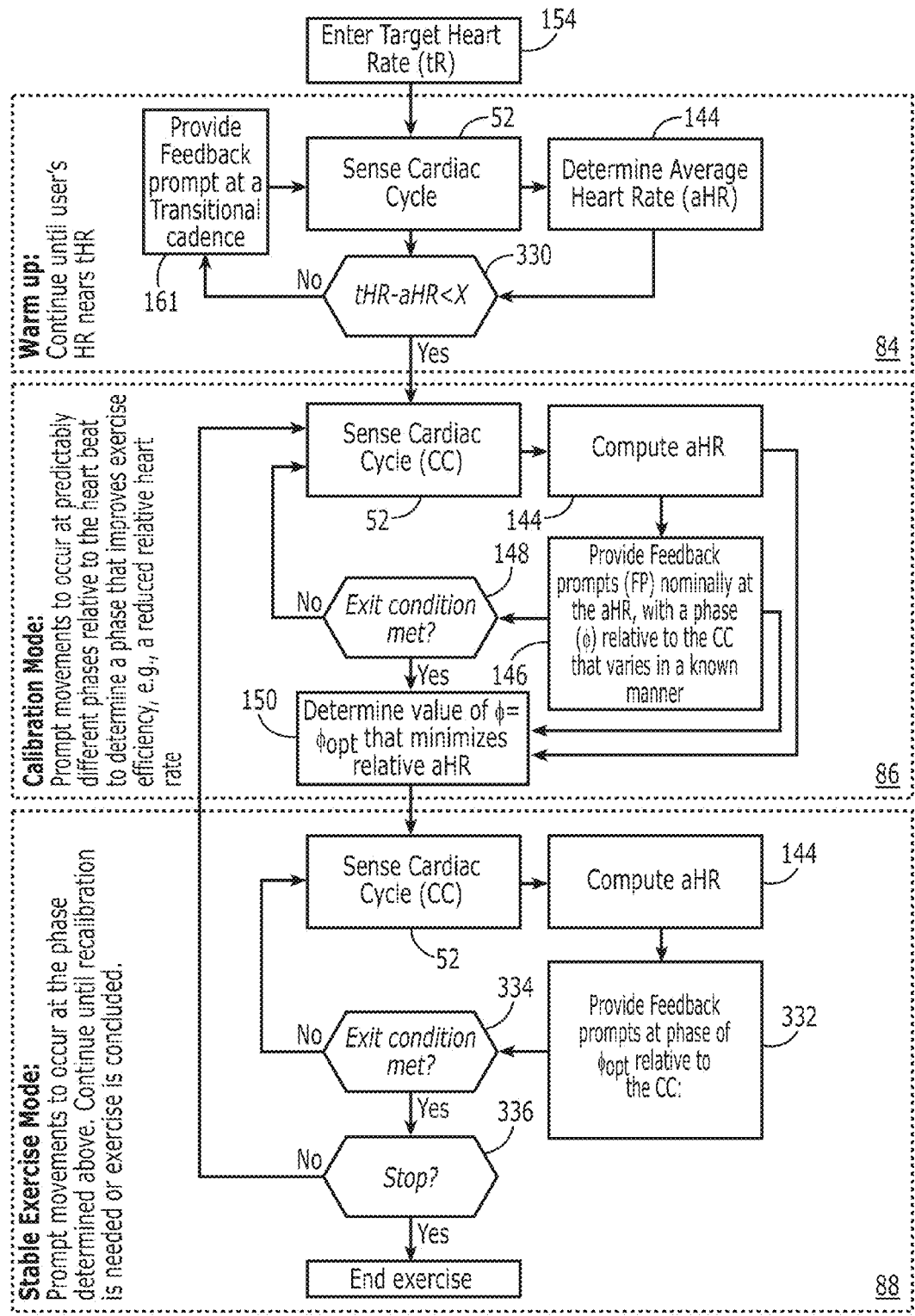
FIG. 24 is flow chart of an exemplary system based on monitoring only the CC illustrating the combination of warm-up, calibration, and continuous operating modes described previously herein.

The process of FIG. 24 begins in an exemplary warm-up mode 84, comprising steps of sensing the user's cardiac cycle 52 and aHR 144, and looping with feedback pacing prompts 161 at a transitional cadence until the aHR 144 falls within the predetermined tolerance X BPM of the tHR 154. When the aHR 144 is within the target range, the process continues with an exemplary calibration mode 86 that provides cadence prompts 146 nominally equivalent to the user's aHR, though with a phase φ relative to their CC that is made or otherwise allowed to vary in a known manner. After continuing in this loop for a sufficient period 148, the optimal phase ($\phi_{opt}$) that minimizes the user's aHR is determined 150 and used in a subsequent continuous operating mode 88. Comparable to the continuous modes of FIGS. 6, 13, 14, and 26, the exemplary configuration shown here senses the user's CC 52, determines their aHR 144, and provides feedback pacing prompts 332 to the user for properly coordinating their activity timing for achieving continuous MCP by utilizing the $\phi_{opt}$ delay identified in 150. The continuous mode 88 continues until a pre-determined exit condition 334 is met. Condition 334 can comprise a period of time (e.g., 30 min, 60 min, 120 min, etc.), a prolonged and meaningful change in aHR 144 (e.g., more than 20 BPM from the calibration condition for more than 10 minutes), a change in the sensed activity, using for example an MSK sensor (not shown), or any other characteristic suggestive that the optimal phase may differ from what was determined previously. This exit condition 334 can alternatively be invoked by the user manually. If the exit condition 334 is met, subsequent condition 336 is provided to optionally stop the exercise entirely or repeat the calibration mode process by looping back to step 52 in calibration block 86. In an example of an alternative embodiment of FIG. 24, warm-up mode 84 can be bypassed, beginning with calibration mode 86 followed by continuous mode 88. In yet another example, the calibration mode 86 can be bypassed if, for example, the value of $\phi_{opt}$ had been determined previously. Accordingly, and as was described with FIG. 4, modes 84, 86, and 88 can be used optionally. FIG. 24 further exemplifies how the various "building blocks" of the various modes (e.g., warm-up, calibration, operating modes) can be combined into a more complete system according to the present disclosure.

In some embodiments it may be desired to provide at least one of an audible, visual or tactile MSK movement or muscle contraction prompt at the HR, without automatically timing the prompt accurately to the desired location within the cardiovascular pumping cycle, but instead enabling the user to intentionally adjust the timing of the prompt, relative to the CC, directly or indirectly, via user controls within the user interface. In certain embodiments, the user can be allowed to adjust the prompt timing within a pre-set range of possible phases relative to the cardiovascular pumping cycle. For example, when an ECG based monitor is used, the prompt will initially occur with a specific relationship to the R-waves, the user can be enabled to then adjust the prompt, directly or indirectly, via a manually or verbally controlled user interface, across a pre-set range of delays relative to that R-wave. The delay can be adjusted directly (e.g., between 100 and 200 ms, for example); or the delay can be calculated by a formula into which the user inputs; or it can be a relative delay that the user can adjust (e.g. between 25% and 45% of the RRI, for example); or the HR range can be chosen by the user wherein the chosen HR range has been linked to a particular prompt delay; or the exercise mode can be selected by the user wherein the specified mode may typically occur within a natural range of cadences, and therefore may be linked to a particular prompt delay (e.g., on a treadmill, in one example, a user can select "walk", thereby automatically setting the initial track speed 2.0 mph and the prompt delay at 200 ms from the R-wave, or can choose jog, thereby setting the initial track speed at 4.0 mph and the prompt delay at 175 ms from the R-wave, or can choose run, thereby setting the track speed at 6.0 mph and the prompt delay at 150 ms). In certain embodiments, the user can be instructed to adjust prompt in order to optimize the subjective feel of the exercise (e.g., easier to perform or easier to breathe comfortably or rhythmically with movement) or the user can be instructed to vary the prompt in order to achieve optimization of blood flow to specific areas during the activity. In other embodiments, the prompt may be adjusted to occur at specific locations within the CC by the user. User-controlled prompt timing adjustments such as these may or may not be used in conjunction with movement sensors.

In certain embodiments of the system, the cardiac cycle is monitored via at least one of the following: electrically with an ECG FIG. 2A; optically via peripheral PPG FIG. 2C that measures pulsatile changes in light absorption by cycling blood content in tissues; optically via video monitoring of skin color changes throughout the CV cycle; via tissue ultrasound (e.g., long axis ultrasound); via tissue Doppler (e.g., laser Doppler or Doppler ultrasound); via electrical impedance (e.g., cardiograph or plethysmography); via thermal IR imaging; via sonar; via strain-gauge plethysmography; via photoelectric plethysmography; via cardiac auscultation; via non-invasive peripheral vascular pressure sensors (e.g., applanation tonometry); via oscillometric devices; and, via other non-invasive blood pressure wave monitors. Some embodiments can require proximity to skin or general skin contact (e.g., both contact and non-contact ECG electrode technologies can be used with this system).

Figure 30A:
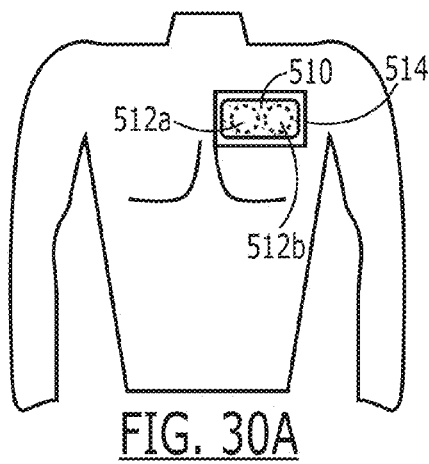
FIGS. 30A-F are illustrations of exemplary ECG electrode configurations, according to various embodiments of the present disclosure.
Figure 30B:
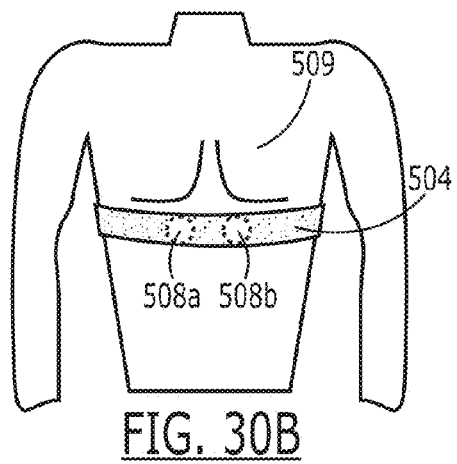
Figure 30C:
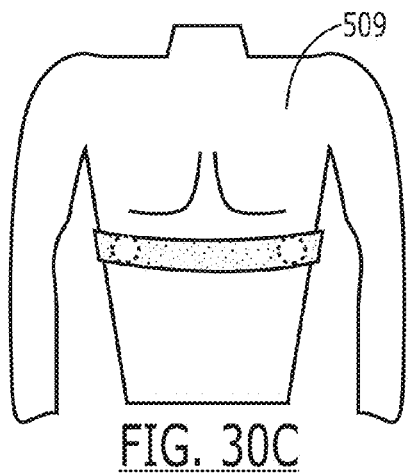
Figure 30D:
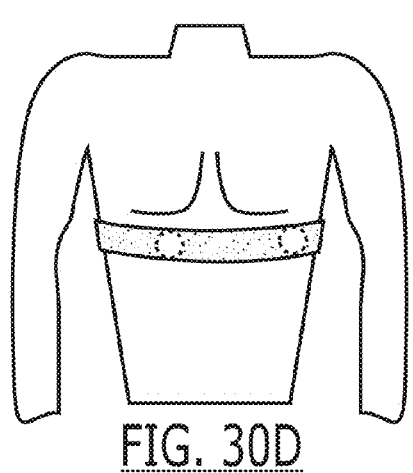
Figure 30E:
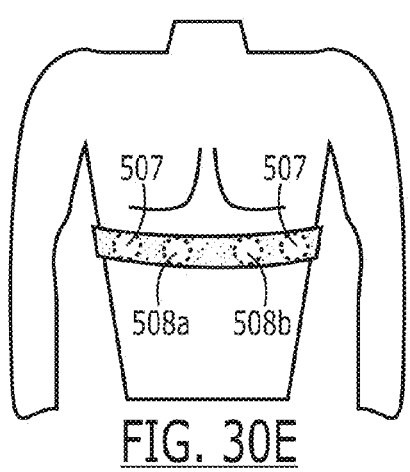
Figure 30F:
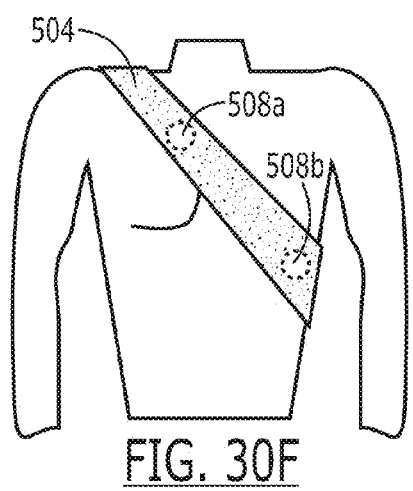
Figure 32A:
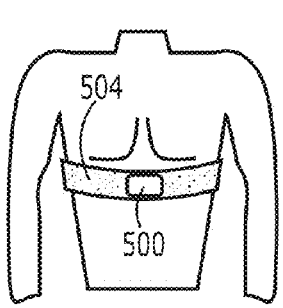
Figure 32B:
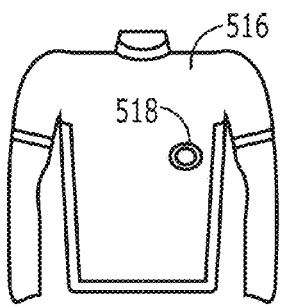
Figure 32C:
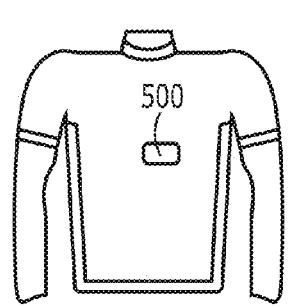
Figure 32D:
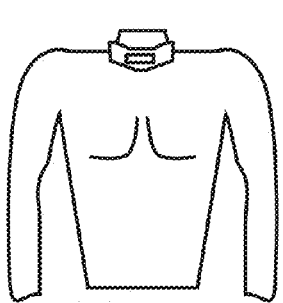

In certain methods and embodiments of the system, the cardiac cycle timing and characteristics can be monitored via an ECG sensor, wherein electrodes for detecting electrical activity of the heart, with or without adjacent integrated circuitry, and with our without integrated movement MSK activity monitors (e.g., accelerometers, EMG, etc.), can be included within a chest strap system FIGS. 30B-F, FIG. 32A, can be integrated into or attached to clothing 32B-C, accessories FIGS. 32 D, G, H, or electronic devices FIG. 27 or electromechanical equipment FIGS. 36, 37, 47, 48, can be held in the user's hands 112a,b (e.g. gripping an electrode with each hand); can be integrated within or attached to one or more patches 514 adherent to the skin FIG. 30A, can be integrated with the surface of the skin 509 (e.g. tattoo or weave) or implanted beneath the surface of the skin (alternatively, FIG. 30A can represent monitors fully or partially implanted beneath the surface of the skin of the user), or can be integrated with jewelry around one or more of the wrists 513, arms 512, legs, ankles 542, low across the neck FIG. 32D, or attached permanently or removably to clothing as an accessory 518. In certain embodiments of this disclosure, sensors in contact with the neck 515a, 515b, FIG. 32D or chest 510, 504 of a user can also be used to identify and log data on other physiological activities that can easily be sensed from those locations (e.g., accelerometry, sensing electrodes, auscultation, ultrasound, etc), such as coughing, sneezing, snoring, yelling, etc.

FIG. 30 are also illustrative that methods and embodiments of the disclosure that use ECG to monitor the CV pump cycle, can be configured to monitor different ECG leads. Certain leads can be preferred for ease of identification of the pump cycle (e.g., R waves) during physical activity, while certain leads (e.g., CC5, CM5 illustrated in FIGS. 30C, 30F respectively) can be helpful in identifying myocardial ischemia (e.g., changes in the ST segment of the ECG). ST segment depression, particularly when evident in certain leads that best reflect ventricular wall electrical activity, can represent myocardial ischemia. ST segment morphology can be subject to motion artifact during MSK activity, and the degree of ST segment artifact seems to be related to both activity and individual anatomy, including soft tissue volume beneath the electrodes, skeletal muscle mass and activity beneath the electrodes, and cardiac rotation (e.g., natural position of the heart in the thorax for that individual). Certain embodiments of the disclosed method and device can be configured with leads and programmed algorithms differentiate ST depression likely to be caused by movement artifact from ST depression that may be more likely to be caused by ischemia. Other embodiments can be configured to identify CV rhythm or electrical conduction abnormalities.

For applications that use exercise equipment 566, Figs. A-F, 49, non-contact cardiac sensing techniques (ECG, PPG, etc.) may offer more convenience, and are accordingly anticipated by the applicants.

Figure 50:
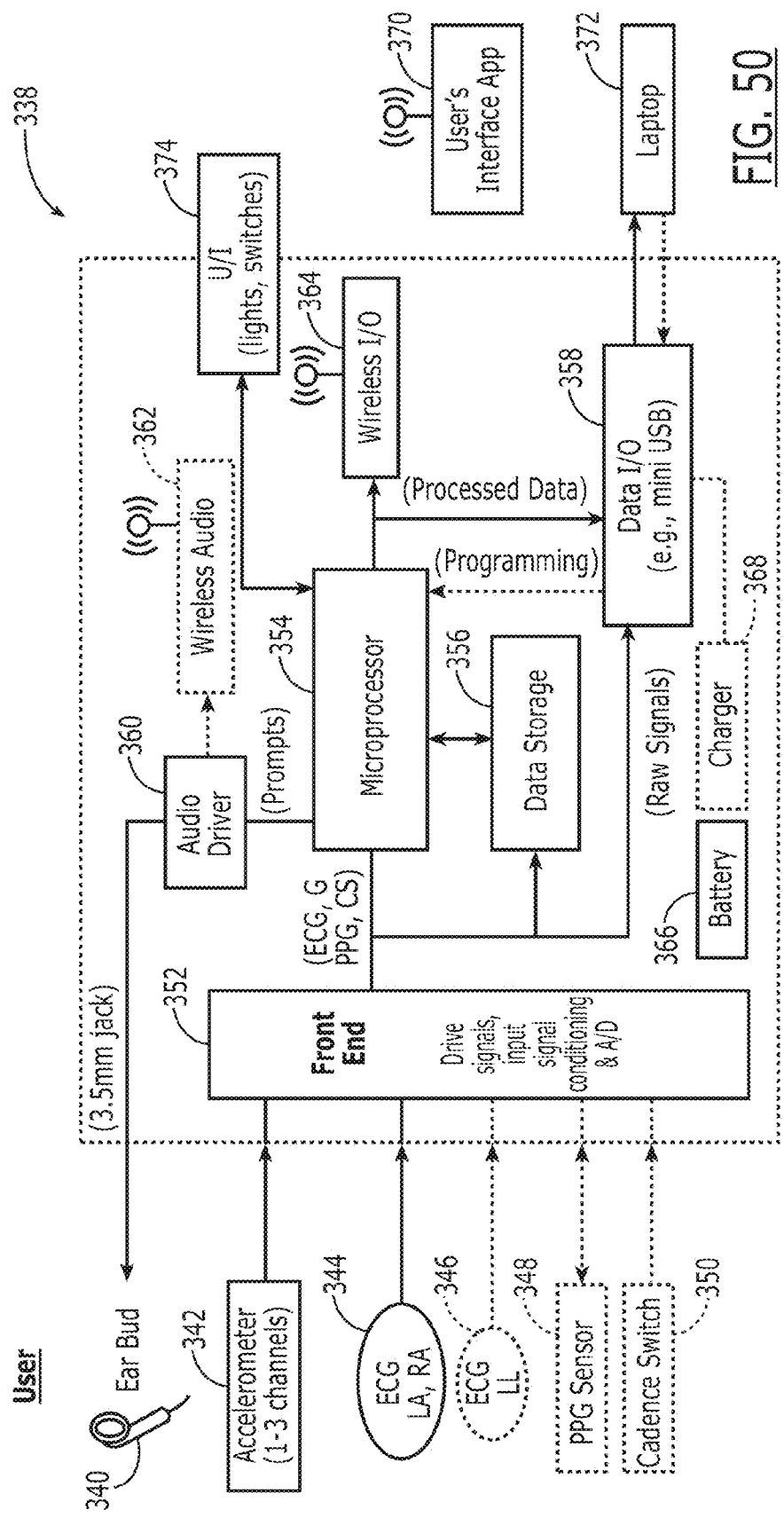
FIG. 50 is a block diagram of an exemplary embodiment of an electronic configuration according to the present disclosure.

FIG. 50 shows a block diagram for an exemplary electronics system according to the present disclosure. Shown to the left of system 338, are transducers for detecting the user's CC (a pair of ECG electrodes 344 to provide single lead operation, optionally a third ECG electrode 346, a PPG sensor 348 that can be used instead of or in addition to the ECG 344), and MSK signals (accelerometer 342; optional cadence switch 350 or other comparable device for use with external equipment for sensing the user's rhythmic activity, such as a crank sensor on a bicycle or magnetic switch on the rotor of an elliptical exercise machine). Also shown on the left is a small speaker, such as an ear bud 340, for the user to receive audible feedback prompts for timing their activity in accordance to the present disclosure. The signals from the MSK and CC transducers interface to system 338 via "front end" 352, in accordance to the individual transducer requirements (e.g., power; current drive; and signal pre-conditioning that may include filtering, amplification, multiplexing/de-multiplexing, etc.). Front end 352 further includes digitization of the resulting received signals. These digitized signals are communicated via signal lines to microprocessor 354, data storage 356, and to data input/output (I/O) 358 for optional communication to an external device such as computer 372. Microprocessor 354 provides further processing and analysis of the signals for detecting signal features and characteristics (e.g., R-wave detection, R-R interval and HR determination, MSK event timing, $\tau$ and/or $MSK_\phi$ determination, etc.) and computation and control of feedback prompts, according to the systems and methods described in this present disclosure. Feedback prompt information as determined by 354 are communicated to audio driver 360 for creating sounds delivered to the user via ear bud 340 or, optionally, via wireless audio output 362. Additional processed results from microprocessor 354 (e.g., aHR, MSK, visual feedback cues, etc.) can be sent to wireless I/O 364 and/or wired I/O 358 for external control and/or feedback devices, external data and/or graphical display via user interface 370, for data logging, or for other functions as needed. Microprocessor 354 can be controlled and/or programmed via data I/O 358, user interface (U/I) 374 and/or wireless interface 364 and 370. U/I 374 can include switches and/or lights, icons or displays for providing information (e.g., device status) to the user and as an input for setting operating conditions and options. System 338 can be powered by battery 366 and/or through the data I/O port 358, and can optionally include a battery charger 368.

Figure 29A:
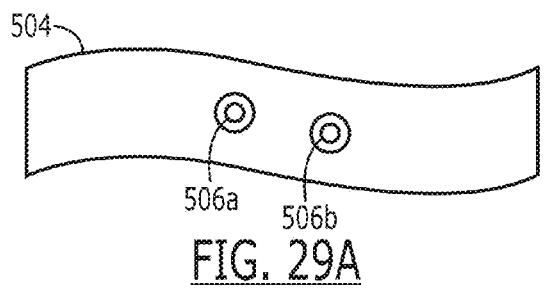
FIGS. 29A-B are illustrations of the front and back of a chest strap for receiving the sensor electronic housing of FIGS. 28A-D.
Figure 29B:
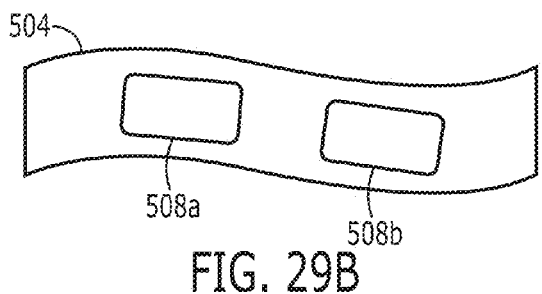

FIGS. 28A-D show various views of a removable monitor device 500, with a plurality of conductive connecting elements 502a, 502b, etc. In one embodiment, device 500 comprises a case in which are disposed an electronics board (e.g. FIG. 50) and at least two conductive connecting elements 502a, 502b, etc. which enable data transmission when removably securing device 500 to a strap 504, article of clothing 516, adhesive patch 514, accessory (FIGS. 31, 32D, G, H), etc. In other embodiments, in addition to or as an alternative to the above, device 500 can contain devices that generate and sense reflected PPG signals for measuring pulse or pulse oximetry, movement sensors (e.g. accelerometers, gyroscopes, pressure sensors), audio processors; speakers or audio output devices; tactile feedback output to the user (e.g. vibratory signal on skin to set cadence for MCP). Connecting elements 502a, 502b, etc. can also be used for data transmission, anchoring and charging the device. FIGS. 29A-B are views of a strap 504, such as for securing around the chest of a user, having connecting elements 506a, 506b, etc. for receiving connecting elements 502a, 502b, etc. On an opposite surface to that on which connectors 506a, 506b, etc. are secured is formed a plurality of sensor (e.g., ECG electrodes) pads 508a, 508b, etc. Sensor pads 508a, 508b, etc. are in electrical communication with connecting elements 506a, 506b, etc. such that signals sensed thereby can be communicated to device 500 when 502a, 502b, etc. are engaged with connecting elements 506a, 506b, etc. Embodiments of the monitor device 500 can also include other sensors, for example, sensors for respiration, temperature, movement, EMG, heat flux, galvanic skin response, RFID (radiofrequency identification), location and position. Embodiments of the sensors strap 504 can include contact or non-contact ECG electrodes 508a, 508b, as well as EMG electrodes (507 can illustrate either exemplary ECG or EMG electrodes, or electrodes configured to provide both EMG and ECG signals). Embodiments of the monitor device, including housing and electronics, can be permanently integrated to the strap, clothing, accessory, etc., instead of being removably attached. While the ECG electrodes 508a, 508b are more likely to be located on the anterior chest wall; there can be additional electrodes that allow for multiple lead configurations interchangeably or simultaneously, the ECG leads can also be located on the side or back of the user 507. EMG electrodes, on the other hand, are more likely to be located on the back of the user (located similarly to element 507), particularly when used to monitor musculature important in maintaining healthy posture.

The ECG signal-to-noise ratio can be improved through the use of several algorithms well known to those in the field. R waves 24 occur with depolarization of the heart muscle during early systole 11, and are usually the easiest electrical wave to detect in certain commonly used lead configurations. In this system, R waves 24 can be used as the basis for measuring the cardiac cycle timing.

In order to continue to provide a consistent cadence prompt, averaging algorithms well known to those in the field can be instrumental in enabling smooth and uninterrupted signals for the user, without missed or added individual prompts, despite a noisy ECG signal FIG. 25 (for example, as can be caused by movement of the electrode relative to the skin during physical activity, or by skeletal muscle electromyographic activity). Other commonly used software algorithms can also be helpful in effectively monitoring ECG signals during physical activity. In embodiments of the method and system, standard algorithms can be used to identify certain abnormal or potentially pathological heart rhythms. In some embodiments, the user can be notified of the potential problem, or the abnormal signal may lead to error messages alerting the user to a problem with using device, such as the exemplary notice of "normal heart rhythm not identified," or the like, again potentially recommending further analysis.

An ECG monitor can be used as the only heart monitor in the device, or it can be utilized in combination with other means for monitoring the CV cycle or peripheral blood flow, such as in combination with a PPG monitor. Software analysis can leverage these signals to analyze both cardiac pump function and peripheral vascular pump function. The monitors can further be utilized for specific health monitoring or biofeedback purposes beyond those described here, alone or in conjunction with other monitors. Examples of additional parameters that this system can be configured to monitor include heart rhythm, HR, HR variability, oxygen saturation, physiological activity during sleep, blood pressure, step counts, distance traveled, calories expended, work output, vascular compliance, pulse transit time, respiratory activity, and pulse wave velocity. Examples of additional monitors and sensors that could easily be added to the system include monitors of: temperature, heat flux, sweat, galvanic skin response, respiration, blood pressure, pulse oximetry; Electroencephalography (EEG); EMG, photography & videography, environmental parameters, posture and RFID.

Figure 31:
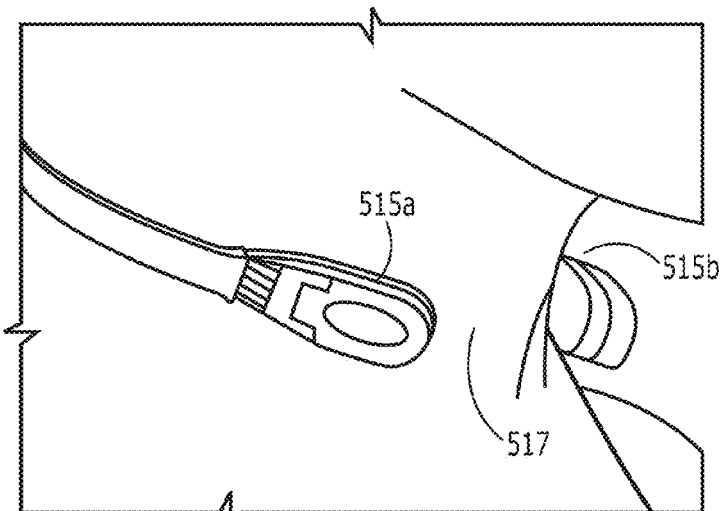
FIG. 31 is an illustration of an exemplary wearable location for the physiological sensors according to an embodiment of the present disclosure.
Figure 32E:
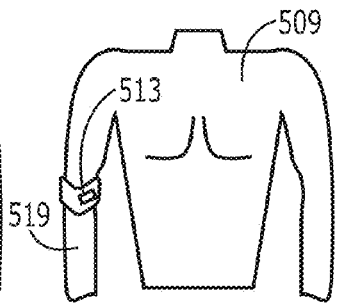
Figure 32F:
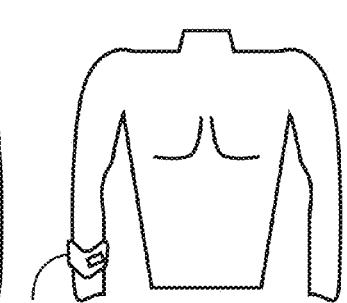
Figure 43A:
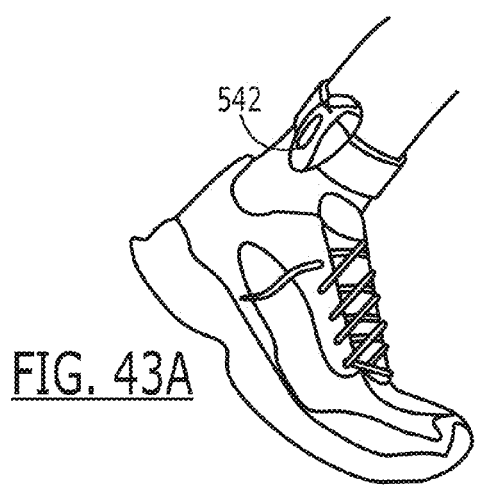
FIG. 43A-C are illustrations of an ankle-based and shoe-based sensor systems according to the present disclosure.
Figure 43B:
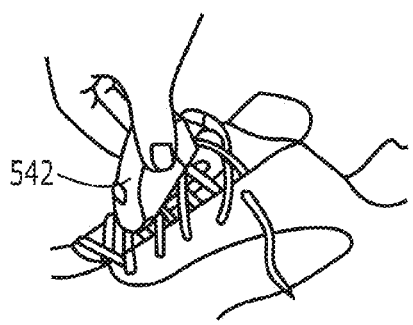
Figure 43C:
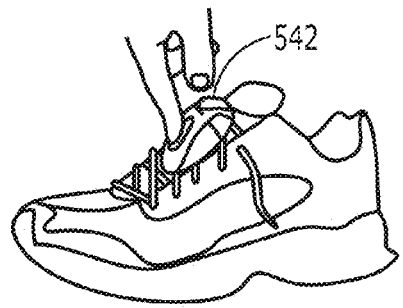

Certain pulse sensing techniques can rely on the device being placed at specific locations, such as on the wrist FIG. 32G, arm FIGS. 32E,F, neck FIG. 31, ankle FIG. 43A, finger(s) FIG. 32H. In certain embodiments of the system, the sensor can be partially or completely located beneath the surface of the skin, for example at a chest wall location similar to that of the skin patch embodiment illustrated in FIG. 30A.

Photoplethysmography is a common method for detecting cardiac pulses. The arterial side of the circulation typically contains more blood during systole than during diastole, with blood vessel diameters increasing and decreasing rhythmically with the changing intravascular pressure inherent in each cardiac cycle. The PPG waveform 40 is due to this cardio-synchronous change in blood volume and pressure with each heartbeat. One or more of many alternative electromagnetic wavelengths, for example alternative wavelengths in the infrared, green, and red spectrum, can be transmitted into the tissue and sensed by a photodetector 524 in order to measure the local changes in blood volume that are described by the pulse wave amplitude. The amount of light transmitted is inversely proportional to the amount of blood—more specifically, hemoglobin—in the tissue. The PPG measures small changes in the absorbance properties of the tissue associated with changes in perfusion in the tissue.

Figures 34A, 34B, 34C, 34D:
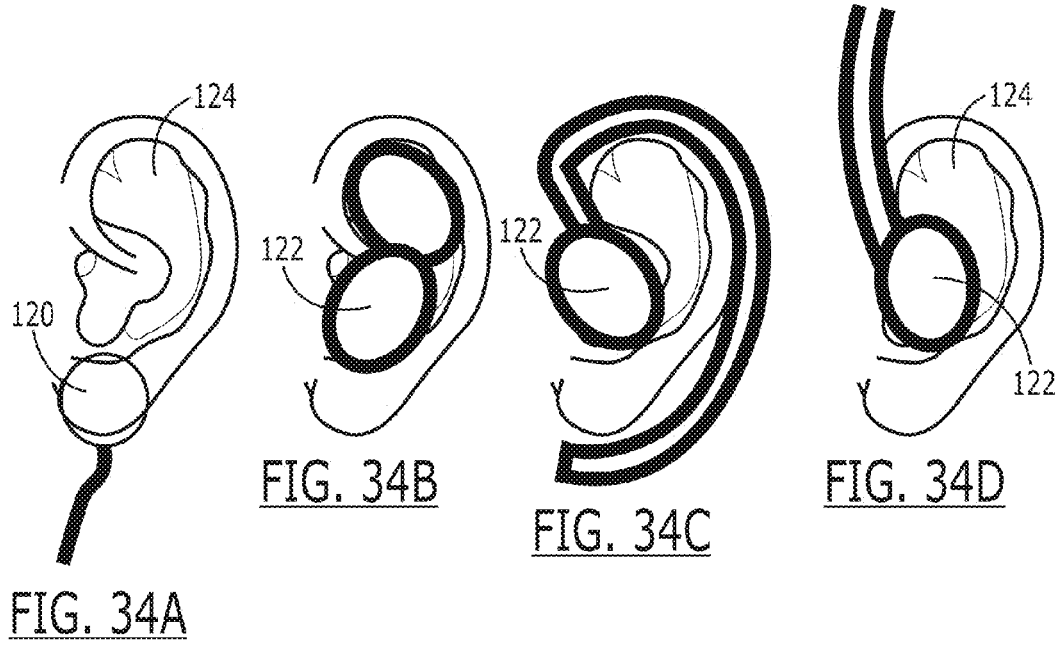
FIGS. 34A-D are illustrations of various embodiments of ear-mounted sensors and, in certain embodiments, feedback devices, according to the present disclosure.

PPG technology is commonly configured to gather data from a fingertip or ear lobe FIG. 34A, as these are well-vascularized structures that are thin enough to allow light waves to be transmitted from a source on one side of the structure to a detector on the other side of the structure. Photoemitters 522 and detectors 524 can also be used to gather data at areas where light does not transmit as easily through structure, such as on the forehead 526, arm 519, chest wall, or temple 528. In some embodiments of the system, at least one PPG sensor is configured to be placed on the skin of the forehead FIG. 33B, wrist FIG. 32G, forearm FIG. 32E, finger FIG. 32H, hand, ear FIG. 34, chest wall, or temple 33A, of the forehead of the user. The forehead sensor 522, 524 can be integrated, for example, into a headband 530, a hat 532, a visor, an audible headset 532, or eyeglasses 538.

Motion artifact presents an important challenge in achieving accurate PPG measurements during exercise or other physical activity when there is movement of the sensors relative to skin, adjacent tissues, and venous blood within the measurement site. Another cause of poor results, particularly at certain skin sites, is the high level of catecholamines in the circulation that may be present during exercise, which can restrict cutaneous blood flow. Nonetheless, studies generally conclude that pulse oximetry, a technology that incorporates multi-wavelength PPG, and PPG by extension, are valid under the conditions of exercise. We have also validated the utility and reliability of PPG in our exercise physiology studies. In some embodiments, a PPG sensor is held against the skin at a pressure sufficient to hold the sensor stationary, compress superficial venous structures, and reduce venous blood content in the skin while not substantially compromising arterial blood flow that is vital to the PPG signal.

FIGS. 31 and 32D illustrate neck-based devices according to the present disclosure. Embodiments of these sensors can be attached to straps, clips, headsets, headphones, necklaces, etc. around the neck 517, or can be attached via adhesive, etc. These devices can include one or more of: sensors (electrodes and processors) for ECG signals; ultrasound (e.g., long axis ultrasound); tissue Doppler (e.g., laser Doppler or Doppler ultrasound); electrical impedance; thermal IR imaging; strain-gauge plethysmography; photoelectric plethysmography; auscultation; pressure sensors (e.g., applanation tonometry); devices that generate and sense reflected PPG signals for measuring pulse or pulse oximetry; movement sensors (e.g. accelerometers, gyroscopes, pressure sensors); capabilities to send and receive wireless and wired signals; audio processors; speakers or audio output devices; and tactile feedback output to the user (e.g., vibratory signal on skin to set cadence for MCP).

In additional embodiments, video cameras that are not in contact with the skin of the user can be used to measure subtle changes in the amount of visible, near-infrared, and/or infrared light of various wavelengths scattered from the user's exposed skin surface throughout the cardiac cycle. These cyclical changes in detected light at various wavelengths can also provide the PPG information on peripheral blood flow required for use of this system. For example, this camera-based approach can be utilized with video games 560, where cameras 564 and camera based game systems 562 can be used to track the user's movement 568.

Several steps can be taken to improve the quality of the PPG signal otherwise distorted by the user's movements during exercise, including the identification, reduction, or elimination of signal artifacts using signal processing algorithms, "adaptive-noise-cancelling" algorithms, and the signals available from accelerometers and other movement sensors. Similar techniques can be used to improve other monitoring capabilities, including CV monitoring via ECG. During movement, as in exercise or walking, the relative motion between the probe or electrode and the skin surface can introduce errors due to excessive motion artifact. To help reduce or eliminate the potential source of signal artifact, the probe or electrode can be securely affixed to the monitoring location by an adhesive (e.g., "band-aid" or temporary tattoo style), a clip FIG. 31 or strap 504, FIG. 32D around the neck 517 chest 509, or an extremity 513, a headband 530, or by some other mechanism. Conductive electrode materials can be used alone or in conjunction with water, electrolyte solutions, conductive gels and conductive pastes, in order to improve conduction across the skin and decrease movement artifact.

In alternative embodiments of the system, visual biofeedback guides the user's MSK activity. The feedback can include information on at least one of the accuracy of the user's MSK activity timing versus the targeted timing and the effectiveness of the activity in generating MCP or in thereby impacting physiological function, such as increasing the diastolic pulse wave 14, or decreasing the systolic pulse wave 10, as shown in the exemplary visual feedback illustrations of FIG. 38. FIG. 38*a* represents the user's effectiveness in generating peripheral blood pressure, volume, or flow during diastole 119*b* relative to that generated during systole 119*a*, over a given time period. Further embodiments of the method and system can provide similar biofeedback-based guidance on accuracy and efficacy of MCP through cues that are auditory, via bone conduction, tactile, stimulated via electricity, or transcranially delivered (e.g., electrical or magnetic stimulation) in order to guide the coordinated synchronization and optimization of peripheral vascular pumping from peripheral MSK activity with the optimal portions of the cardiac pumping cycle.

Monitors of MSK activity can be leveraged to increase the user's ability to optimize MCP. In alternative embodiments of the device, monitoring of the timing of MSK movement, skeletal muscle contraction, and skeletal muscle relaxation, can be achieved via sensors such as accelerometers, gyroscopes, mechanical or solid state pedometers, EMG, proximity, acoustic, optical, or pressure sensors, each enabling increased accuracy of the timing of various types of movement, muscle contraction, or muscle relaxation relative to targeted portions of the cardiac pumping cycle. The timing of the MSK activity and CV cycles can then be compared, enabling appropriate adjustments in timing guidance, possibly including data on progress, efficacy, health implications and coaching. In various embodiments, in addition to the possibility that the MSK sensors can be co-located with the heart sensors in all of the locations described, the MSK activity sensors can alternatively or additionally be integrated into an exercise machine (e.g. FIG. 48), a movement assist device (e.g. FIGS. 45, 46) integrated into a floor covering, or placed within in or adjacent to one or both shoes or socks of the user FIGS. 41, 42, 43A, 43B, 43C, 44.

In addition to guiding the user's MSK activity and thereby enabling MCP, MSK activity sensors provide other potential advantages with this system. Foot strike sensors provide one example FIGS. 41, 42, 43, and 44. Heel strike walking and running occurs when the heel impacts the ground prior to the rest of the foot and is more common when a person takes longer strides or wears shoes with pronounced heels. Beginning each step with a forefoot or midfoot strike can lead to more efficient MSK pumping action than occurs with typical heel strike ambulation, because stepping with the forefoot ensures that forceful contraction of the gastrocnemius (calf) muscle is initiated substantially prior to that of the more proximal thigh musculature (e.g. quadriceps and hamstrings). The reverse order of contraction (thigh before lower leg), more characteristic of heel strike walking or running, can lead to less effective peripheral vascular pumping towards the heart, as it is more likely to trap blood in the distal extremity during ambulation, thereby decreasing the efficiency of MCP and, as a result, also decreasing myocardial perfusion and venous return to the heart. Chronic heel striking during ambulation has also been implicated as a cause of joint trauma and a risk factor for orthopedic injury.

When the system is configured to include an accelerometer sensor that is attached to a user in such a way that it senses MSK movement (acceleration and deceleration), with at least one axis along substantially perpendicular to the ground, then heel striking during walking and running results in a characteristic accelerometer signal 123 that differs in appearance from when the forefoot or midfoot strikes the ground first 120. FIG. 39 shows an embodiment of a visual user interface with exemplary accelerometer tracings of a substantially forefoot or midfoot strike 120 vs. heel strike 123 at ambulation. Note that the heel strike results in an initial rapid deceleration and spike in the tracing 122 prior to the smoother changes in acceleration (more rounded curve) that is representative of the forefoot portion of the ambulatory cycle. Because of the shock absorbing nature of a forefoot or midfoot strike, the initial spike in the accelerometer tracing 121 is substantially diminished due to much less abrupt (and chronically less traumatic) changes in acceleration.

Figure 41:
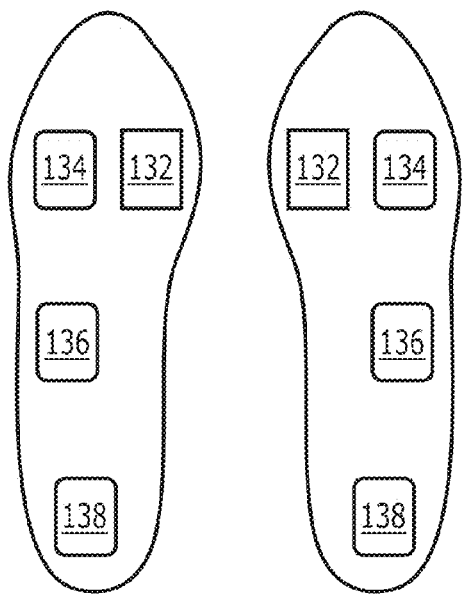
FIGS. 41 and 42 are illustrations of foot-based pressure sensors for placement under the foot of the user, according to the present disclosure.
Figure 42:
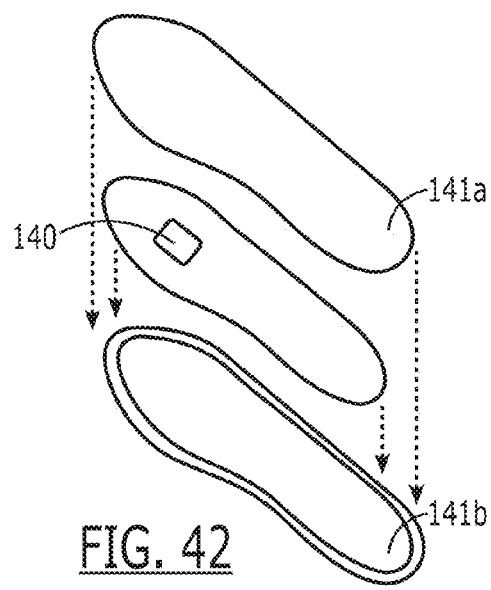

In alternative embodiments of the present disclosure, pressure sensors 132, 134, 136, 138, 140, configured to be located under the foot, as are illustrated in FIGS. 41 and 42, can also be used to obtain foot strike information from a user. In additional embodiments, by using sensors under different portions of the foot, aspects of foot strike timing and force can be monitored for biofeedback. For example, in the exemplary embodiment of FIG. 42, medial forefoot 132, lateral forefoot 134, midfoot, 136, and heel strike sensors 138, as can be housed in a shoe insole 141*a/b*, can be configured in a single system in order to provide biofeedback and coaching on foot ergonomics for improvements in athletic performance, more effective MCP, health, and safety. A heel strike creates transient pressure inside a user's shoe behind the heel of the foot during initial contact with the ground, before the foot rolls fully forward towards the plantar surface of the heel, whereas a mid or forefoot strike typically does not place pressure behind the heel, so a vertically placed pressure sensor behind the heel of the user can also provide valuable information.

Foot based MSK activity sensors can be configured to gather data for analysis, interpretation, and storage with feedback presented to the user in order to teach a user or to assist a healthcare provider or coach in teaching optimization of footwork during athletic activities. In certain embodiments, foot strike sensors can also be used in order to help patients after orthopedic injuries or surgeries. When partial weight bearing is desired, pressure sensors 132, 134, 136, 138, 140 can be configured to quantify the force of the foot strike and provide information to the user when a target range of weight bearing is approached or exceeded.

Monitoring the foot strike in this system can be accomplished with a number of commonly used movement or proximity sensors, including accelerometers; gyroscopes; acoustic, optical, strain sensors; or simple mechanical pressure sensors 546 in order to provide feedback to the user on the timing and quality of the their foot strike.

Figure 40:
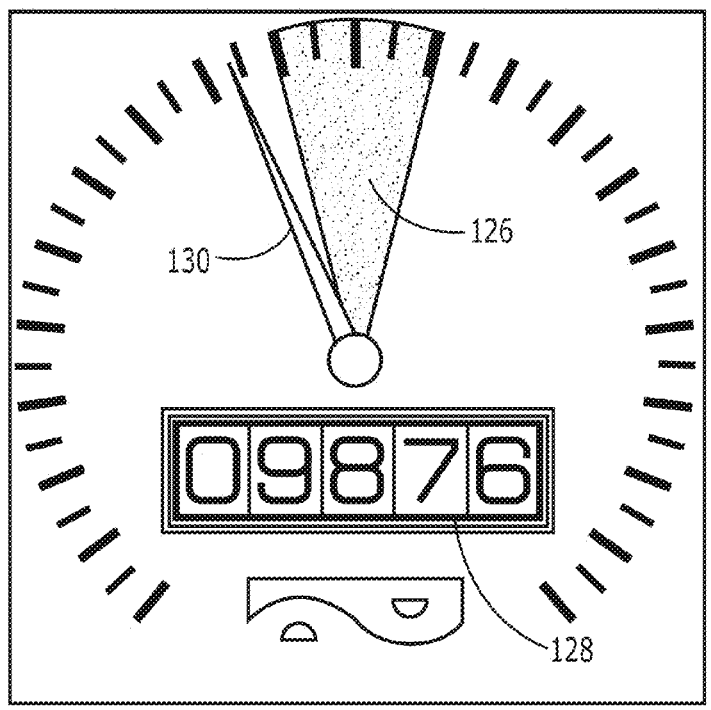
FIG. 40 is an illustration of yet another exemplary visual feedback interface according to the present disclosure.

FIG. 40 is an illustration of exemplary visual biofeedback configured to be provided in a user interface, similar in appearance to an analogue dial in a car, displaying also numerically a multiple of the number of repetitions of the target MSK activity 128. In this example, the number of repetitions of the MSK activity is displayed odometer style 128, shown below the base of the needle 130 on the dial. Alternatively, steps or sets of steps (e.g. sets of 10 or 100 so as to be changing less frequently and therefore less distracting while observing the needle 130 of the dial), taken while walking or running, rpm when biking, distance traveled, or cadence in a variety of other rhythmic physical activities might also be displayed in a similar configuration, either with the dial, as in FIG. 40, or separately.

In this exemplary visual feedback embodiment FIG. 40, the needle 130 can be used, for example, to indicate the observed (sensed) timing of the user's MSK activity relative to the target timing (target=shaded area 126). If the user's MSK activity, for example, is sensed to be consistently occurring close to the target timing (e.g. cardiac phase), the needle would point close to the 12:00 position. If the MSK activity occurs in a consistent timing relationship relative to the cardiac pump timing, and that occurrence is early relative to the target timing, the needle would read to the left of the 12:00 position (as shown), while late would be to the right of 12:00. Shown in the figure is a band 126 spanning approximately the 11:30-12:30 region of the clock-like dial, in this example indicating a region that is acceptably close to the target timing. If the cadence of MSK activity is very close to the HR, but the activity is systematically too late relative to the target timing, the needle, in one exemplary embodiment, would generally reside to the right of the 12:00 or 12:30 position and guide the user to temporarily increase cadence (e.g. MSK activity earlier in the RRI) until the needle moves to the left and into the shaded zone 126. Similarly, in the same embodiment, if the activity occurs consistently too early (needle 130 to the left of the shaded zone, as indeed is illustrated in this example), behavior would be guided towards a brief slowing of the user's MSK cadence until the needle moves into the shaded target zone, at which point the user resumes their steady cadence at the HR. An alternative use of the same illustrated user interface would be to have the needle 130 configured to represent stepping too early displayed as to the right of the shaded target zone (i.e. "too fast"), with a late step ("too slow") displayed as a needle 130 to the left of the target zone 126. In yet another exemplary embodiment of a visual user feedback similar to FIG. 40, the target band can be centered elsewhere on the display dial, such as at the 4 o'clock position for a 33.3% RRI target, with the target zone spanning approximately 4:00-4:30 region.

In a similar embodiment of a visual feedback display FIG. 40, if a user's MSK cadence higher than the target cadence, the needle 130 can move further and further around the dial with each MSK activity, suggesting that the user must slow down to get the needle 130 to stop moving (or visa versa, if the needle 130 is spinning the other way, the user would be directed to speed up). In a similar embodiment, movement of the needle 130 around the dial can indicate the full range of 0% to 100% phase between the detected movements and the cardiac cycle (e.g., the RRI in FIG. 2A). If the target phase were to be, for example, 35% of the RRI, 12:00 would represent this 35% phase value. In an alternative use of a similar visual feedback embodiment, the needle 130 might spin counter-clockwise when the user steps faster than the HR (e.g. each occurrence of the MSK event occurs earlier in the RRI), at a rate that represents the difference between the MSK cadence and the HR. In a similar manner, the needle 130 might spin clockwise when the user is at an MSK cadence that is slower than the HR.

Visual indicators of HR and activity cadence and, in particular, their relative phase can be used in conjunction with, or in lieu of, an audible and/or tactile feedback prompt.

In addition to combination devices described for enabling MCP, foot strike sensors can be used in embodiments of biofeedback methods and systems for guiding behaviors besides foot strike timing. For example, biofeedback on improving foot strike biomechanics can be achieved with a foot strike sensor FIGS. 41, 42, 43, 44.

Figure 44:
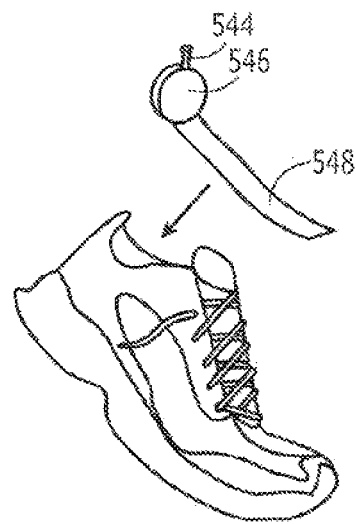
FIG. 44 is an illustration of a foot-based pressure sensor and feedback device, with the sensor vertically located behind the heel of the user, within the shoe, and the attached stabilizing ribbon placed within the shoe, under the foot, either above or below the insole, according to the present disclosure.

A movement monitor with mechanical balloon 546 and squeaker 544 combination, attached to an anchor (e.g., ribbon 548), placed in a shoe substantially vertically behind heel of user, can also serve as a sensor/feedback device, as shown in FIG. 44. Because this pressure sensor, 546 is configured to be placed in a substantially vertical position, behind the heel, it is only triggered when the user's heel strikes the ground prior to the rest of the foot. The pressure sensor, 546, can be attached to an anchoring element (e.g. ribbon, 548 that is configured to be placed under the user's foot, either below or above the sole of the shoe, in order to provide an anchor for the balloon sensor, 546) so that it remains optimally placed despite the forces it is subjected to during ambulation. In one embodiment the sensor is a simple plastic balloon 546 with an air driven noisemaker 544 that creates audible feedback (e.g., squeaks) when the noisemaker is compressed by the back of heel during heel strike walking or running. In this case, the mechanically activated pressure sensing balloon, 546, is located substantially vertically in the user's shoe, behind the calcaneus of the user's foot, so that the sensor is only compressed enough to be activated when the user's heel strikes the ground with the foot still in a somewhat dorsiflexed position, which naturally occurs when the heel strikes prior to the rest of the foot, but not when the heel strike follows a forefoot or midfoot strike. In these exemplary embodiments, during midfoot or forefoot walking or running, the vertically positioned noisemaker 546, 544 is never compressed substantially enough to be triggered. In other words, the user avoids "squeaky shoes" by avoiding heel strike ambulation.

Alternatively or additionally, at least one pressure sensor can be located adjacent to the lateral foot, again in a substantially vertical position, in order to provide feedback on the timing and kinetics of lateral foot strike relative to other parts of the foot. Other simple mechanical sensors can be configured from metal or plastic materials that produce a clicking sound when a certain pressure is applied to them. Electronic or electromechanical sensors, for example piezoelectric sensors, can also be configured to provide pressure feedback in a foot strike detector.

The target timing of a movement or muscle contraction can depend on which muscles in the body are involved and how much acceleration/deceleration occurs with the type of movement and/or exercise. For example, running can be expected to differ from seated bicycling as the upper torso typically moves up and down quite a bit more with the former, resulting in larger inertial effects. The precise targeted timing of when to exert oneself during the cardiac cycle may therefore differ and call for different timing in the feedback prompt. Thus, sensors for measuring and recording MSK activity of other parts of the body (accelerometers, gyroscopes, pressure sensors, strain gauges, EMG sensors, video image processing, etc.) and activity of different aspects of the exercise equipment are contemplated herein.

One or more MSK movement or specific muscle contraction sensors can be simultaneously leveraged in a variety of endurance sports or exercises, such as running, walking, or cycling, when contraction of the distal leg muscles prior to the proximal leg muscles (e.g. gastrocnemius before quadriceps and hamstrings) can also facilitate more efficient MSK blood pumping action, potentially improving cardiac perfusion and filling during diastole, and more effectively enabling MSK perfusion during cardiac systole.

Figure 48C:
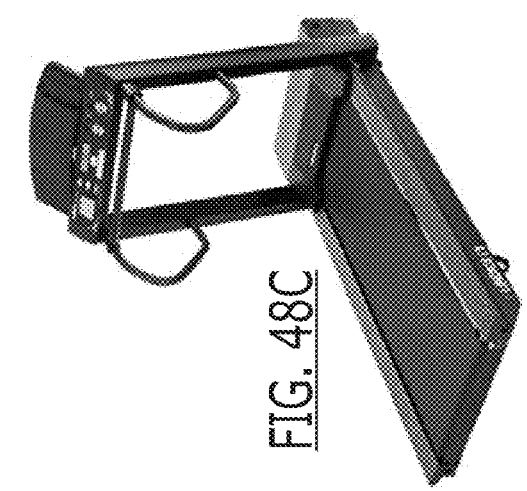
FIG. 48 A-F are illustrations of exemplary exercise devices that may be useful as an exercise element according to an embodiment of the present disclosure.
Figure 48E:
Figure 48B:
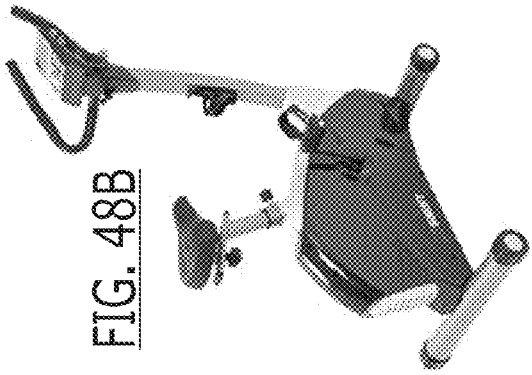
Figure 48A:
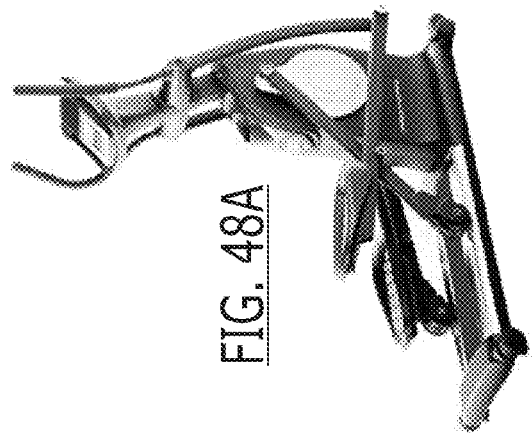
Figure 48D:
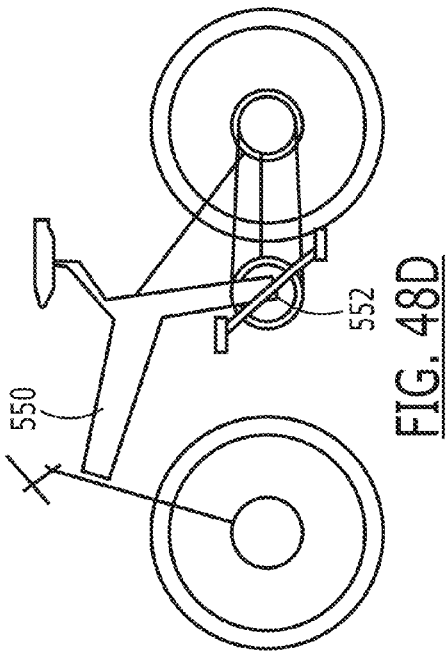
Figure 48F:
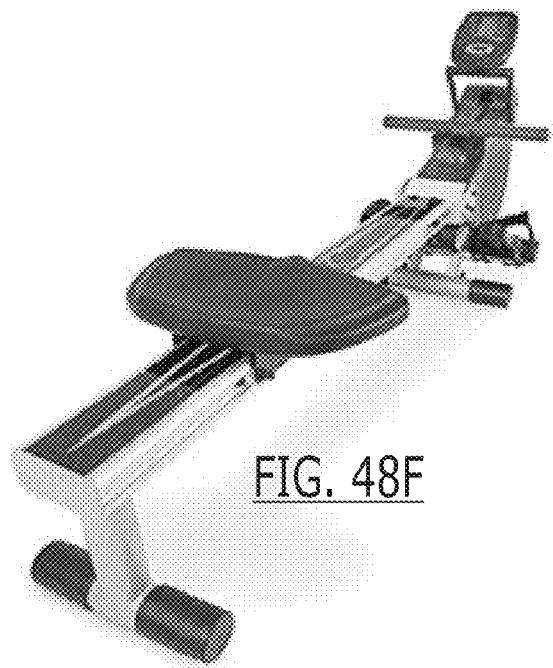

In alternative embodiments, methods and systems of this disclosure can be used to improve the potential benefit and safe use of exercise machines or equipment such as, for example, treadmills FIG. 48C, stationary bicycling equipment FIG. 48B, elliptical trainers FIG. 48A, stair steppers FIG. 48E, rowing machines FIG. 48F, weight lifting, resistance exercise equipment, and push up or pull up exercise equipment. The exercise machines can be designed to track MSK movement (e.g., treadmill foot strike timing, bike pedal cadence and/or torque and timing, elliptical foot, leg, or arm motion). For example, timing of skeletal muscle contraction can be sensed via magnetic or light based switches, via pressure sensors, or via one or more of a myriad of other standard sensors that can be located on or in the machines. Alternatively, pressure or stretch sensors worn in contact with the peripheral skeletal muscle (e.g., using straps around muscle of limbs) can be used to identify the timing of skeletal muscle contraction and MSK movement. Other ways MSK movement might be tracked include: via squeezing of the hands on a pressure sensor; via a mechanically actuated exercise device; via laser or light based movement tracking technologies (e.g., infrared, 2D & 3D video 564, etc. as can be utilized used in video game interfaces); via at least one accelerometer or gyroscope; via pedometer; via monitoring individual or multiple muscle EMG activity; or via actuators otherwise triggered by MSK movement.

Figure 27A:
FIG. 27A is an illustration of a wrist-mounted user interface for providing visual or other forms of feedback for coordinating a user's cardiac pumping cycle and MSK pumping cycle according to an embodiment of the present disclosure.
Figure 27B:
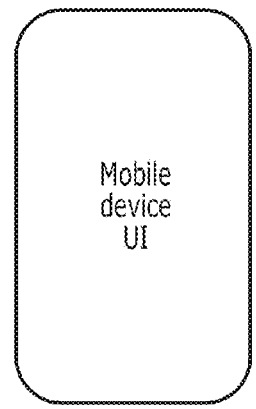
FIG. 27B is an illustration of a mobile device user interface for providing visual or other forms of feedback for coordinating a user's cardiac pumping cycle and MSK pumping cycle according to an embodiment of the present disclosure.
Figure 28A:
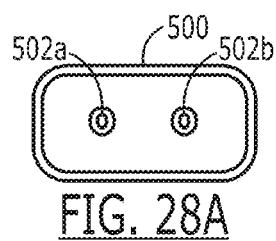
FIGS. 28A-D are illustrations of various views of a removable mounting arrangement for attachment of sensor electronics housing according to an embodiment of the present disclosure.
Figure 28B:
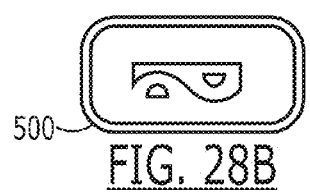
Figure 28C:
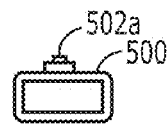
Figure 28D:
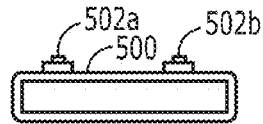

The data derived from the MSK activity sensors can be leveraged to provide visual, auditory or tactile feedback to the user in a wired (e.g. USB connection) or wireless (e.g. Bluetooth or ANT+™) fashion, with software for the user interface residing on proprietary hardware, or on a third party device, e.g. a smartphone FIG. 27B, music player, wrist watch FIG. 27A, tablet computer, exercise equipment display 160, or video game display (alternative 160) etc.

When MSK activity monitors are used in conjunction with cardiac monitors (and potentially respiratory or other physiological monitors), embodiments of the user interface can provide users with information such as the following (by way of example, and without limiting the scope of the present disclosure):

Notification when desired heart and MSK rhythm coordination is achieved.

Suggestions or guidance to optimize the duration of each MSK pump cycle (e.g. shorten or speed up muscle contraction or movement), as efficiency gains from MCP can be increased through optimization of the duration of the skeletal pumping cycle. A MSK pumping cycle duration that is coordinated with the duration of the CV pumping cycle has been supported by multiple medical studies to be preferred.

Directions to optimize the specific skeletal muscles involved in the MSK activity.

Directions on the sequence of specific skeletal muscle group utilization.

Directions to optimize the timing of skeletal muscle relaxation.

Directions on characteristics of MSK activity (e.g., force, magnitude, or speed).

Feedback on progress versus goals over time.

Feedback on physiological trends, for example ECG changes that seem to recur predictably related to specific coordinated movement timing (e.g. ECG changes that suggest changes in the adequacy of myocardial perfusion).

In embodiments of this system and method, physiological efficiency can be measured via increases or decreases in CV and respiratory effort required at a measured amount of MSK work output. Alternatively, efficiency can be deduced by measuring changes in MSK work output (wattage) at a measured consistent physiological effort (e.g., HR, respiratory effort, VO2). For example, approximations of work output for the purpose of finding a user's target movement or skeletal muscle contraction timing can be calculated from the incline and speed of a treadmill FIG. 48C, FIG. 49 the resistance and speed (at a given stride distance) on an elliptical FIG. 48A, the torque and RPM on the crank or hub of a bicycle 552, 48B, D, or via similar measurements in a rowing machine 48F.

When used in conjunction with certain exercise machines (e.g. 566, FIG. 48), or integrated within the exercise machines, certain embodiments of the system and method can be configured to automate changes in resistance, speed, or other work parameters to assist in achieving MCP at target heart rates and target cadences. In the case of a stationary 48B or non-stationary bicycle 550, for example, the gearing 552 could be automatically adjusted (using, for example, the Shimano Di2 electrically activated shifting system) so that the target cadence is maintained to at a matching HR, target HR is maintained at a matching cadence, or a combination of target HR ranges and target cadence ranges are maintained. In order to help identify optimal timing of a user's MSK activity, the phase or timing of the feedback prompt can be varied for a period of time, relative to the target timing location in the CC. "Optimum" timing or phasing of MSK activity relative to the cardiac pump cycle (optimal target timing location in the CC) would correspond to the relative timing that resulted in the greatest equivalent wattage (i.e., torque×RPM) at a given HR. Alternatively, to normalize for a variations in HR and corresponding cadence, the highest level work output achieved, as calculated from the ratio of (work output)/(heart beat), could be used for determining the target timing location in the CC. Once determined, the feedback prompt would be set to occur at a constant proper target timing location relative to the cardiac cycle and the bicycle's gearing 552 adjusted automatically to help maintain the rider's proper HR-matching cadence—a particularly useful configuration for accommodating terrain changes that would otherwise affect the rider's cadence and/or HR and make it more difficult to maintain targeted MSK activity timing relative to the target timing location in the cardiac cycle. In further embodiments, a bicycle 550, 566, FIG. 48B with an integrated motor that provides electric pedal assistance to a user 568 can be configured to provide the timing of the pedal assistance to correspond with the aHR, or in some embodiments, to correspond with the target timing location in the CC, thereby enabling MCP.

In certain embodiments of methods and systems in this disclosure, wherein the system is integrated with an exercise machine FIGS. 48A-F, 49, the timing and quality of MSK movement on the exercise machine can be both mechanically guided and assisted to help coordinate MSK movement with the cardiac pump cycle. The power, speed, duration, direction, and magnitude of assisted movement can be variables that are controlled in order to facilitate the obtainment and maintenance of MCP, as needed, since coordination, speed, strength, endurance, and ability to sense the desired pump timing and frequency can vary from user to user, and can change with time, fitness level, experience, training, or fatigue. For example, with certain exercise machines such as an elliptical FIG. 48A, rowing machine FIG. 48F, stepping machine FIG. 48E, or stationary bicycle FIG. 48B, the machine's resistance can be increased or decreased dynamically if the user's cadence (or phase) is too fast (early) or slow (late), respectively.

In separate embodiments of methods and systems in this disclosure, peripheral vascular pumping can be augmented by applying mechanical pressure to the body of the user. For example, a positive pressure treadmill device, wherein the user's weight is partially supported by externally applied positive pressure, can be configured to automatically and rapidly pulse the positive pressure in order to generate external counterpulsation at a target timing location in the CC (for example, using a commercially available AlterG, "antigravity" treadmill, or a similar system, that has been configured to enable MCP+/−ECP). In additional embodiments, a positive pressure balloon device, configured to pulse pressure at a target timing location in the CC, wrapped around the user in a manner similar to those used in commercially available External Counterpulsation (ECP) machines, or even ECP machines themselves, can configured to be used in conjunction with these exercise systems.

The target timing location within the CC for a user to coordinate their MSK activity and enable MCP can vary from person-to-person or over time (e.g. by individual, activity, cardiac rhythm, age, fitness). Furthermore, optimal MSK activity timing relative to the RRI target timing can change with HR. The systolic period (11 in FIG. 1A) increases as a percentage of the RR interval as the HR increases and, accordingly, the optimal timing of MSK activity can similarly change with HR. In one example, the optimal target timing location in the CC for MSK activity in an individual user at a HR of 110, 140, and 170 and can be substantially at 30%, 35% and 40% of the RRI (FIG. 2B).

The timing of the prompt relative to an RRI (FIG. 2A) can be varied via an algorithm that is driven by relationship between HR and the relative timing of components of the heart cycle. In certain embodiments, a feedback prompt identifies targeted timing of the user's maximal MSK movement, inertial changes, or skeletal muscle contraction or relaxation, at a timing location in the RRI that has been calculated to approximate the end of the T-Wave 30, which typically closely coincides with aortic valve closure (12 in FIG. 1) and early diastole. In one alternative embodiment, an algorithm is used that estimates end T-Wave using a value calculated from the QT or RT interval, which typically increases as a percentage of the RRI in a non-linear fashion with increasing HR (there are multiple well-known published approaches to calculating this interval for diagnostic purposes in the medical ECG literature). In a second alternative embodiment, the prompt enables the user to time MSK pumping to occur at a specific percent of the RRI at lower heart rates, but proportionally later in the RRI as the HR increases, according to a simpler, linear algorithm. For example, the initial prompt can guide maximal MSK pumping to occur at substantially 32% of the RRI when the pulse is low (e.g. below 100 bpm), with the algorithm designed to initiate the prompt at a higher percent of the RRI as the pulse gradually increases with exercise, in one example increasing to a prompt as high as 43% of the RRI. With these algorithms, even at very high pulse rates, the prompt will not be initiated substantially later than half way through the RRI, because end T-Wave is not likely to occur that late even during intense exercise. As HR increases, aortic valve closure occurs at a proportionally later time in the RRI. In other embodiments, the user can be guided to initiate MSK activity at a fixed time after each R wave 24, wherein the fixed time interval can be HR dependent. For example, the time delay after the R wave 24 may vary with the HR so as to synchronize the arrival of the MSK activity generated pressure wave at the heart with the proper diastolic point in the cardiac cycle that results in increased myocardial perfusion.

In some embodiments of methods and systems in this disclosure, the user times their foot strikes or other readily recognizable actions (e.g. pedal push with bicycling) to occur synchronous with the feedback prompt e.g. 54, 35, 60. The system then adjusts the prompt timing so as to more optimally align their sensed movements to the target timing location in the CC. Favorable MSK movement or muscle contraction timing relative to the cardiac cycle may vary between different exercises.

In addition to telling the user when to perform the desired MSK activity, the system can also provide visual, auditory or tactile feedback to help the user achieve the desired cardiosynchronous rate of other periodic physiological functions. For example, respiratory rate and activity timing can be coordinated with targeted timing locations in both the CC and the MSK activity cycles.

Audible prompts indicating when to perform a desired physical MSK activity or other function can be provided to the user in the form of regularly occurring audible tones, specifically timed to substantially coincide with a target point in the cardiac cycle. This can be provided in a variety of ways, including audible beats, clicks, beeps, heart sounds, musical notes, drum beats, pulsed tones, or via music with a beat frequency and timing coordinated to occur substantially concurrent with a target timing location within the CC.

In other alternative embodiments of methods and systems of this disclosure, audible prompts can be comprised of music with a rhythm or beat configured to guide a user's MSK activity timing. The system can be programmed to select music from designated music libraries with beats or rhythms of frequencies that match or approximate the current or future target cadences and target HRs. In certain embodiments, the device can further be configured to constantly adjust the playback speed of the particular song in order to consistently locate the beat (MSK activity prompt) at the target timing location in the CC. Additionally, the music with altered playback speed can be pitch-corrected to maintain the proper intonation. In yet other embodiments, the music's beat can be used to guide the user to a specific cadence (e.g., steps per minute) that matches the timing of MSK activity to a target location in each heart pumping cycle. In certain embodiments, a second indicator can help the user to hone in on the optimal MSK activity timing at that cadence. In further embodiments, the beat timing (e.g. drum beat, base, etc.) is separate from the music. In yet further embodiments, the MSK sensors are configured to provide data to drive the musical beat or other aspects of the music.

The duration of each audible, tactile, or visual prompt can alternatively extend over a specific length of time in order to enable the user to self-modulate MSK activity to the timing that is perceived as optimal, for example, the specific MSK activity timing that is perceived as most comfortable or most sustainable, within the duration of the prompt. For example, in an extreme case the tone can begin at 25% of the R-R interval, and persist until 50% of the way through the R-R interval. Shorter durations of prompt can still serve this purpose. The duration of the prompt signal can be programmed to vary with HR, or to remain constant, regardless of HR. In one example, the prompt can begin substantially 30 ms prior to the target timing location in the CC, and end substantially 30 ms after the target timing. In an alternative exemplary embodiment, the prompt can be programmed to occur earlier in the RRI (for example, 25-35% of the RRI) at lower HR's (e.g., below 80 bpm), increasing slightly (e.g. by 0.1%) each time the HR increases by an identified increment (e.g., by one beat per minute).

Alternative embodiments of the user interface can provide tactile prompts to the user through regular rhythmic tactile sensations (e.g., tapping, electrical stimulation, or vibration on the skin of the user). In certain embodiments, the tactile feedback is produced with substantially consistent timing relative to a phase or portion of the RRI of the ECG FIG. 2B. In an exemplary embodiment, the tactile sensation is provided at approximately 30% of the RRI. In a second alternative embodiment, the tactile sensation is created approximately 35% of the RRI. In a third embodiment, the tactile sensation is created approximately 40% of the RRI. In a fourth example, the tactile sensation occurs at a % of the RRI that varies with the HR of the user. In a fifth alternative embodiment, the tactile sensation is created at an estimate of the timing of aortic valve closure.

In certain alternative embodiments, visual feedback is provided. The visual feedback can prompt the user to perform MSK activity at a target timing that facilitates MCP. The feedback can also guide the individual to slow down, speed up, or move earlier or later, in order to accurately match the target timing location in the heart's pump cycle. Visual feedback, in some embodiments, can also provide guidance to the user on when and how to modify work output or other parameters, including, for example, resistance, incline, stride length, or other movement parameters on an exercise machine, e.g., FIGS. 48A-F, FIG. 49. In certain embodiments, the user will be given feedback as to the quality and/or magnitude of the counter-pulsation wave that is achieved. Visual feedback can be provided in the form of graphics e.g. FIGS. 38A,B. Visual feedback can be presented in various configurations, including at least one of numerals, charts, lights, colors, dials, tables, graphs, graphics, animations, and in a game format. In an example embodiment of a game format, the object of the game or challenge to the user can be to have the user try to optimize the measured physiological efficiency. For example, the user can progress in a game if they are able to minimize their HR by slightly modifying the timing of their rhythmic MSK activity relative to the cardiac cycle timing, while maintaining a constant work output and cadence equal to the HR. In another example, the user can progress in the game by increasing work output relative to any given HR, by modifying MSK activity parameters at a constant work output. In yet another example, the accuracy of movement timing relative to target timing can be measured as a means for assessing progress in the game.

Some activities are preferentially performed at a cadence that is substantially different than the user's target HR (or natural HR during the activity), therefore, in any of the described embodiments in this disclosure, the tactile, auditory, or visual feedback can be preferably provided in synch with a unitary fraction of the heartbeats, substantially at a specific timing location in the CC. Alternatively, the feedback can, for example, occur with every second, third, fourth or fifth heartbeat (e.g., 1:1, 1:2, 1:3, 1:4, 1:5 ratio of maximal MSK vascular pumping prompt to cardiac pump cycles). Such approaches can provide an alternative for people that walk or otherwise exercise more slowly and prefer to provide MCP at a slower rate than that which would be required with a MSK cadence matched exactly to the user's HR. This may be particularly helpful in the elderly population, or with individuals with heart disease or otherwise limited exercise capacity. This mode can is also useful during certain strenuous or low cadence rhythmic activities, such as hiking, rowing, swimming, skating, resistance exercises, etc., when MSK cadence is often naturally substantially lower than HR during that activity. For example, when hiking up an incline, higher heart rates and lower cadences can lead to optimization of MCP at a 1:2 ratio of steps to heartbeats (or MSK cadence: aHR). On the other hand, an MSK cadence to HR ratio of 1:1 is more commonly utilized during activities such as running or biking. In certain embodiments, the user can be able to switch between prompt:HR ratios (e.g. from 1:1 to 1:2 and vice versa) via the user interface. In alternative embodiments, the device algorithm can be programmed to automatically convert to an alternative prompt ratio, for example when 1:2 prompt timing is identified algorithmically as more appropriate or desirable given at least one of the sensed MSK movement, MSK activity, MSK activity cadence, user input to system settings, and heart rhythm. In certain embodiments, the prompt ratio of the device can be able to be both automatically and manually converted.

Alternatively, it can also be beneficial to move at fractions such as ⅔ (i.e., move through 2 cycles of the repetitive motion for every 3 heart beats), ¾, ⅖, ⅗, etc., of the HR. In these examples, some of the movements can coincide with an undesirable, or less-than-optimal, timing relative to the cardiac the cycle. However, with some of the movements aligned with highly desirable timing regions relative to the cardiac cycle, and some with a minor or neutral enhancement, a net gain in physiological efficiency, perfusion, and oxygen delivery can still be achieved, particularly since the physical activity rhythm may "skip beats". In a "skipped beat" embodiment of the method and system, a user can be prompted at or to a cadence that intermittently coincides with targeted timing locations in the CC. For example, a user could be prompted at a 3:5 ratio of 1:1 for "cadence of activity":"CC", but a cadence of "MSK activity":"CC" and a 2:5 ratio of "rest phase":"CC" (where P=push/exhale and R=rest/inhale, each occurring substantially at the same targeted timing location in the CC), the pattern would be: of P-P-P-R-R-P-P-P-R-R-P-P-P-R-R, etc... Additional characteristics of the individual user's physiology or physical activities can materially impact the flow propagation delays inherent in the arterial vasculature. Accordingly, to enable further optimization of the correlation of the physical activity prompt timing to the onset of cardiac diastole, at least one of the following exemplary personal variables can be provided as data input to the timing algorithms—the user's age; height; HRmax; weight; BMI; baseline blood pressures; fitness; medications; health; strength; pulse transit time; cardiac output; type of exercise; biomechanics; health or fitness or activity goals; or the type of preferred foot strike.

Alternative embodiments of this system can be helpful to many different types of users. For example, MCP and measurements thereof can be helpful during athletic competition; during training for athletic competition; during aerobic exercise; during resistance exercise; during walking, running, biking, skating, swimming, or rowing; during cardiac rehabilitation; during marching; during physical therapy; diagnostic cardiac ECG monitoring; and during cardiac exercise stress testing.

Figure 49:
FIG. 49 is an illustration of ECG stress test equipment that may be advantageously used according to an embodiment of the present disclosure.

Embodiments of the method and systems of this disclosure enable substantial improvements in cardiac exercise stress testing, for example, treadmill FIG. 49 or bicycle FIG. 48B embodiments of an exercise stress test system can be configured to monitor MSK activity timing along with CC timing for inadvertent coordination of MSK activity and cardiac pump timing, with algorithms screening for correlations between attributes of the coordinated timing and indications of cardiac ischemia (e.g. ECG changes such as ST depression), changes in HR variability, changes in blood pressure, occurrences of cardiac dysrhythmia, or changes in ventricular wall motion when an echocardiogram is utilized in conjunction with the stress test.

In addition, while the value of aligning the timing and quality of one's MSK activity to enhance myocardial or peripheral muscle perfusion (and the resulting gains in efficiency) has been discussed, under some conditions, the opposite can be desirable. For example, during a cardiac stress test, it can be desirable to increase the stress to the heart for a limited period of time to evaluate the resulting ECG, or to alternate between periods of more and less stressed conditions, while otherwise maintaining a work output level during exercise. The health care practitioner can thus use the same system in order to guide the user to increase CV stress by generating maximal MSK pump pressure during peak systole, thereby decreasing myocardial perfusion while simultaneously increasing cardiac work. Exercise stress testing would provide a means for identifying any relationship that can exist between myocardial ischemic incidents and the timing of MSK movement relative to the cardiac pumping cycle. While this type of inverse counter-pulsation (iMCP, "resonant pressures", or "stress resonance", which is maximal MSK pumping during cardiac systole, which correlates with increased CV stress and decreased myocardial perfusion) is considered undesirable during normal exercise in an uncontrolled setting, it can be helpful to test patients for cardiac risk, particularly since these unfavorably physiological conditions can occur incidentally during exercise. In a controlled healthcare environment, iMCP may also be helpful, if provided in carefully predetermined amounts, towards "preconditioning" the myocardium against future ischemic or stressful events.

In yet another embodiment of the present disclosure, the target relationship between the user's rhythmic MSK activity and their cardiac cycle can be made to alternate for periods of time between unfavorable (e.g., iMCP) and favorable (e.g., MCP) phasing. This can create alternating periods of poor and enhanced blood perfusion and oxygen delivery to the muscles (i.e., periods of ischemic stress followed by enhanced reperfusion). Such intermittent periods of ischemia followed by reperfusion have been shown to provide a protective effect with less tissue damage resulting from subsequent prolonged ischemia ("ischemic preconditioning") as well as recent previous episodes of prolonged ischemia ("ischemic post-conditioning"). The time periods can last for several seconds, several minutes or longer, and the two states can last for equal or unequal times. For example, iMCP can be induced for five minutes, followed by 10 minutes of MCP, with the cycle repeated four times. In another example, the cycle is repeated only two times. This MCP-iMCP preconditioning process can be beneficial to long distance runners, for example, in helping protect the heart muscle from tissue damage.

ECG monitoring during movement can also lead to a particular type of motion artifact in the ECG signal due to rhythmic variations in movement of the skin and underlying soft tissue relative to the location of the heart that is being monitored. MSK movement timing that consistently lines up with important portions of the heart's ECG signal can lead to problematic misleading ECG tracings during cardiac ECG stress testing, typically performed with a system like the one illustrated in FIG. 49. Importantly, this type of movement artifact can potentially cause ST segment ECG changes that can be easily mistaken for myocardial ischemia. Therefore, embodiments of the system and method of this disclosure can be used to quantify and eliminate these movement artifacts by adding movement monitors (e.g. accelerometers or pressure sensors) to the stress ECG testing embodiment of the method and device FIG. 49 in order to monitor the timing of the user's movement relative to their ECG timing, and screen for correlations between consistent MSK activity to CC phase relationships and ECG changes potentially suggestive of ischemia. Computer algorithms in these method and system embodiments can be configured to at least one of identify, quantify and eliminate identified movement related motion artifacts generated in this manner. Moving in a consistent way with a certain cardiac phase can be identified by comparing the ECG waveforms created when MSK movement occurs at different locations in the RRI, thereby importantly decreasing the incidence of false positive exercise stress tests. During use of certain embodiments of the system, these types of movement artifacts can also be avoided by alerting the user or the person administering the stress test that the user is stepping with a specific movement timing, relative to the heart cycle timing, that increases the likelihood of problematic movement artifact, enabling the user to therefore be guided to alter cadence timing in order to improve the accuracy of the test. (e.g. a audio, visual (e.g. red light) or tactile notification to change cadence that remains until the cadence has been adequately altered. In preferred embodiments, the system could prompt the user to move at a specific cadence.) Unfavorable cadence timing that increases the likelihood of movement artifact, in an exercise stress test, can be as simple as stepping or pedaling at the same cadence as one's HR. A simple alert or indication on the report could decrease the incidence of false positives due to this artifact. Alternatively, the user could be prompted to move with a specific timing, relative to the heart cycle, in order to facilitate identification of movement artifact. Because timing of movement relative to the heart cycle has the ability to potentially enhance or diminish CV work and perfusion, it is particularly important that movement artifact induced changes that can mimic cardiac ischemia are differentiated from true ischemia. During studies conducted in our labs, this type of movement artifact can be more pronounced when ECG leads are placed over larger volumes of soft tissue on the chest wall, possibly at least partially leading to the higher reported incidence of false positive exercise stress tests results noted in medical literature to be more common in women than in men.

Another exemplary health care application of methods and systems of this disclosure is enabled through adding movement-timing capabilities to ambulatory cardiac monitors. With appropriate analytics, cardiac events such as episodes of ischemia or arrhythmia, can be correlated to MCP and iMCP. Additionally, the ambulatory ECG system could be configured to prompt the user's movement and cadence to optimize MCP. Additionally, use of devices that enable the user to utilize MCP during exercise, and to avoid IMCP or stress resonance during exercise, can be useful in order to increase the safety and utility of a cardiac rehabilitation program or any activity program for users that are at risk of CV injury.

According to certain embodiments of the method and system, analyzed data from individual sensors is presented to the user through a user interface, to enable tracking of progress. This data can also be transmitted, in a wired or wireless fashion, for at least one of storage, retrieval, manipulation and communication, on at least one of: a device within the system; an ancillary device (e.g., smart phone, music player, watch, server, or personal computer); a removable storage device; a network; and the World Wide Web (ie. in the "cloud"). The data can be leveraged within the system for: tracking progress, data analysis, comparison to other users, comparison to historical personal user data, comparison to data from demographic groups (e.g. age matched, fitness matched, gender matched data, etc.), teaching, and coaching individuals alone or in groups. The data can be analysed alone or in combination with other fitness, exercise, athletic or health related data for the user. The user may also wish to share the data or user feedback produced by the device, including one or more of the following exemplary types of personal, group or demographic data tracked in an ongoing or historical fashion in embodiments of the disclosure:

Duration of MCP (e.g., minutes, steps, miles, rpm, etc. over a given timeframe)

Duration or percentage of rhythmic physical activity at target MSK timing

Area under the MCP pressure curve or diastolic: Systolic wave ratios

Speed or cadence during MCP

HR tracking—time spent at different heart rates or in different HR zones

ECG analysis and tracings—baseline and correlated to MSK event timing: CC timing Foot strike tracking (e.g., heel vs. midfoot/forefoot striking)

Cadence, speed, or distance tracking, and elevations reached

Distance traveled during MCP (e.g., pedometer, cadence sensor, accelerometer and/or GPS)

Locations visited (GPS) during MCP

Body/limb position during MCP

MSK anatomy or activities involved during MCP

Exercise machine settings

Work output

Embodiments of the methods and systems of this disclosure can enable measurements of physiological efficiency and work output that have not previously been recognized or well understood. For example, watts/beat (work output relative to each heart beat) or speed/beat (e.g. running), can provide a means to illustrate to a user their physiological efficiency during different activities, e.g. when varying MSK activity timing:CC timing. This new measurement could provide both insight into the improvements in efficiency from MCP, as well as a more reliable way of measuring fitness over time, because MCP would become a constant, rather than an unknown variable, during measurement of work output. For example, when used in conjunction with watt measuring devices well known to the fitness and biking industries, watts/beat may be an exciting new metric to users of embodiments of this method and device.

It will also be appreciated that several games (e.g. smart device digital games, video games, online games) and other interactive programs can use any of the measurements described in this disclosure for providing insight into the accuracy or efficiency of prompted MSK activity timing during exercise as drivers for progress in a game, for proving achievement related information or rewards, for gaining status in a game or competition, or for other related uses in the program. The data collection, analysis, and feedback disclosed herein can be applied to games or programs specifically designed to utilize such data and provide relevant feedback contemplated herein, as well as to games not so designed but capable of utilizing the data and providing feedback through modifications or extensions of those games or programs.

In certain embodiments of the systems of this disclosure, software facilitates the analysis, review, display, printing, sharing, etc. of a user's data on progress with MCP, MSK activity, CV and related data via: email; proprietary web based applications; social networking web sites (e.g., Facebook, Twitter, Google+, etc.); Healthcare Web Portals (e.g., personal or shared); and so on. The information can be shared, for example, with family members, work groups, friends, social networks, exercise related communities, interest groups, health and fitness oriented communities, sports related communities, coaches, educational institutions, healthcare providers, insurers or employers. The information provided by this system and method can also be integrated with data and information provided from other healthcare sources, other devices, or users, in order to consolidate, cross reference, or otherwise increase the utility of the information.

In certain embodiments, systems for biofeedback that enable MCP can be configured to work with commonly used CV sensing systems for fitness monitoring that are on the market today. For example, commercial CV fitness monitors marketed by Suunto, Polar, Nike, Timex, Adidas, Zephyr, Alive Technologies, Shimmer, Dayton Industrial, Garmin, Wahoo, Electronic Arts, ePulse, AliveCor, and others, can be used to meet some of the hardware requirements of the system, including, but not limited to, the wireless ECG sensors, accelerometers, pressure sensors, or EMG systems, for example. In some embodiments of the biofeedback system, additional sensors, for example movement sensors, watt meters, or respiratory sensors, can be provided that are integrated within, or that work in conjunction with the commercial CV fitness monitoring device. In other embodiments of the system, software can be provided in one or more applications on a mobile hardware device, configured to provide a user interface that is used in combination with one or more of these off-the-shelf hardware monitoring devices. For example, a commercial CV sensor can provide an analogue or digital signal or time stamp (event marker or timing signal) that provides information on the absolute or relative timing of each R wave 24. This signal, and information correlated to the R wave timing subsequent to computation of the proper feedback prompt, e.g. 54, 35, 60, can be utilized, to provide appropriate user feedback. In alternative embodiments, a commercial fitness monitor with both CV and movement sensing capabilities can be configured to provide data on the ongoing relationship between elements of the CV cycle timing and MSK movement timing. In this case, analysis of HR can enable the prompt timing to be initiated at the HR, or at a fraction of the HR (e.g., cadence:HR=1:1, 1:2, etc.) at an arbitrary MSK activity timing to cardiac cycle location timing relationship, with algorithms within the system configured to subsequently adjust the timing of the prompt until the MSK movement timing regularly matches the target CC timing.

In addition, a variety of sensor apparatus, with and without feedback to a user, are contemplated in this disclosure. Referring to FIGS. 32E, F, G and H, and 43A, there is shown therein a plurality of arm-, hand-, or ankle-worn pulse wave sensors that can be located over one or more arteries or arterioles of the upper or lower extremity (e.g., they can be configured for the wrist, arm, finger, leg, toe), head (e.g., above temporal artery 528 or forehead 526), neck 517, or on other skin surfaces of the body, which can alternatively also provide tactile pacing guidance (e.g., a tactile metronome with timing adaptive to CC timing), and in certain embodiments, can further provide auditory pacing direction (e.g., auditory metronome with adaptive timing), and in more embodiments, can provide auditory feedback directly or wirelessly to a headset, which can itself be configured to provide visual 536 or tactile feedback.

According to still further embodiments of the present disclosure, other forms of headsets, such as sport glasses 538, safety equipment, earphones 122, and so forth can include pulse wave sensors (e.g., PPG 522/524, Applanation Tonometry, ear 124, substantially adjacent to the superficial temporal artery 528, etc.); tactile feedback; and auditory feedback directly through the headset 122. In some embodiments of the disclosure, the undersurface of the brim of a hat 532 or visor could be further configured to provide visual feedback. Examples of such embodiments that include PPG sensors with photoemitters 522 and photodetectors 524 are shown in the following illustrations: FIG. 33A, headband 530; FIG. 33B, headband 530 with audio feedback 533; FIG. 33C, hat embodiment 532; FIG. 33D, eyeglasses with wireless headset 534; FIG. 33E, eyeglasses 538 and heads-up visual display 536; and, FIG. 33F, eyeglasses 538 with audio headset 535. In further embodiments, the hat or other head-worn device could be configured to include an EEG or cerebral perfusion monitor (e.g. to monitor relaxation, mindfulness, or alpha wave activity).

Referring next to FIGS. 34A-34D, there is shown therein a plurality of ear attached sensors that can include: wired or wireless transmission and receiving capabilities for all sensor inputs, music, and other sound or tactile signals and prompts for the user; pulse wave sensing via PPG (note that PPG sensing can occur at several locations in preferred embodiments, including the ear lobe 120, the external auditory canal 122, the outer ear 124, the temple 528 (in the proximity of the superficial temporal artery and branches thereof), the neck 517, or the forehead 526); pulse wave sensing via applanation tonometry (for HR; timing of the heart cycle; and/or for quantification of the counter-pulsation wave), via auscultation, or via ultrasound; and accelerometers or other movement sensors for sensing of MSK cadence (the timing of counter-pulsation) according to an embodiment of the present disclosure.

In ear-based embodiments of the present disclosure, at least one of the CV cycle and the MSK movement cycle can be monitored from a sensor(s) placed: on or into at least one of the external opening of the external ear canal 122; clipped to the outer ear 124; clipped to the ear lobe 120, held to the outer ear by a headband 530, a hat 532, or a headset 534; or wrapped around the outer ear FIG. 34C. In addition, they can be configured to monitor pulsatile blood flow of the CV cycle by utilizing one or more of: light emitters 522 and sensors 524 (e.g., via PPG); pressure sensors (e.g., via applanation tonometry); ultrasound, auscultation, or other CV sensors well known to those practicing the art of CV monitoring.

In certain embodiments, MSK movement can also be monitored within this ear-based device via at least one of an integrated or separate accelerometer(s); gyroscope(s); or mechanical movement sensor (e.g., pendulum based pedometer). Ear-based sensor(s) embodiments can also be housed with all of the instruments required to quantify the sensed signals and compute an appropriate MSK activity prompt for the user. These instruments can include a microprocessor, memory and power, as well as the software required to analyze and calculate the appropriate biofeedback, and a wired or wireless transmitter and/or receiver for communicating with other mobile device or wireless networks. The ear based sensor(s) can further include the ability to generate audio feedback to the user, including prompts for timing of appropriate MSK movement to achieve MCP, and voice information for further biofeedback and coaching on the accuracy, quality and effectiveness of the MSK pumping activity.

Figure 35A:
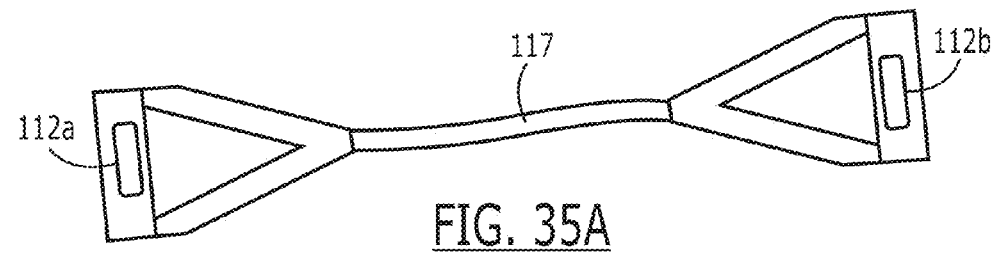
FIG. 35A-B are illustrations of resistance based exercise devices according to an embodiment of the present disclosure.
Figure 35B:
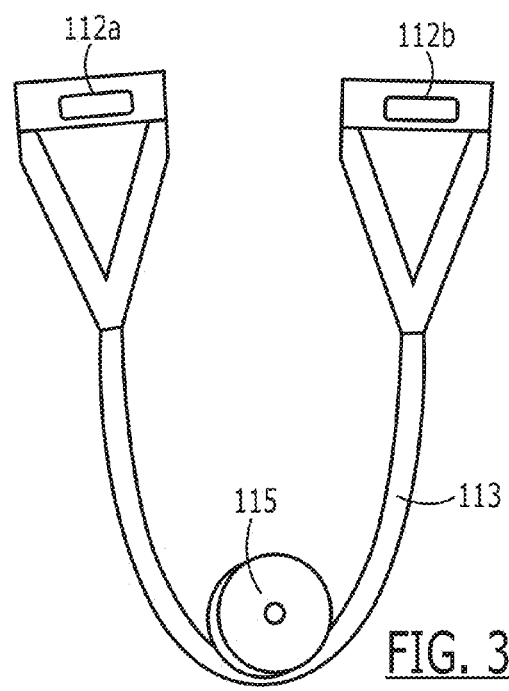
Figure 36:
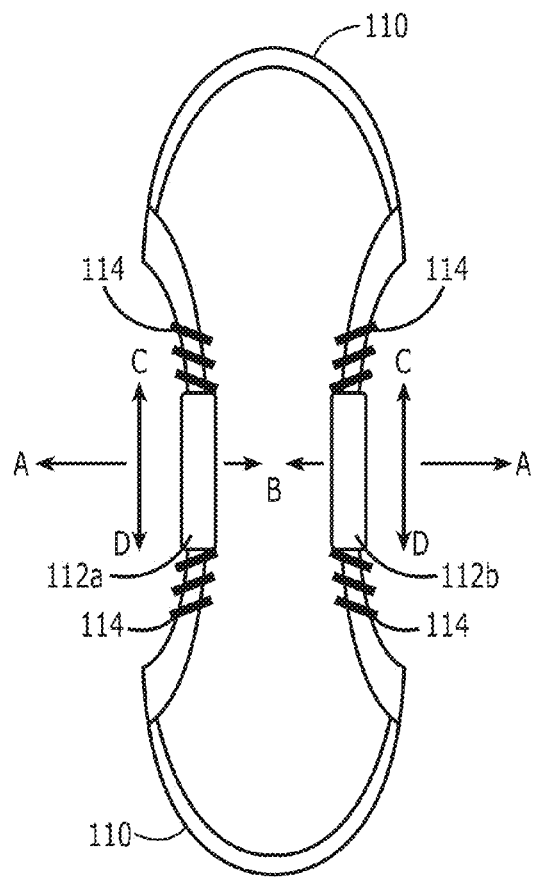
FIG. 36 is an illustration of a spring-based, hand-held system useful as an exercise element according to an embodiment of the present disclosure.

A number of devices are contemplated herein that can facilitate reaching a target HR or a target HR zone through various forms of physical engagement. With reference first to FIGS. 35A, 35B, 36, a fitness device or accessory can be used alone or during ambulatory exercise according to an embodiment of the present disclosure. Simple resistance devices, such as those shown in FIGS. 35A and 35B, can alternatively be used alone or during other exercises, such as walking or running, in order to provide self-resistance as needed to facilitate reaching a desired HR that matches a preferred cadence for enabling MCP, with or without ambulation. In these embodiments, handles 112a and 112b can include ECG sensors for enabling monitoring of the CC while pulling both handles 112 in opposite directions against elongate elastic or inelastic flexible elements 117. In certain embodiments, alternative flexible elongate elements 113 can be configured to be pulled by handles 112 that can include ECG electrodes around a pulley 115 that can be attached to a stationary device or attached to clothing or a harness on a user. The pulley allows both hands 112a, 112b to be pulled in a similar direction while still providing resistance, one against the other. Variable mechanical resistance can also be created by mechanisms housed within the device 115 through which the shafts or ropes 113 are threaded.

Another exemplary embodiment of a hand-held exercise device for enabling MCP via resistance exercise is illustrated in FIG. 36, wherein flexible curved shafts 110 allow a user to simultaneously engage handles 112a, 112b of embodiments of the device in order to exercise by pushing the handles together (B) and pulling the handles apart (A) against the resistance of the flexible shafts 110, or sliding the handles in opposite directions (C/D) against the resistance of additional spring elements 114 and the flexible shafts 110. The system can be configured for use alone or during other activities, such as walking, particularly when increasing the heart rate would be helpful in enabling MCP. The handles 112 may alternatively include ECG sensor electrodes. In addition, a variable resistance device like this can be configured to monitor at least one of the user's skeletal muscle contraction cycle and CV cycle (e.g., via handle 112a, 112b ECG electrodes). A device like this can further be configured to provide guidance to the user on the target timing of at least one of skeletal muscle contraction, skeletal muscle relaxation, and MSK movement. Such a device can be used during ambulation. The device can also, optionally, provide a mechanism prompting the user to time exercise activities in coordination with the CV cycle in order to achieve MCP.

Figure 37:
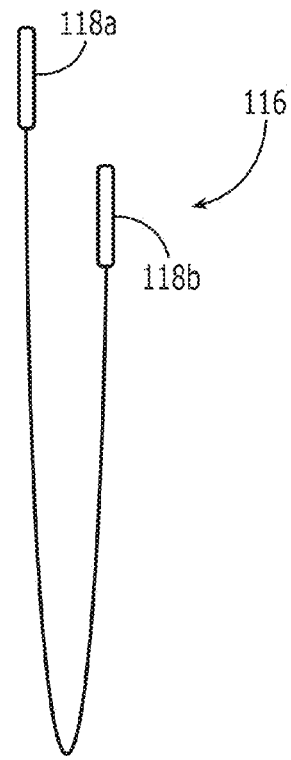
FIG. 37 is an illustration of a jump rope device useful as an exercise element according to an embodiment of the present disclosure.

With reference to FIG. 37, an exercise device 116 that is configured in the form of a jump rope is shown. According to this embodiment, the handles 118a, 118b of the jump rope can include electrodes, such as for an ECG. Movement sensors can also be included in the device 116. The handles can also, optionally, provide a mechanism for prompting the user to jump in coordination with the target timing location in the CC that will enable the user to achieve MCP, utilizing tactile or audible or wireless means of communicating with the user.

As a means to adjust the user's work output, in embodiments of the present disclosure, as part of a device configured to be attached to a user's legs, a set of ankle weights are able to move from the lowest position, close to the ankles of an individual, to an upper position closer to the knee (or alternatively, to positions above the knee). When walking, jogging, or running, the added weights increase the workload since the muscles of the leg have the added burden of moving the mass back and forth with each step. The degree of work is proportional to the mass and range of motion (lever arm) moved. By moving the weight up and down the leg, this workload can be changed without needing to change the mass. When exercising in a manner that attempts to maintain a constant workload (work=force·distance) and power output (work/time), an individual can find a steady pace to walk, jog or run. If the terrain is uneven, sometimes involving an uphill, flat, or down hill incline, the work load changes as the individual climbs or falls against the force of gravity and varies their potential energy (potential energy=mass·gravity·height). Power output can be maintained by varying the individual's stride length and/or pace. The work of moving the legs back and forth can also be changed by varying the location of an added mass. This allows the individual to better maintain stride length and pace over varying degrees of encountered incline. For example, when running on level terrain, the mass can be located in the range of its travel middle close to the middle of the calf. As the incline increases, the mass can be moved closer to the knee, while a downhill incline can be compensated by positioning the mass closer to the ankle. An alternative configuration for variably locating a mass at higher or lower locations along the leg, would include fluid reservoirs at upper and lower locations with a provision for transferring a volume of fluid between them as needed. The mass, in either of these embodiments can be controlled manually by the user, or driven automatically in response to changes in the individual's HR or, alternatively, other measure of work output.

Game controllers, other hardware, and software (by way of example, the Nintendo Wii™, Sony Playstation®, Microsoft Xbox™, Electronic Arts Products, etc., and software and accessories that are compatible with these systems) can be configured to work with at least one of CC sensors and MSK activity sensors in order to enable the methods of achieving, maintaining, utilizing and documenting MCP described in this disclosure. The embodiments described in this disclosure can be integrated into gaming software and hardware for fitness gaming, coaching, training and the like. Game controllers can also be configured to include sensors, including, for example ECG electrodes in the handles of the controller, or accelerometers. In alternative methods and systems of this disclosure, video games, dance programs, or other biofeedback enabled audiovisual exercise instruction enable MSK activity timing to be coordinated with target CC timing locations in order to enable learning about, training in, and enjoying the benefits of MCP during gaming activities.

In non-gaming environments, software applications (so-called apps) for smart-phones, personal digital assistants, music players, watch based devices, portable (laptop, tablet, etc.) computers, etc. can provide various visual and audio feedback and cues to a user, such as are illustrated in FIGS. 38A, B, 39 and 40.

In some embodiments of the disclosure, pedometers or accelerometers can provide data for collection and/or feedback and cues, such as is illustrated in the ankle-based device 542 in FIG. 43A. In alternative configurations, the CV cycle can also be monitored (e.g., an ECG lead or a pulse monitor) via the same ankle based device FIG. 43A. Feedback can be provided by way of audio, tactile, or electronic indicator, or by way of a connection to a smart-phone, personal digital assistant, portable (laptop, tablet, etc.) computer, etc. The sensors can also be integrated into various forms of sports or safety equipment, such as a soccer shin pad or football shoulder pads. The sensors can also be integrated into various devices configured to be attached to or placed within a shoe. "Foot pod" movement sensors FIG. 43B, 43C like those marketed by Nike+, Polar, Suunto, and Garmin, for example, are already configured, in some cases, to provide cadence, speed and distance data. These commercial sensors can also be reconfigured, in some cases, in order to provide more specific movement timing, in order to work more effectively with MCP systems in this disclosure. Alternatively, the sensors could be placed in shoe inserts 141a/b.

Figure 45:
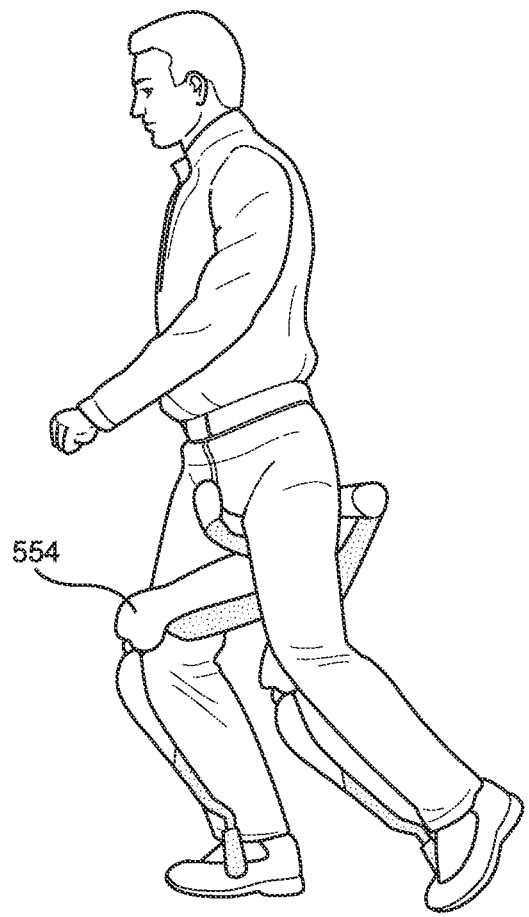
FIG. 45 is an illustration of a mechanical assistance device for ambulation that can also provide assistance in order to facilitate achievement of target movement timing, target HR, or other metrics according to the present disclosure.
Figure 46:
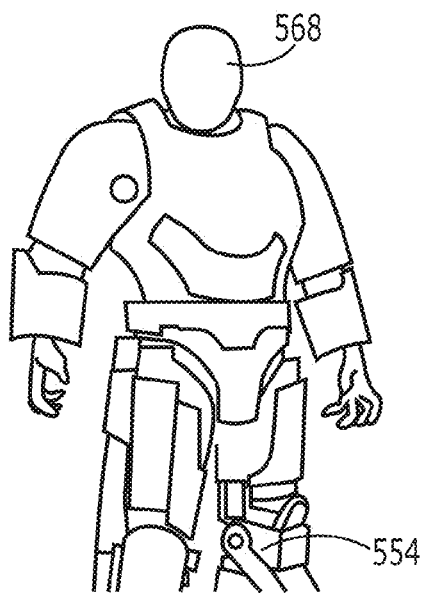
FIG. 46 is an illustration of another exemplary device that can provide mechanical assistance to a user while facilitating achievement of target movement timing, target HR, or other metrics according to the present disclosure.
Figure 47:
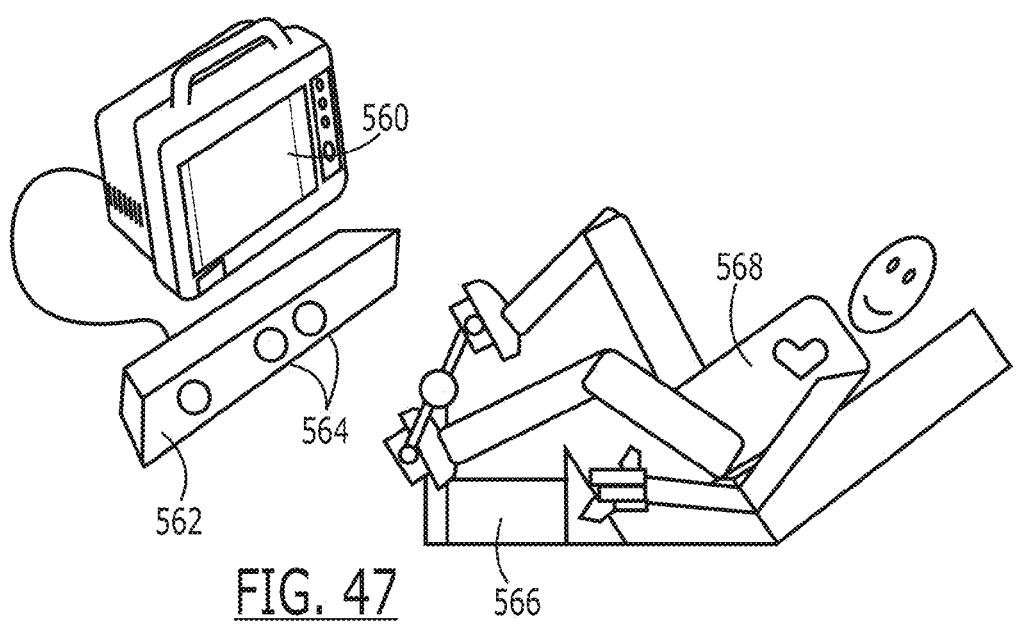
FIG. 47 is an illustration of another exercise device according to an embodiment of the present disclosure.

Timing signals from any the above embodiments can also be used to mechanically assist a user with movement. Movement assist devices, as shown in FIG. 45 and FIG. 46, can be configured to work in conjunction with devices and methods that enable MCP. FIG. 45 depicts a device for assisting ambulation 554, while FIG. 46 depicts an exoskeleton, which also assists a user 568 with ambulation 554, as well as in the performance of other physical activities, similar to those being studied for military and industrial uses, as well as for those with physical disabilities. In this exemplary embodiment of the disclosure, real-time CV analysis can be utilized in creating adaptive timing for a driver for movement timing in order to enable MCP. Other timed mechanical assistance can be provided, for example, by way of driving (in part or completely) or resisting user driving of an exercise device, such as an elliptical trainer FIG. 48A, an exercise bike FIG. 48B, a treadmill FIG. 48C, a pedal assist bike FIG. 48D, a recumbent 166 exercise device FIG. 47, and so forth.

Either digital or analogue communication can be used according to various methods and embodiments of the disclosure, via either wired transmission, or via wireless communication techniques, including radiowaves, microwaves, ultrasound waves (e.g., ranges such as 20-22 KHz or 18-25 KHz), etc. Examples of data transmitted from sensors include heart pump information (e.g. ECG waveforms, R wave timing, RRI, or PPG waveforms and timing); MSK activity timing and quality information (e.g., accelerometry, etc.); Respiratory information; and information on the timing relationship between MSK activity and the heart pump cycle. Different means of communication offer different advantages in terms of signal to noise ratios, energy consumption, reliability, device size, etc. and therefore one or another means may be preferred in specific use scenarios, but not in others.

In certain methods and embodiments of this disclosure, data from sensors can be digitized and sent to other components of the system in data packets for analysis, storage, and further utilization. For example, data packets can contain CV event timestamps and MSK activity timestamps, for analysis, relative to the same clock, or on separate clocks that have been synchronized. Synchronization of clocks between separately located sensors can be achieved in any of a number of ways that have are well understood by those skilled in the art.

In further methods and embodiments of this disclosure, analogue signals can be utilized, with the information delivered by either amplitude modulation (AM) or frequency modulation (FM), using either wired transmission or wireless transmission via radio waves, microwaves, ultrasound waves, or other standard means of wireless communication. AM signals can contain at least one of information on the timing of R waves; the timing of MSK activity; characteristics of the MSK activity (e.g. heel strike); timing relationships between the timing of the R wave and the timing of maximal MSK blood pumping; and a code for linking a specific device with a specific user, in order to avoid cross talk between the devices of different users who can be located in the same vicinity while simultaneously using an embodiment of the device in this disclosure. FM signals can contain similar information and can be carried by similar means.

For embodiments that include the use of a smart phone (e.g., iPhone or Android-based phone), iPod or other personal electronic device that includes a wired, wireless, or built-in audio input and output feature, the delay and/or variable latency in digitizing the incoming signals and the creation of the output signals can disrupt the delay timing of the prompt relative to the detected cardiac event. In many cases, this latency is not inherently known or controllable within the personal electronic device. However, the unknown input/output delay can be characterized in place by feeding-back a representation of the output signal onto the input signal in such a way that the input signal processing can discern the feedback prompt information from the input timing signal.

For example, in one configuration, the timing of the ECG R-wave can be obtained by a wireless receiver that receives its signal from a chest strap worn by the user. This pulse signal, that can be on the order of 3 to 5 volts in amplitude and 10 to 50 msec wide, can be scaled down to a compatible voltage (e.g., 50 mV) and fed into the personal electronic device via its microphone connection. The properly-delayed timing prompt can be provided to the user via the audio output. In order to ensure the delayed prompt occurs at the proper time relative to the user's cardiac activity, the added delays and variable latencies of the chest strap, wireless receiver and personal electronic device must also be known. The applicants have found the chest strap and wireless receivers can be characterized and maintain their delay throughout their usage, however the personal electronic device (e.g., an Android-based smart phone) contributes an unpredictable but otherwise stable delay that changes each time the operating program begins. This unpredictable delay (whether it is stable or not) can be characterized in situ by combining electrically the audio feedback prompt signal and the pulse signal into one signal prior to its being read by the microphone-input digitizer (e.g., by using a passive averaging circuit using resistors, or an inverting or non-inverting summing op-amp circuit). The audio feedback prompt waveform is distinct from the pulse signal input waveform, and the relative timing of the two signals can be compared with the expected timing to empirically determine the additional delay added by the personal electronic device. This characterized additional delay can then be accounted for (e.g., subtracted) in calculating the proper prompt delay time to align it properly with the user's cardiac cycle.

The present disclosure therefore addresses many objectives and many embodiments. A number of those objectives and embodiments are provided below, with the understanding that such a list is not exhaustive, but merely illustrative.

An objective of this system is to provide a method of coordinating the cyclical peripheral vascular pumping associated with rhythmic skeletal muscle contraction and/or MSK movement with the cardiac pumping cycle (CC) in order to consistently provide counter-pulsation to the heart in a manner that is analogous to intra-aortic balloon counter-pulsation and external counter-pulsation.

A further objective of this system is to provide a method coordinating the peripheral physical activity based vascular pumping so that coronary arterial blood flow and myocardial oxygenation are enhanced by increased systemic arterial pressure during diastole.

A further objective of this system is to provide a method coordinating the peripheral physical activity based vascular pumping so that the efficiency of exercise is increased, enabling, for example, a decreased HR at an equivalent work load or power output; or similarly, enabling an increased work load (power output) at an equivalent HR.

A further objective of this system is to provide a method for such coordination, so that venous blood return during diastole is enhanced, thereby potentiating stroke volume and cardiac output. A further objective of this system is to provide a method of coordinating a user's rhythmic MSK activity to their CV rhythm, comprising identifying the timing of a recurring CV event within the CC and providing the user with guidance that includes at least one of an audio, a visual, and a tactile prompt, at an initial delay from the recurring CV event, calculated via an initial computational algorithm, in order to inform the user to initiate the desired rhythmic MSK activity at the targeted timing location in the CC, while monitoring the resultant timing of the rhythmic MSK activity with a sensor, assessing the MSK activity timing relative to the timing of the targeted location in the CC, and processing the monitored resultant timing data in order to adaptively modify the guidance, as indicated, in order to enable the user to further improve or optimize the timing of the rhythmic MSK activity to the targeted location in the CC.

In certain alternative embodiments, the objective of this system is to provide a method of coordinating a user's rhythmic MSK activity to their CV rhythm, comprising identifying the timing of a recurring CV event within the CC and providing the user with a prompt or other guidance that includes at least one of an audio, a visual, and a tactile prompt, at an first delay from the recurring CV event, wherein the user directly or indirectly personally adjusts the MSK activity prompt timing or timing guidance in an attempt to further improve or optimize the delay relative to the recurring CV event, via controls in a user interface of the system.

In certain alternative embodiments, a recurring CV event can comprise measuring at least one of: an ECG signal via at least one of a patch placed on the skin, a chest strap, electrodes designed into the user's apparel, skin electrodes in contact with the user's extremities, electrodes designed into the user's jewelry, or electrodes designed into the user's portable electronics (e.g. headphones and headsets 535, 533, 534, 122).

In certain alternative embodiments, rhythmic MSK activity comprises stepping during walking or running; pumping one's legs during biking; rowing; moving ones limbs during use of an any exercise machine; isotonic, isokinetic, and isometric strength training exercises; moving one's core during use of any exercise machine; moving one's core during any rhythmic exercise.

In certain alternative embodiments, rhythmic MSK activity comprises moving on an exercise machine configured to work with the system, integrating at least one of a CV sensor, a movement sensor, and a user interface.

In certain alternative embodiments, the exercise machine is configured to mechanically assist the timing of the user's MSK movement, as needed.

In certain alternative embodiments, the recurring CV event comprises at least one of ventricular depolarization on ECG, the R-wave on an ECG, end T-Wave on an ECG, aortic valve closure, or the dicrotic notch on a measure of arterial blood flow.

In certain alternative embodiments, the prompt comprises at least one of an audible tone, and audible click, an audible beat, a visual flashing light, and a visual gauge.

In certain alternative embodiments, a sound with a first sound quality is used as the audible prompt to indicate the desired timing of at least one of maximal MSK movement and muscular contraction, while a sound with a second sound quality is also delivered to the user to indicate the actual resultant timing of the MSK activity, in order to enable the user to hear the difference between the desired timing of the MSK activity and its actual timing.

In certain alternative embodiments, the sound quality of the prompt changes the further it gets from the actual MSK activity timing.

In certain alternative embodiments, the quality of the sound of the prompt is different when the user's movement is accurately timed relative to the target timing.

In certain alternative embodiments, the change in sound quality is to a more pleasant sound as the actual timing of physical activity more closely approximates the target timing of same.

In certain alternative embodiments, the pitch of the sound gets higher when the user is moving too early and the pitch of the sound gets lower when the user is moving too late relative to the CV pumping cycle.

In certain alternative embodiments, the prompt comprises an audible musical beat.

In certain alternative embodiments, the audible musical beat is provided from a selection of music of different beats.

In certain alternative embodiments, the music of a particular beat is altered by the system's software to fine-tune the beat in order to optimize the timing of the rhythmic MSK activity.

In certain alternative embodiments, the initial computational algorithm is a calculation that describes at least one of: a specific timing from the last R-Wave that is a designated amount of time that may or may not be a function of the HR or RRI; a specific timing from the last R-Wave that is calculated from a certain percentage of one or more recently sensed RRI(s), and that may or may not be corrected for HR; a specific timing from the last R-Wave that is a certain percentage of the way along the RRI, and that is corrected by a measurement of the individual's baseline T-Wave timing; a specific timing from the last R wave that represents an estimate of the end T-Wave on an ECG by calculating the QT interval corrected for HR; a specific timing from the last R wave that represents an estimate of the end T-Wave on an ECG by calculating the RT interval corrected for HR.

In certain alternative embodiments, the initial computational algorithm is a calculation that guides the user to gradually and comfortably move their HR to a target HR while engaged in MSK activity timing that enables MCP.

In certain alternative embodiments, the prompt delay is timed to modify HR while maintaining MCP, including at least one of adjusting prompt timing to a timing location later in the CC in order to delay next R wave and thereby slow the HR; adjusting prompt timing to a timing location earlier in the CV cycle in order to cause the next R wave to be earlier, and thereby speed up the HR and keeping the prompt at the initial target timing location in order to maintain prompt timing close to aortic valve closure in order to avoid influencing the HR.

In certain alternative embodiments, the initial time delay after the R wave for the prompt is set to occur at a point between 25 and 50% of the RRI.

In alternative embodiments, the MSK activity sensor is at least one of an accelerometer; accelerometers; a gyroscope; gyroscopes; a pressure sensor(s); a pedometer; EMG; a video camera(s), a hall-effect sensor, an optical sensor, a magneto resistive sensor, an inductive sensor, a capacitive, an rpm sensor, etc.

In certain alternative embodiments of the system described in this disclosure, the movement sensor is located together with the CV sensor (e.g. chest strap or patch, or earpiece, or forehead, or temple, or neck). In alternative embodiments the CV and MSK sensors are located together with a processor, as illustrated in FIG. 50. In further embodiments, the sensors are located together but the processor is located separately, e.g. within a smart phone FIG. 27B, music player, or other accessory device, e.g. FIG. 27A.

In alternative embodiments, continuously modifying the guidance includes modifying the prompt algorithm; modifying the prompt timing relative to the recurring CV event; modifying the prompt frequency; modifying the prompt pitch; modifying the quality of the prompt; modifying the duration of the prompt; proving visual feedback as to the timeliness of the prompt.

In certain alternative embodiments, modifying the prompt includes signaling the prompt earlier in the cardiac cycle in order to compensate for MSK activity that is occurring regularly later than the target timing.

In certain alternative embodiments, modifying the prompt includes signaling the prompt later in the cardiac cycle in order to compensate for MSK activity that is occurring regularly before the target timing.

In certain alternative embodiments, further optimizing the timing of the rhythmic MSK pumping to the targeted location in the cardiac pumping cycle entails changing the cadence to a rate that is different by a defined number per minute from the HR in instances when maximal MSK pumping appears to be consistently occurring at the wrong time (e.g., during peak cardiac contraction), despite multiple attempts to guide the user towards the target timing, in order to avoid prolonged CV stress and decreased physiological efficiency potentially associated with persistent MSK pumping during cardiac systole (e.g. iMCP).

In certain alternative embodiments, the defined number per minute difference, between the HR and the prompt cadence, is not less than at least one of: 1 beats per minute (BPM); 2 BPM; 3 BPM; 4 BPM; 5 BPM; and 6 BPM, etc. (i.e., [Abs Value of (Cadence−HR)>X] where X may equal a number between 1 and 10 BPM or X may equal a % of the HR between 1% and 10%).

In certain embodiments, the user achieves the synchronization of CV and MSK activity on an exercise machine in which the user's progress in achieving the desired MCP is displayed via the user interface of the exercise machine.

In certain alternative embodiments, the user achieves the synchronization of CV and MSK activity on an exercise machine in which the work required in order to use the machine is actively modified by the exercise machine in order to facilitate achievement of the cadence timing required for MCP, including at least one of changes in incline, changes in speed, changes in resistance to movement, and changes in size of required movements.

In certain alternative embodiments, the user achieves the synchronization of CV and MSK activity on an exercise machine in which the timing of the user's movement is actively facilitated by motorized movement of the exercise machine at the target timing in the CC.

In certain alternative embodiments, the user achieves the synchronization of CV and MSK activity on an exercise machine in which the timing of the user's musculoskeletal activity is monitored via sensors within the exercise machine.

In certain alternative embodiments, the user achieves the synchronization of CV and MSK activity via feedback from a video game.

In certain alternative embodiments, the user achieves the synchronization of CV and MSK activity via a video game in which the user's progress in achieving the desired MCP is displayed via the user interface of the video game.

In certain alternative embodiments, the user achieves the synchronization of CV and MSK activity via a video game in which the timing of the user's movement is monitored via sensors within the video game hardware.

In certain alternative embodiments, varying the timing of MSK activity is a used as a method to optimize a monitored waveform that is at least one of a measure of arterial pressure, blood volume or blood flow.

In certain embodiments, the computational algorithm is an algorithm for estimating at least one of end T-Wave of the ECG (e.g. end of the QT interval, end RT interval, etc.); the timing of aortic valve closure during early diastole; and the location of the dicrotic notch in a central arterial pressure/flow waveform.

In certain alternative embodiments, prompting a user is accomplished via at least one of an audible signal; a visual signal; a visual display; a tactile signal; an electrical stimulation.

In certain alternative embodiments, the CV effect is at least one of a change of HR; an increase in at least one of diastolic peripheral vascular volume, flow or pressure; or at least one of systolic peripheral vascular volume, flow or pressure.

In certain alternative embodiments, a measure of at least one of peripheral arterial pressure, flow or volume can be used to guide the user to optimize the ratios of the diastolic peak or volume under the diastolic portion of the curve to the systolic peak or volume under the systolic portion of the curve.

In certain alternative embodiments, the measure of arterial blood flow, arterial blood volume and arterial pressure is obtained via photoplethysmography.

In certain alternative embodiments, the information provided to the user in response to the measure includes an indication of the timing of the actual user's MSK activity relative to the desired timing of the user's MSK activity.

In certain alternative embodiments, the information provided to the user in response to the measure includes modification of the timing of the prompt, as needed, in order to guide the user to further optimize the timing of MSK activity relative to the target timing location in the CC.

In certain alternative embodiments, the information provided to the user in response to the measure includes feedback on at least one of the quality and quantity of desired outcome achieved, in order to guide the user to further optimize feedback, as desired.

A further objective of this system is to provide a method of synchronizing CV and MSK activity comprising identifying a target timing in the CC, and prompting a user to achieve rhythmic MSK activity timing at the target timing location in the CC, while monitoring at least one of the timing and quality of the rhythmic MSK activity via a sensor and using that measure to provide information to the user that will guide the user to further optimize MSK activity timing.

A further objective of this system is to provide a means of synchronizing a user's rhythmic MSK activity to their CV rhythm, comprising identifying the timing of a recurring CV event within the CC and providing the user with at least one of an audio, a visual, and a tactile prompt, at an initial delay from the recurring CV event, calculated via an initial computational algorithm in order to inform the user to initiate MSK activity at the targeted timing in the CC relative to the recurring CV event, while monitoring the resultant timing of the rhythmic MSK activity with a sensor, assessing the activity relative to the timing of the targeted location in the cardiac pumping cycle, and processing the monitored resultant timing data in order to continuously modify the prompt, as indicated, in order to enable the user to further optimize the timing of the rhythmic MSK activity to the targeted location in the CC.

A further objective of this system is to provide a means of synchronizing CV and MSK activity comprising identifying a target timing location in the CC, and prompting a user to coordinate rhythmic MSK activity to occur at the target timing, while monitoring the CV effect of the rhythmic MSK activity via at least one of a measure of HR, arterial blood flow, arterial blood volume and arterial pressure and using that measure to provide information to the user that will guide the user to further optimize MSK activity timing in order to optimize the effect of the MSK activity on said measure of CV effect.

A further objective of this system is to provide a means of synchronizing CV and MSK activity comprising identifying the timing of a recurring CV event within the cardiac pumping cycle and prompting a user to coordinate rhythmic MSK activity relative to the timing of the recurring CV event while monitoring the quality of the rhythmic MSK activity via an activity sensor and using that measure to provide information to the user that will guide the user to further optimize MSK activity in order to improve the effect of the MSK activity on said measure of CV effect.

In certain alternative embodiments, the information provided to the user in response to the measure includes an indication of the timing of the user's MSK activity relative to the desired timing of the user's MSK activity.

In certain alternative embodiments, the information provided to the user in response to the measure includes feedback on at least one of the quantity and quality of desired outcome achieved, in order to guide the user to further optimize feedback, as desired.

A further objective of this system is to provide coaching to users to help improve coordination of movement and muscle contraction via interpretation of the MSK activity sensor(s) that is at least one of an accelerometer(s), gyroscope(s), camera(s), EMG, and other electromechanical or solid state MSK activity sensors.

A further objective of this system is to improve the peristaltic nature of MSK pumping by using MSK activity sensors to measure multiple MSK events in at least one extremity. One objective can be to enable the user to optimize the sequential order of muscle contraction. In one alternative embodiment, the user is provided at least one of coaching and feedback on sequentially contracting muscle groups from distal to proximal, for example, the user can be encouraged to substantially flex the calf of the lower leg before the thigh of the upper leg before the muscle of the buttocks and core of the body.

A further objective of this system is to enable the user to optimize acceleration/deceleration by providing the user with feedback on at least one of: the force of movement; the impact of movement; the magnitude of acceleration & deceleration vs. inertia, the coordination of movement of the upper & lower extremities; and the coordination of movement of the right and left limbs.

The embodiments described, and hence the scope of the descriptions of systems and methods below, encompass embodiments in hardware, software, firmware, or a combination thereof. It will also be appreciated that the methods, in the form of instructions having a sequence, syntax, and content, of the present disclosure can be stored on (or equivalently, in) any of a wide variety of computer-readable media such as magnetic media, optical media, magneto-optical media, electronic media (e.g., solid state ROM or RAM), etc., the form of which media not limiting the scope of the present disclosure. A computer reading said media is operable to either transfer (e.g., download) said instructions thereto and then operate on those instructions, or cause said instructions to be read from the media and operate in response thereto. Furthermore, devices (e.g., a reader) for accessing the instructions on said media can be contained within or connected directly to the computer on which those instructions operate, or can be connected via a network or other communication pathway to said computer.

The physics of modern electrical and mechanical devices and the methods of their production and use are not absolutes, but rather efforts (statistical or otherwise) to produce a desired device and/or result. Accordingly, no limitation in the description of the present disclosure or its claims can or should be read as absolute. To further highlight this, the term "substantially" or similar terms can occasionally be used herein in association with a description (although consideration for variations and imperfections is not restricted to only those limitations used with that term). While as difficult to precisely define as the limitations of the present disclosure themselves, we intend that this term be interpreted as "to a large extent", "as nearly as practicable", "within technical limitations", and the like.

Furthermore, while a plurality of exemplary embodiments have been presented in the foregoing detailed description, it should be understood that a vast number of variations exist, and these exemplary embodiments are merely representative examples, and are not intended to limit the scope, applicability or configuration of the disclosure in any way. Various of the above-disclosed and other features and functions, or alternative thereof, may be desirably combined into many other different systems or applications. Various presently unforeseen or unanticipated alternatives, modifications variations, or improvements therein or thereon can be subsequently made by those skilled in the art which are also intended to be encompassed by the present disclosure.

In addition, the methods and systems described herein guide the user in the performance of two major categories of rhythmic physical activities, namely MSK movement and skeletal muscle contraction cycles, in order to coordinate peripheral vascular pumping with the heart's pumping activity. These two categories of rhythmic physical activities, together or individually, are included in the scope of the disclosure, even where only one of the two categories has been described. Therefore, for example, the descriptive phrases MSK movement, skeletal muscle contraction, skeletal muscle relaxation, MSK pumping cycles, and MSK activity should be considered included where one or more of the terms was not mentioned.

The methods and systems described herein are used during "rhythmic physical activities". The phrase "repetitive physical activities" also describes appropriate use scenarios, and both phrases should be considered included whenever one of the terms was not mentioned.

Therefore, the foregoing description provides those of ordinary skill in the art with a convenient guide for implementation of the disclosure, and contemplates that various changes in the functions and arrangements of the described embodiments can be made without departing from the spirit and scope of the disclosure.

What is claimed is:

1. A method for detecting a cardiovascular cycle of a user, generating data corresponding to the cardiovascular cycle and using the data to coordinate a rhythmic musculoskeletal activity of the user with the cardiovascular cycle of the user, comprising:
    detecting instances of a selected aspect of the cardiovascular cycle of the user using a first detector, said selected aspect repeating at a heart rate of the user;
    specifying a target timing location in the cardiovascular cycle to a subsystem based on the data generated from a plurality of said instances detected by the first detector;
    recurrently providing a prompt from a prompt device to the user at a prompt rate to thereby provide a timing indication for performance of the rhythmic musculoskeletal activity, the prompt being provided such that the heart rate is substantially an integer multiple of the prompt rate; and
    adaptively adjusting timing of the prompt using a processor that receives the target timing location and adaptively adjusts the timing of the prompt automatically so that the prompt is provided by the prompt device to the user substantially at the target timing location in the cardiovascular cycle in response to detected change in the timing of the cardiovascular cycle.

2. The method of claim 1, wherein said adaptively adjusting maintains either a fixed percentage of an R-wave-to-R-wave time interval of the user or said prompt being located at a fixed event in the cardiovascular cycle of the user.

3. The method of claim 1, wherein said adjusting comprises a user-selected, time-based offset from said aspect of the user's cardiovascular cycle.

4. The method of claim 1, wherein said adjusting comprises an offset from said aspect of the user's cardiovascular cycle automatically determined based on a physiological attribute of the user.

5. The method of claim 4, wherein the physiological attribute is selected, using the processor, from the group consisting of: user age; user heart rate; user blood pressure; user's maximum heart rate; and, user target heart rate.

6. The method of claim 1, wherein said adjusting comprises an offset from said aspect of the user's cardiovascular cycle automatically determined based on a type of rhythmic musculoskeletal activity the user is to perform.

7. The method of claim 1, further comprising:
    detecting a selected recurrent component of the user's rhythmic musculoskeletal activity using a second detector that repeats at a cadence of the user; and
    wherein based on said detected components of the user's cardiovascular cycle and the user's rhythmic musculoskeletal activity, further adjusting said prompt using the processor such that said prompt is provided to guide timing of the selected recurrent component of the user's rhythmic musculoskeletal activity to occur at a targeted timing relative to the selected recurrent aspect of the user's cardiovascular cycle.

8. The method of claim 7, further comprising:
    determining a desired offset between the provision of said prompt and the selected recurrent component the user's rhythmic musculoskeletal activity using the processor;
    determining an actual offset between the provision of said prompt and the selected recurrent component the user's rhythmic musculoskeletal activity using the processor; and
    in response to said determined actual offset, further adjusting provision of the prompt to permit said component of the user's rhythmic musculoskeletal activity to occur at a desired point in the user's cardiovascular cycle using the processor.

9. The method of claim 7, further comprising:
    determining an offset between the selected recurrent component the user's rhythmic musculoskeletal activity and the target timing location in the cardiovascular cycle using the processor; and
    in response to said determined offset, further adjusting provision of the prompt using the processor to permit said component of the user's rhythmic musculoskeletal activity to occur at a desired point in the user's cardiovascular cycle.

10. The method of claim 1, wherein said integer multiple is determined automatically using the processor based on at least one of the group consisting of: the type of rhythmic musculoskeletal activity the user is to perform; a ratio of the user's heart rate to a target musculoskeletal activity cadence; and a ratio of the user's heart rate to an indication of their actual musculoskeletal activity cadence.

11. The method of claim 1, wherein said prompt is at least one of the group consisting of: an audio prompt; a visual prompt; and, a tactile prompt.

12. A method for detecting a cardiovascular cycle of a user, generating data corresponding to the cardiovascular cycle and using the data to coordinate a rhythmic musculoskeletal activity of the user with the cardiovascular cycle of the user, comprising:
    providing a recurrent prompt to the user from a prompt device to thereby provide a timing indication to the user for performance of the rhythmic musculoskeletal activity;

detecting a selected recurrent aspect of the user's cardiovascular cycle that repeats at a heart rate of the user using a first detector;

detecting a selected recurrent component of the user's rhythmic musculoskeletal activity that repeats at a cadence of the user using a second detector; and wherein based on the data generated from said detected aspect of the user's cardiovascular cycle and the detected selected recurrent component of the user's rhythmic musculoskeletal activity, adapting provision of the prompt using a processor that receives the target timing location and adaptively adjusts the timing of the prompt automatically such that said prompt is provided so as to coordinate timing of the selected recurrent component of the user's rhythmic musculoskeletal activity to occur with a targeted timing relationship relative to the timing of the selected recurrent aspect of the user's cardiovascular cycle.

13. The method of claim 12, wherein said prompt is provided substantially at a desired point in the user's cardiovascular cycle.

14. The method of claim 12, wherein said selected recurrent aspect of the user's cardiovascular cycle is represented by a first signal from the first detector and said recurrent component of the user's rhythmic musculoskeletal activity is represented by a second signal from the second detector, and said adapting of the provision of the prompt comprises comparing timing of the first and second signals relative to one another using the processor.

15. The method of claim 14, wherein:
the recurrent prompt is provided at a prompt rate using the prompt device;
the cardiovascular cycle is a full cycle of the user's heart pumping function;
the heart rate of the user is an integer multiple of the prompt rate; and
the prompt is adaptively provided at an offset from an aspect of the detected cardiovascular cycle of the user.

16. The method of claim 15, wherein said offset is selected from the group consisting of: a time-based offset; and, a percentage of an interval-based offset.

17. The method of claim 14, wherein said recurrent first signal is selected from the group consisting of: an electro-cardio-graphic R-wave of the user, an electro-cardio-graphic T-wave of the user; an end of the electro-cardio-graphic T-wave of the user; a feature of a photoplethysmogram (PPG) waveform of the user; a peak of a cardiovascular systolic pressure of the user; a nadir of a diastolic cardiovascular pressure of the user; and, a transition point in a cardiovascular pressure of the user.

18. The method of claim 17, wherein said first signal comprises the user's electro-cardio-graphic R-wave, and further wherein said offset is a time-based offset, $\tau$, such that the prompt is provided at time $\tau$ after detection of the R-wave.

19. The method of claim 18, wherein $\tau$ is determined as a function of at least one value from the group consisting of: a target heart rate of the user; beat-to-beat heart rate of the user; average heart rate of the user; pulse-periods of the user; average pulse-period of the user; and, a type of user activity producing the recurrent component the user's rhythmic musculoskeletal activity.

20. The method of claim 19, wherein $\tau$ is determined as a function of the target heart rate, and further comprising receiving a user input representing the target heart rate using at least one of the first detector and a user interface.

21. The method of claim 12, wherein the second detector includes the use of at least one of an accelerometer, an EMG sensor, a pressure sensor, a gyroscope, and an electromechanical sensor.

22. The method of claim 12, wherein said prompt is at least one of the group consisting of: an audio prompt; a visual prompt; and, a tactile prompt.

23. The method of claim 12, further comprising:
determining a desired offset between the provision of said prompt and the selected recurrent component the user's rhythmic musculoskeletal activity using the processor;
determining an actual offset between the provision of said prompt and the selected recurrent component the user's rhythmic musculoskeletal activity using the processor; and
in response to said determined actual offset, further adapting provision of the prompt using the processor.

24. The method of claim 23, wherein said actual offset is determined as a time-averaged offset between the provision of said prompt and the selected recurrent component the user's rhythmic musculoskeletal activity.

25. The method claim 23, further comprising, in response to said determined actual offset, automatically adjusting conditions of the rhythmic musculoskeletal activity to reduce said actual offset using the processor.

26. The method of claim 25, wherein said automatically adjusting comprises providing a signal from the processor to an electro-mechanical exercise apparatus so as to adjust operating conditions of said electro-mechanical exercise apparatus.

27. The method of claim 12, further comprising:
determining an actual offset between the selected recurrent component of the user's rhythmic musculoskeletal activity and the target timing location in the cardiovascular cycle using the processor; and
in response to said determined actual offset, further adjusting provision of the prompt using the processor to permit said component of the user's rhythmic musculoskeletal activity to occur at a desired point in the user's cardiovascular cycle.

28. The method of claim 27, wherein said actual offset is determined using the processor as a time-averaged offset between the selected recurrent component of the user's rhythmic musculoskeletal activity and the target timing location in the cardiovascular cycle.

29. The method claim 27, further comprising, in response to said determined actual offset, automatically adjusting conditions of the rhythmic musculoskeletal activity to reduce said actual offset using the processor.

30. The method of claim 29, wherein said automatically adjusting comprises providing a signal from the processor to an electro-mechanical exercise apparatus so as to adjust operating conditions of said electro-mechanical exercise apparatus.

31. The method of claim 12, wherein said prompt is provided substantially at a variable desired point in the user's cardiovascular cycle.

32. The method of claim 31, wherein the desired point in the user's cardiovascular cycle at which the prompt is adaptively provided varies as a function of time that the user performs the rhythmic musculoskeletal activity.

33. The method of claim 31, wherein the desired point in the user's cardiovascular cycle at which the prompt is adaptively provided varies as a function of the user's heart rate while the user performs the rhythmic musculoskeletal activity.

34. The method of claim 31, wherein the desired point in the user's cardiovascular cycle at which the prompt is adaptively provided varies as a function of the user's blood pressure while the user performs the rhythmic musculoskeletal activity.

35. The method of claim 12, further comprising:
using the processor to selectively modify said prompt based on at least one condition selected from the group consisting of: heart rate of the user while performing said rhythmic musculoskeletal activity; cadence of the user while performing said rhythmic musculoskeletal activity; and, relative timing relationship between the selected recurrent component of the user's rhythmic musculoskeletal activity and the selected recurrent aspect of the user's cardiovascular cycle.

36. The method of claim 35, wherein said prompt is further selectively modified when a relative timing relationship between the selected recurrent component of the user's rhythmic musculoskeletal activity and the selected recurrent aspect of the user's cardiovascular cycle represents an undesirable condition.

37. A system for detecting a cardiovascular cycle of a user, generating data corresponding to the cardiovascular cycle and using the data to coordinate a rhythmic musculoskeletal activity of the user with the cardiovascular cycle of the user, comprising:
a first detector for detecting instances of a selected aspect of the cardiovascular cycle of the user, said selected aspect repeating at a heart rate of the user;
a subsystem for specifying a target timing location in the cardiovascular cycle of the user based on the data generated from a plurality of said instances detected by the first detector;
a prompt device for recurrently providing a prompt to the user at a prompt rate to thereby provide a timing indication for performance of the rhythmic musculoskeletal activity, the prompt being provided such that the heart rate is substantially an integer multiple of the prompt rate; and
a processor that receives target timing location and adaptively adjusting timing of the prompt automatically so that the prompt is provided by the prompt device to the user substantially at the target timing location in the cardiovascular cycle in response to a detected change in the timing of the cardiovascular cycle.

38. The system of claim 37, wherein said processor is configured to adaptively adjust said timing to maintain either a fixed percentage of an R-wave to-R-wave time interval of the user or to located said prompt at a fixed event in the cardiovascular cycle of the user.

39. The system of claim 37, further comprising an interface configured to permit user-selected, time-based adjustment of said offset.

40. The system of claim 37, further comprising a user interface for entering or selecting, or a sensor for sensing a physiological attribute of the user, and further wherein said processor is configured such that said adjusting comprises an offset from said aspect of the user's cardiovascular cycle automatically determined based on said physiological attribute of the user.

41. The system of claim 40, wherein said physiological attribute is selected from the group consisting of: user age; user weight; user blood pressure; user heart rate; user's maximum heart rate; and, user target heart rate.

42. The system of claim 37, wherein said processor is configured such that said adjusting comprises an offset from said aspect of the user's cardiovascular cycle automatically determined based on a type of rhythmic musculoskeletal activity the user is to perform.

43. The system of claim 37, further comprising:
a second detector for detecting a selected recurrent component of the user's rhythmic musculoskeletal activity that repeats at a cadence of the user; and
said processor is configured such that, based on said detected components of the user's cardiovascular cycle and the user's rhythmic musculoskeletal activity, said processor further adjusts said prompt such that said prompt is provided to guide timing of the selected recurrent component of the user's rhythmic musculoskeletal activity to occur substantially at the targeted timing relative to the selected recurrent aspect of the user's cardiovascular cycle.

44. The system of claim 43, further comprising:
said processor configured for determining a desired offset between the provision of said prompt and the selected recurrent component of the user's rhythmic musculoskeletal activity;
said processor further configured for determining an actual offset between the provision of said prompt and the selected recurrent component of the user's rhythmic musculoskeletal activity; and
said processor further configured for, in response to said determined actual offset, further adjusting provision of the prompt to permit said component of the user's rhythmic musculoskeletal activity to occur at a desired point in the user's cardiovascular cycle.

45. The system of claim 43, further comprising:
said processor further configured for determining an offset between the selected recurrent component of the user's rhythmic musculoskeletal activity and the target timing location in the cardiovascular cycle; and
said processor further configured for, in response to said determined offset, further adjusting provision of the prompt to permit said component of the user's rhythmic musculoskeletal activity to occur at a desired point in the user's cardiovascular cycle.

46. The system of claim 37, wherein said processor is further configured for automatically determining said integer multiple based on at least one of the group consisting of: the type of rhythmic musculoskeletal activity the user is to perform; a ratio of the user's heart rate to a target musculoskeletal activity cadence; and a ratio of the user's heart rate to an indication of their actual musculoskeletal activity cadence.

47. The system of claim 37, wherein said prompt device is configured to provide said prompt of a type selected from the group consisting of:
an audio prompt; a visual prompt; and, a tactile prompt.

48. A system for detecting a cardiovascular cycle of a user, generating data corresponding to the cardiovascular cycle and using the data to coordinate a rhythmic musculoskeletal activity of the user with the rhythmic cardiovascular cycle of the user, comprising:
a prompt device for providing a recurrent prompt to the user to thereby provide a timing indication for performance of the rhythmic musculoskeletal activity;
a first detector for detecting a selected recurrent aspect of the user's cardiovascular cycle that repeats at a heart rate of the user;
a second detector for detecting a selected recurrent component of the user's rhythmic musculoskeletal activity that repeats at a cadence of the user; and
a processor, responsive to the data generated from said detection of said selected recurrent aspect of the cardiovascular cycle of the user and the detection of said selected recurrent component of the rhythmic musculoskeletal activity of the user, for automatically and adaptively providing the prompt so as to coordinate timing of the selected recurrent component of the rhythmic musculoskeletal activity of the user to occur with a targeted timing relationship relative to the timing of the selected recurrent aspect of the cardiovascular cycle of the user.

49. The system of claim 48, wherein said processor is configured to provide said prompt substantially at a desired point in the user's cardiovascular cycle.

50. The system of claim 48, wherein said first detector represents said selected recurrent aspect of the user's cardiovascular cycle by a first detected signal and said second detector represents said recurrent component of the user's rhythmic musculoskeletal activity by a second detected signal, and said processor is configured to adapt the provision of the prompt by comparing timing of the first and second detected signals relative to one another.

51. The system of claim 50, wherein:
the prompt device provides the recurrent prompt at a prompt rate;
the cardiovascular cycle is a full cycle of the user's heart pumping function;
the detected heart rate of the user is an integer multiple of the prompt rate; and
said processor is configured to provide the prompt at an offset from the aspect of the cardiovascular cycle of the user.

52. The system of claim 51, wherein said processor is configured to provide the prompt at an offset selected from the group consisting of: a time-based offset; and, a percentage of an interval-based offset.

53. The system of claim 50, wherein said recurrent first detected signal is selected from the group consisting of: an electro-cardio-graphic R-wave of the user, an electro-cardio-graphic T-wave of the user; an end of an electro-cardio-graphic T-wave of the user; a feature of a photoplethysmogram (PPG) waveform of the user; a peak of a cardiovascular systolic pressure of the user; a nadir of a diastolic cardiovascular pressure of the user; and, a transition point in a cardiovascular pressure of the user.

54. The system of claim 53, wherein said recurrent first detected signal comprises the user's electro-cardio-graphic R-wave, and further wherein said offset is a time-based offset, τ, said prompt device providing said prompt at time τ after detection by said first detector of the R-wave.

55. The system of claim 54, wherein said processor is configured to determine τ as a function of at least one value from the group consisting of: a target heart rate of the user; beat-to-beat heart rate of the user; average heart rate of the user; pulse-periods of the user; average pulse-period of the user; and, a type of user activity producing the recurrent component the user's rhythmic musculoskeletal activity.

56. The system of claim 55, wherein τ is determined as a function of the target heart rate, and further comprising an interface for receiving a user input representing the target heart rate.

57. The system of claim 48, further comprising, and configured for measurement of the recurrent component of the user's rhythmic musculoskeletal activity, at least one of an accelerometer, an EMG sensor, a pressure sensor, a gyroscope, and an electromechanical sensor.

58. The system of claim 48, wherein said prompt device is configured to provide said prompt as at least one of the group consisting of: an audio prompt; a visual prompt; and, a tactile prompt.

59. The system of claim 48, further comprising:
said processor configured for determining a desired offset between the provision of said prompt and the selected recurrent component of the user's rhythmic musculoskeletal activity;
said processor configured for determining an actual offset between the provision of said prompt and the selected recurrent component of the user's rhythmic musculoskeletal activity; and
said processor configured for, in response to said determined actual offset, further adapting provision of the prompt.

60. The system of claim 59, wherein said processor is configured for determining said actual offset as a time-averaged offset between the provision of said prompt and the selected recurrent component of the user's rhythmic musculoskeletal activity.

61. The system claim 59, wherein said processor is configured for automatically adjusting, in response to said determined actual offset, conditions of the rhythmic musculoskeletal activity to reduce said actual offset.

62. The system of claim 61, further comprising an electro-mechanical exercise apparatus communicatively coupled to said processor such that said automatically adjusting comprises said processor providing a signal to said electro-mechanical exercise apparatus so as to adjust operating conditions of said electro-mechanical exercise apparatus.

63. The system of claim 48, further comprising:
a third detector for determining an actual offset between the selected recurrent component of the user's rhythmic musculoskeletal activity and the target timing location in the cardiovascular cycle; and
said processor configured such that, in response to said determined actual offset, provision of the prompt is further adjusted to permit said component of the user's rhythmic musculoskeletal activity to occur at a desired point in the user's cardiovascular cycle.

64. The system of claim 63, wherein said processor is configured to determine said actual offset as a time-averaged offset between the selected recurrent component of the user's rhythmic musculoskeletal activity and the target timing location in the cardiovascular cycle.

65. The system claim 63, wherein said processor is configured to, in response to said determined actual offset, automatically adjust conditions of the rhythmic musculoskeletal activity to reduce said actual offset.

66. The system of claim 65, further comprising an electro-mechanical exercise apparatus communicatively coupled to said processor such that said automatically adjusting comprises said processor providing a signal to said electro-mechanical exercise apparatus so as to adjust operating conditions of said electro-mechanical exercise apparatus.

67. The system of claim 48, wherein said processor is configured to provide said prompt substantially at a variable point in the user's cardiovascular cycle.

68. The system of claim 67, wherein said processor is configured to operate with said desired point varying as a function of time that the user performs the rhythmic musculoskeletal activity.

69. The system of claim 67, wherein said processor is configured to operate with said desired point varying as a function of the user's heart rate while the user performs the rhythmic musculoskeletal activity.

70. The system of claim 67, wherein said processor is configured to operate with said desired point varying as a function of the user's blood pressure while the user performs the rhythmic musculoskeletal activity.

71. The system of claim 48, further comprising:
said processor being configured to selectively modify said prompt based on at least one condition selected from the group consisting of: heart rate of the user while performing said rhythmic musculoskeletal activity; cadence of the user while performing said rhythmic musculoskeletal activity; and, relative timing relationship between the selected recurrent component of the user's rhythmic musculoskeletal activity and the selected recurrent aspect of the user's cardiovascular cycle.

72. The system of claim 71, wherein said processor is configured to selectively modify said prompt when a relative timing relationship, determined by said processor, between the selected recurrent component of the user's rhythmic musculoskeletal activity and the selected recurrent aspect of the user's cardiovascular cycle represents an undesirable condition.

* * * * *